United States Patent
Sastry-Dent et al.

(10) Patent No.: US 11,098,316 B2
(45) Date of Patent: Aug. 24, 2021

(54) OPTIMAL SOYBEAN LOCI

(71) Applicant: Corteva Agriscience LLC, Indianapolis, IN (US)

(72) Inventors: Lakshmi Sastry-Dent, Avon, IN (US); Zehui Cao, Carmel, IN (US); Shreedharan Sriram, Indianapolis, IN (US); Steven R. Webb, Westfield, IN (US); Debra L. Camper, Indianapolis, IN (US); W. Michael Ainley, Carmel, IN (US)

(73) Assignee: Corteva Agriscience LLC, Indianapolis, IN (US)

(*) Notice: Subject to any disclaimer, the term of this patent is extended or adjusted under 35 U.S.C. 154(b) by 0 days.

(21) Appl. No.: 16/123,326

(22) Filed: Sep. 6, 2018

(65) Prior Publication Data

US 2018/0371478 A1    Dec. 27, 2018

Related U.S. Application Data

(63) Continuation of application No. 15/867,770, filed on Jan. 11, 2018, now Pat. No. 10,106,804, which is a continuation of application No. 14/531,748, filed on Nov. 3, 2014, now Pat. No. 9,909,131.

(60) Provisional application No. 61/899,602, filed on Nov. 4, 2013.

(51) Int. Cl.
*C12N 15/82* (2006.01)
*A01H 5/10* (2018.01)

(52) U.S. Cl.
CPC ......... *C12N 15/8213* (2013.01); *A01H 5/10* (2013.01); *C12N 15/8243* (2013.01); *C12N 15/8273* (2013.01); *C12N 15/8274* (2013.01); *C12N 15/8286* (2013.01)

(58) Field of Classification Search
None
See application file for complete search history.

(56) References Cited

U.S. PATENT DOCUMENTS

| | | |
|---|---|---|
| 4,769,061 A | 9/1988 | Comai |
| 4,810,648 A | 3/1989 | Stalker |
| 4,940,835 A | 7/1990 | Fraley et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,200,759 B1 | 3/2001 | Dove et al. |
| 6,242,568 B1 | 6/2001 | Barbas et al. |
| 6,453,242 B1 | 9/2002 | Eisenberg et al. |
| 6,479,626 B1 | 11/2002 | Kim et al. |
| 6,534,261 B1 | 3/2003 | Cox et al. |
| 6,599,692 B1 | 6/2003 | Case et al. |
| 6,689,558 B2 | 2/2004 | Case |
| 6,794,136 B1 | 9/2004 | Eisenberg et al. |
| 6,903,185 B2 | 6/2005 | Kim et al. |
| 6,992,239 B2 | 1/2006 | Fuessley et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,462,758 B2 | 12/2008 | Biesgen |
| 8,420,782 B2 | 4/2013 | Bonas et al. |
| 8,440,431 B2 | 5/2013 | Voytas et al. |
| 2003/0232410 A1 | 12/2003 | Liljedahl et al. |
| 2005/0026157 A1 | 2/2005 | Baltimore et al. |
| 2005/0064474 A1 | 3/2005 | Holmes et al. |
| 2005/0208489 A1 | 9/2005 | Carroll et al. |
| 2005/0267061 A1 | 12/2005 | Martin |
| 2006/0188987 A1 | 8/2006 | Guschin et al. |
| 2007/0022485 A1 | 1/2007 | Takeda et al. |
| 2007/0134796 A1 | 6/2007 | Holmes et al. |
| 2007/0218528 A1 | 9/2007 | Miller |
| 2007/0271629 A1 | 11/2007 | Ananiev et al. |
| 2007/0271636 A1 | 11/2007 | Nelson et al. |
| 2008/0131962 A1 | 6/2008 | Miller |
| 2008/0182332 A1 | 7/2008 | Cai |
| 2009/0111119 A1 | 4/2009 | Doyon et al. |
| 2009/0117617 A1 | 5/2009 | Holmes et al. |
| 2009/0205083 A1 | 8/2009 | Gupta et al. |
| 2009/0263900 A1 | 10/2009 | DeKelver et al. |
| 2010/0047805 A1 | 2/2010 | Wang |
| 2010/0199389 A1 | 8/2010 | Butler et al. |
| 2011/0041195 A1 | 2/2011 | Doyon |
| 2011/0145940 A1 | 6/2011 | Voytas et al. |
| 2011/0167521 A1 | 7/2011 | DeKelver et al. |

(Continued)

FOREIGN PATENT DOCUMENTS

| | | |
|---|---|---|
| EP | 0 242 246 | 11/1992 |
| GB | 2338237 | 8/1998 |

(Continued)

OTHER PUBLICATIONS

Day et al 2000 (Genes and Development 14: p. 2869-2880) (Year: 2000).*
Schmutz, et al., 2013, Whole Genome Shotgun Sequence.
Valton et al., 5' Cytosine-Phosphoguanine (CpG) Methylation Impacts the Activity of Natural and Engineere Meganucleases, JBC (2012) vol. 287 (36) pp. 30139-30150.
Daboussi et al., Chromosomal Contxt and Epigenetic Mechanisms Control the efficacy of Genome Editing by Rare-Cutting Designer Endonucleases, Nuc Acids Research (2012) vol. 40(13) pp. 6367-6379.

(Continued)

*Primary Examiner* — Matthew R Keogh

(57) ABSTRACT

As disclosed herein, optimal native genomic loci of soybean plants have been identified that represent best sites for targeted insertion of exogenous sequences.

19 Claims, 16 Drawing Sheets

Specification includes a Sequence Listing.

(56) References Cited

U.S. PATENT DOCUMENTS

| | | |
|---|---|---|
| 2011/0185445 A1 | 7/2011 | Bogner et al. |
| 2011/0189775 A1 | 8/2011 | Ainley et al. |
| 2011/0201055 A1 | 8/2011 | Doyon et al. |
| 2011/0207221 A1 | 8/2011 | Cost et al. |
| 2011/0229582 A1 | 9/2011 | Fischer et al. |
| 2011/0239315 A1 | 9/2011 | Bonas et al. |
| 2011/0277189 A1* | 11/2011 | Kondo .............. C12N 15/8213 800/293 |
| 2011/0281361 A1 | 11/2011 | DeKelver et al. |
| 2011/0287545 A1 | 11/2011 | Cost et al. |
| 2011/0301073 A1 | 12/2011 | Gregory et al. |
| 2013/0239252 A1 | 9/2013 | Wigge et al. |
| 2013/0254932 A1 | 9/2013 | Nott et al. |
| 2014/0283166 A1 | 9/2014 | Chomet et al. |

FOREIGN PATENT DOCUMENTS

| | | |
|---|---|---|
| WO | 93/19181 | 9/1993 |
| WO | 95/19431 | 7/1995 |
| WO | 96/06166 | 2/1996 |
| WO | 96/30517 | 10/1996 |
| WO | 98/53057 | 11/1998 |
| WO | 98/53058 | 11/1998 |
| WO | 98/53059 | 11/1998 |
| WO | 98/53060 | 11/1998 |
| WO | 98/54311 | 12/1998 |
| WO | 00/27878 | 5/2000 |
| WO | 01/60970 | 8/2001 |
| WO | 01/88197 | 11/2001 |
| WO | 02/016536 | 2/2002 |
| WO | 02/077227 | 10/2002 |
| WO | 02/099084 | 12/2002 |
| WO | 03/016496 | 2/2003 |
| WO | 05/012515 | 2/2005 |
| WO | 05/107437 | 11/2005 |
| WO | 07/014275 | 2/2007 |
| WO | 07/053482 | 5/2007 |
| WO | 2009/006297 | 1/2009 |
| WO | WO2009/006297 | 1/2009 |
| WO | 2009/099580 | 8/2009 |
| WO | 2011/022469 | 2/2011 |
| WO | WO2011/022469 | 2/2011 |
| WO | 2011/066384 | 6/2011 |
| WO | WO2011/066384 | 6/2011 |
| WO | 13/144663 | 3/2013 |
| WO | 2013/119770 | 8/2013 |
| WO | WO2013/119770 | 8/2013 |
| WO | 2013144663 | 10/2013 |

OTHER PUBLICATIONS

Gao et al., Heritable Targeted Mutagenesis in Maize using a Designed Endonuclease, The Plant Journal, (2009), vol. 61 (1) pp. 176-187.

Zhu et al., Hypomethylated sequences: Characterization of the Duplicate Soybean Genome, Molecular and General Genetics, vol. 244, No. 6 (Jan. 1, 1994) p. 638-645.

Bolon et al Phenotypic and Genomic Analysis of a Fast Neutron Mutant Population in Soybean, Plant Physiology, vol. 156(1) (May 1, 2011) p. 240253.

Schmutz et al, Genome Sequence of the Palaeopolyploid Soybean, Nature, vol. 463 (Jan. 14, 2010) p. 178-183.

Kim et al., "Quantitative Trait Loci Associated with Oligosaccharide and Sucrose Contents in Soybean (*Glycine max* L.) Myoung-Gun Choung 3, and Duck" Journal of Plant Biology, Mar. 1, 2005, pp. 106-112.

Yang et al., "Genome structure in soybean revealed by a genomewide genetic map constructed from a single population" Genomics, vol. 92, No. 1, Jul. 1, 2008, pp. 52-59.

Law et al., "Establishing, maintaining and modifying DNA methylation patterns in plants and animals", Nature Reviews Genetics, vol. 11, No. 3, pp. 204-220, Mar. 1, 2010.

Day et al., "Transgene integration into the same chromosome location can produce alleles that express at a predictable level, or alleles that are differentially silenced", Genes & Development, vol. 14, No. 22, pp. 2869-2880, Nov. 15, 2000.

Butaye, "ISB News Report Approaches to Minimize Variation in Transgene Expression in Plants", Dec. 1, 2005.

Ji et al., "TM6, a novel nuclear matrix attachment region, enhances its flanking gene expression through influencing their chromatin structure", Molecules and Cells, vol. 36, No. 2, pp. 127-137, Jul. 12, 2013.

Forrester et al., "Nuclear matrix attachment regions antagonize methylation-dependent repression of long-range enhancer-promoter interactions", Genes and Development, vol. 13, No. 22, pp. 3003-3014, Nov. 15, 1999.

Brouwer, "Suppression of Transgene Silencing by Matrix Attachment Regions in Maize: A Dual Role for the Maize 5' AHD1 Matrix Attachment Region", The Plant Cell, vol. 14, No. 9, pp. 2251-2264, Aug. 23, 2002.

Kim et al., "Construction of a Z-DNA-Specific Restriction Endonuclease," *PNAS* 94:12875-12879 (1997).

Kim et al., "Hybrid Restriction Enzymes: Zinc Finger Fusions to FOK I Cleavage Domain," *PNAS* 93:1156-1160 (1996).

Kim et al., "Chimeric Restriction Endonuclease," *PNAS* 91:883-887 (1994).

Knutson et al., "Modification of Brassica Seed Oil by Antisense Expression of a Stearoyl-Acyl Carrier Protein Desaturase Gene," *Proc. Natl. Acad. Sci. U.S.A.*, 89:2624-2628 (1992).

Kumar et al., "Controlling Transgene Integration in Plants," *Trends Plant Sci*. 6:155-159 (2001).

Le et al., "Simultaneous Generation and Germline Transmission of Multiple Gene Mutations in Rat Using CRISPR-CAS Systems," *Nature Biotechnology* 31:684-686 (2013).

Lee et al., "The Molecular Basis of Sulfonylurea Herbicide Resistance in Tobacco," *EMBO J*. 7(5):1241 (1988).

Liu et al., "Design of Polydactyl Zinc-Finger Proteins for Unique Addressing Within Complex Genomes," *PNAS USA* 94:5525-5530 (1997).

Makarova et al., "A Putative RNA-Interference-Based Immune System Inprokaryotes: Computational Analysis of the Predicted Enzymatic Machinery, Functional Analogies With Eukaryotic RNAI, and Hypothetical Mechanisms of Actions," *Biol. Direct*. 1:7 (2006).

Makarova et al., "A DNA Repair System Specific for the Thermophilic Archaea and Bacteria Predicted by Genomic Context Analysis," *Nucleic Acids Res*. 30:482-496 (2002).

Mani et al., "Binding of Two Zinc Finger Nuclease Monomers to Two Specific Sites is Required for Effective Double-Strand DNA Cleavage," *Biochem. Biophys. Res. Commun*. 334:1191-1197 (2005).

Martin et al., "Map-Based Cloning of a Protein Kinase Gene Conferring Disease Resistance to Tomato," *Science* 262:1432-1436 (1993).

Miki et al., "Transformation of Brassica Napus Canola Cultivars With *Arabidopsis thaliana* Acetohydroxyacid Synthase Genes and Analysis of Herbicide Resistance," *Theor. Appl. Genet*. 80:449 (1990).

Mindrinos et al., "The *A. thaliana* Disease Resistance Gene RPS2 Encodes a Protein Containing a Nucleotide-Binding Site and Leucine-Rich Repeats," *Cell* 78:1089 (1994).

Moehle et al., "Targeted Gene Addition Into a Specified Location in the Human Genome Using Designed Zinc Finger Nucleases," *Proc. Natl. Acad. Sci. USA* 104(9):3055-3060 (2007).

Nekrasov et al., "Targeted Mutagenesis in the Model Plant Nicotiana Benthamiana Using CAS9 RNA-Guided Endonuclease," *Nature Biotechnology* 31:691-693 (2013).

Pabo et al., "Design and Selection of Novel CYS2HIS2 Zincfinger Proteins," *Ann. Rev. Biochem* 70:313-340 (2001).

Paszkowski et al., "Gene Targeting in Plants," *EMBO J*. 7:4021-4026 (1988).

Pen et al., "Production of Active Bacillus Licheniformis Alpha-Amylase in Tobacco and Its Application in Starch Liquefaction," *BioTechnology* 10:292 (1992).

Przibilla et al., "Site-Specific Mutagenesis of the D1 Subunit of Photosystem II in Wild-Type Chlamydomona," Plant Cell 3:169-174 (1991).

(56) References Cited

OTHER PUBLICATIONS

Puchta et al., "Homologous Recombination in Plant Cells is Enhanced by In Vivo Induction of Double Strand Breaks Into DNA by a Site-Specific Endonuclease," *Nucleic Acid Research* 21:5034-5040 (1993).
Raboy et al., "A Survey of Maize Kernel Mutants for Variation in Phytic Acid," *Maydica* 35:383-390 (1990).
Roberts et al., "Rebase: Restriction Enzymes and Methyltransferases," *Nucleic Acids Res.* 31:418-420 (2003).
Scheffler et al., "Desaturase Multigene Families of Brassica Napus Arose Through Genome Duplication," *TAG* 94(5):583-591 (1997).
Schierholt et al., "Mapping a High Oleic Acid Mutation in Winter Oilseed Rape (*Brassica Napus* L.)" *TAG* 101(5-6):897-901 (2000).
Schierholt et al., "Inheritance of High Oleic Acid Mutations in Winter Oilseed Rape (*Brassica Napus* L.)" *Crop Sci.* 41:1444-1449 (2001).
Schornack et al., "Gene-For-Gene-Mediated Recognition of Nuclear-Targeted AVRBS3-Like Bacterial Effector Proteins," *J. Plant Physiol.* 163(3):256-272 (2006).
Segal, "Custom DNA-Binding Proteins Come of Age: Polydactyl Zinc-Finger Proteins," *Curr. Opin. Biotechnol.* 12:632-637 (2001).
Shan et al., "Targeted Genome Modification of Crop Plants Using a CRISPR-CAS System," *Nature Biotechnology* 31:686-680 (2013).
Shiroza et al., "Sequence Analysis of the *Streptococcus mutans* Fructosyltransferase Gene and Flanking Regions," *J. Bacteriol.* 170(2):810-816.
Shukla et al., "Precise Genome Modification in the Crop Species *Zea mays* Using Zinc-Finger Nucleases," *Nature* 459:437-441 (2009).
Siebert et al., "Efficient Repair of Genomic Double-Strand Breaks by Homologous Recombination Between Directly Repeated Sequences in the Plant Genome," *Plant Cell* 14:1121-1131 (2002).
Smith et al., "A Detailed Study of the Substrate Specificity of a Chimeric Restriction Enzyme," *Nucleic Acids Res.* 27:674-681 (1999).
Smith et al., "Requirements for Double-Strand Cleavage by Chimeric Restriction Enzymes With Zinc Finger DNA-Recognition Domains," *Nucleic Acids Res.* 28:3361-3369 (2000).
Sogaard et al., "Site-Directed Mutagenesis of Histidine 93, Aspartic Acid 180, Glutamic Acid 205, Hisitidine 290, and Aspartic Acid 291 at the Active Site and Tryptophan 279 at the Raw Starch Binding Site in Barley A-Amylase 1," *J. Biol. Chem.* 268:22480 (1993).
Steinmetz et al., "The DNA Sequence of the Gene for the Secreted *Bacillus subtilis* Enzyme Levansucrase and Its Genetic Control Sites," *Mol. Gen. Genet.* 20:220 (1985).
Terada et al., "Efficient Gene Targeting by Homologous Recombination in Rice," *Nat. Biotechnol.* 20(10):1030 (2002).
Terada et al., "Gene Targeting by Homologous Recombination as a Biotechnological Tool for Rice Functional Genomics," *Plant Physiol.* 144(2):846 (2007).
Urnov et al., "Genome Editing With Engineered Zinc Finger Nucleases," *Nature Reviews* 11:636-546(2010).
Urnov et al., "Highly Efficient Endogenous Human Gene Correction Using Designed Zinc-Finger Nucleases," *Nature* 435:646-651 (2005).
Van Hartingsveldt et al., "Cloning, Characterization and Overexpression of the Phytase-Encoding Gene (PHYA) of Aspergillus Niger," *Gene* 127:87-94 (1993).
Wah et al., "Structure of FOKI Has Implications for DNA Cleavage," *PNAS USA* 95:10564-10569 (1998).
Wu et al., "Custom-Designed Zinc Finger Nucleases: What is Next?," *Cell. Mol. Life Sci.* 64:2933-2944 (2007).
Eqyuem et al., "Characterization of Three Loci for Homologous Gene Targeting and Transgene Expression," *Biotechnology and Bioengineering*, vol. 110, No. 8, Aug. 2013.
Akhtar, et al., "Chromatin Position Effects Assayed by Thousands of Reporters Integrated in Parallel," *Cell* 154, 914-927, Aug. 15, 2013.
Tillo et al., "G+C content dominates intrinsic nucleosome occupancy," *BMC Bioinformatics* 2009, 10:442, Dec. 22, 2009, available at http://www.biomedcentral.com/1471-2105/10/442.

Krebs et al., "Keys to Open Chromatin for Transcription Activation: FACT and Asf1," *Molecular Cell* 34, May 29, 2009.
Perez-Pinera et al., "Gene targeting to the ROSA26 locus directed by engineered zinc finger nucleases," *Nucleic Acids Research*, 2011, 1-12.
Sadelain et al., "Safe harbours for the integration of new DNA in the human genome," Nature Reviews | Cancer, vol. 12, Jan. 2012.
Silva et al., "Meganucleases and Other Tools for Targeted Genome Engineering: Perspectives and Challenges for Gene Therapy," *Current Gene Therapy*, 2011, 11, 11-27.
International Search Report, International Application No. PCT/US2014/063728, dated Apr. 29, 2015.
International Search Report, International Application No. PCT/US2014/063739, dated Apr. 8, 2015.
Dufourmantel et al., "Generation of fertile transplastomic soybean," *Plant Mol. Biol.*, 2004, 55(4):479-189.
Yadav et al., "Enhanced viral intergenic region-specific short interfering RNA accumulation and DNA methylation correlates with resistance against a geminivirus," *Mol Plant Microbe Interact.*, 2011, 24(10): 1189-1197.
Song et al., "Genome-wide analysis of DNA methylation in soybean," *Mol Plant*, Epub Aug. 21, 2013, 6(6): 1961-1974.
Sonah et al., "An improved genotyping by sequencing (GBS) approach offering increased versatility and efficiency of SNP discovery and genotyping," *PLoS One*, Epub Jan. 23, 2013, 8(1):e54603.
Schmitz et al., "Epigenome-wide inheritance of cytosine methylation variants in a recombinant inbred population," *Genome Res.*, Epub Jun. 5, 2013, 23(10):1663-74.
Schmutz et al., "Glycine Max Chromosome 4 GLYMAchr_04_Cont2713, Whole Genome Shotgun Sequence," Aug. 29, 2013.
Ainley et al., "Trait Stacking via Targeted Genome Editing," Plant Biotechnol. J. 11(9):1126-1134 (2013).
Beerli et al., Toward Controlling Gene Expression at Will: Specific Regulation of the ERBB-2/HER-2 Promoter by Using Polydactyl Zinc Finger Proteins Constructed From Modular Building Blocks, *PNAS USA* 95(25):14628-14633 (1998).
Beerli et al., "Engineering Polydactyl Zinc-Finger Transcription Factors," Nature Biotechnol. 20:135-141(2002).
Bibikova et al., "Stimulation of Gomologous Recombination Through Targeted Cleavage by Chimeric Nucleases," Mol. Cell. Biol. 21(1):289-297 (2001).
Bibikova et al., "Enhancing Gene Targeting With Designed Zinc Finger Nucleases," Science 300(5620):764 (2003).
Bitinate et al., "Fold Dimerization is Required for DNA Cleavage," *PNAS USA* 95:10570-10575 (1998).
Bonas et al., "Genetic and Structural Characterization of the Avirulence Gene AVRBS3 From Xanthomonas campestris PV. vesicatori," Mol. Gen. Genet. 218:127-136 (1989).
Cai et al., Targeted Transgene Integration in Plant Cells Using Designed Zinc Finger Nucleases, *Plant Mol. Biol.* 69(6):699-709 (2009).
Choo et al., Advances in Zinc Finger Engineering, *Curr. Opin. Struct. Biol.* 10:411-416 (2000).
Curtin et al., "Targeted Mutagenesis of Duplicated Genes in Soybean With Zinc-Finger Nucleases," *Plant Physiology* 156:466-473 (2011).
D'Halluin et al., "Homologous Recombination: A Basis for Targeted Genome Optimization in Crop Species Such as Maize," *Plant Biotechnology Journal* 6(1):93-102.
DeGreef et al., "Evaluation of Herbicide Resistance in Transgenic Crops Under Field Conditions," *Nat Biotechnology* 7:61-64 (1989).
Doyon et al., "Heritable Targeted Gene Disruption in Zebrafish Using Designed Zinc-Finger Nucleases," *Nat. Biotechnol.* 26:702-708 (2008).
Elliott et al., "Isolation and Characterization of Fruit Vacuolar Invertase Genes From Two Tomato Species and Temporal Differences in MRNA Levels During Fruit Ripening," *Plant Molec. Biol.* 21:515-524 (1993).
Fisher et al., Starch Branching Enzyme II From Maize Endosperm, *Plant Physiol.* 102:1045-1046 (1993).

(56) References Cited

OTHER PUBLICATIONS

Geiser et al., "The Hypervariable Region in the Genes Coding for Entomopathogenic Crystal Proteins of Bacillus Thuringiensis: Nucleotide Sequence of the KURHD1 Gene of Subsp. Kurstaki HD1," *Gene* 48:109-118 (1986).
Guerts et al., Knockout Rats Via Embryo Microinjection of Zinc-Finger Nucleases, *Science* 325(5939):433 (2009).
Haft et al., "A Guild of 45 CRISPR-Associated (CAS) Protein Families and Multiple CRISPR/CAS Subtypes Exist in Prokaryotic Genomes," *PLoS Comput. Biol.* 1:e60 (2005) <http://www.jcvi.org/cms/nc/publications/listing/browse/3/article//Haft/#sthash.bXXP6pOi.dpuf>.
Hayes et al., "Molecular Cloning and Heterologous Expression of a CDNA Encoding a Mouse Glutathione S-Transferase YC Subunit Possessing High Catalytic Activity for Aflatoxin B1-8,9-Epoxide," *Biochem. J.* 285:173-180 (1992).
Heuer et al., "Repeat Domain Diversity of AVRBS3-Like Genes in Ralstonia *Solanacearum* Strains and Association With Host Preferences in the Field," *Appl. and Envir. Micro.* 73(13):4379-4384 (2007).
Isalan et al., "A Rapid, Generally Applicable Method to Engineer Zinc Fingers Illustrated by Targeting the HIV-1 Promoter," *Nature Biotechnol.* 19:656-660 (2001).
Jansen et al., "Identification of Genes That Are Associated With DNA Repeats in Prokaryotes," *Mol. Microbiol.* 43:1565-1575 (2002).
Jones et al., "Isolation of the Tomato CF-9 Gene for Resistance to Cladosporium Fulvum by Transposon Tagging," *Science* 266:789-793 (1994).
Kay et al., "A Bacterial Effector Acts as a Plant Transcription Factor and Induces a Cell Size Regulator," *Science* 318:648-651 (2007).
Kim et al., "Chimeric Restriction Enzyme:GAL4 Fusion to FOKL Cleavage Domain," *J. Biol. Chem.* 379:489-495 (1998).
Kim et al., "Getting a Handhold on DNA: Design of Poly-Zinc Finger Proteins With Femtomolar Dissociation Constants," *PNAS USA* 95:2812-2817 (1998).
Kim et al., "Design of TATA Box-Binding Proteinyzinc Finger Fusions for Targeted Regulation of Gene Expression," *PNAS* 94:3616-3620 (1997).
Kim et al., "Site-Specific Cleavage of DNA-RNA Hybrids by Zinc Finger/FOKI Cleavage Domain Fusions," *Gene* 203:43-49 (1997).
Makarova et al., "A Putative RNA-Interference-Based Immune System Inprokaryotes: Computational Analysis of the Predicted Enzymatic Machinery, Functional Analogies With Eukaryotic RNAI, and Hypothetical Mechnisms of Action," *Biol. Direct.* 1:7 (2006).
C. D. Day et al: "Transgene integration into the same chromosome location can produce alleles that express at a predictable level, or alleles that are differentially silenced", Genes & Development, vol. 14, No. 22, Nov. 15, 2000 (Nov. 15, 2000), pp. 2869-2880.
Benjamin Jaffa CR et al: "Methylation of chloroplast DNA does not affect viability and maternal inheritance in tobacco and may provide a strategy towards transgene containment", Plant Cell Reports, Springer, Berlin, DE, vol. 27, No. 8, Jun. 7, 2008 (Jun. 7, 2008), pp. 1377-1384.
Wilson et al: "Sequence Version Archive AC194735", European Nucleotide Archive (ENA), Sep. 24, 2013 (Sep. 24, 2013), XP055339598; Retrieved from the Internet.
Laura Civardi et al: "The Relationship Between Genetic and Physical Distances in the Cloned AI-H2 Interval of the *Zea mays* L. Genome", Proc. Nati. Acad. Sci, Aug. 1, 1994 (Aug. 1, 1994), pp. 8268-8272.
P. S. Schnable et al: "The B73 Maize Genome: Complexity, Diversity, and Dynamics", Science, vol. 326, No. 5956, Nov. 20, 2009 (Nov. 20, 2009), pp. 1112-1115.
Steve R. Eichten et al: "Heritable Epigenetic Variation among Maize Inbreds", PLoS Genetics, vol. 7, No. 11, Nov. 17, 2011 (Nov. 17, 2011), p. e1002372.
Neil A. Youngson et al: "Transgenerational Epigenetic Effects", Annual Review of Genomics and Human Genetics, vol. 9, No. 1, Sep. 1, 2008 (Sep. 1, 2008), pp. 233-257.
Database Nov. 1, 2006, "GM_WBb0017007.r GM_WBb Glycine max genomic clone GM_WBb0017007.3', genomic survey sequence" Accession No. ED683744.
Shin-Ichi Sakamoto et al "Marker-assisted Analysis for Soybean Sequence Repeat Loci HardSeededness with Isozyme and Simple", *Breeding Science*, Jan. 1, 2004, pp. 133-139.
Hyeun-Kyeung Kim et al, "Quantitative Trait Loci Associated with Oliosaccharide and Sucrose Contents in Soybean (*Glycine max* L.) Myoung-Gu Choung3, and Duck", J. Plant Biol. Mar. 1, 2005 pp. 106-112.
Lu Y et al: "Analysis of DNA methylation in different maize tissues", J. of Genetics and Genomics, Elsevier BV, NL, vol. 35, No. 1, Jan. 1, 2008, pp. 41-48.
McCarty et 2005, The Plant Journal 2005 44:p. 52-61.
Eva Bauer et al: "Intraspecific variation of recombination rate in maize", Genome Biology, Biomed Central Ltd., London, GB, vol. 14, No. 9, Sep. 19, 2013, pp. R103.
Database EMBL Nov. 1, 2006 "GM_WBb0017007.rGM_WBb Glycine max genomic clone GM_WBb0017007 3', genomic survey sequence", EBI accession No. EM_GSS:ED683744, Database accession No. ED683744.
Molinier et al, 2006, Nature 442: p. 1046-1049.

* cited by examiner

OPTIMAL SOYBEAN LOCI

CROSS-REFERENCE TO RELATED APPLICATIONS

This application is a continuation of U.S. application Ser. No. 15/867,770, filed on Jan. 11, 2018, now U.S. Pat. No. 10,106,804, which is a continuation of U.S. application Ser. No. 14/531,748, filed on 5 Nov. 3, 2014, now U.S. Pat. No. 9,909,131, and claims the benefit, under 35 U.S.C. § 119(e), to U.S. Provisional Patent Application No. 61/899,602, filed on Nov. 4, 2013, the contents of which are incorporated by reference in their entirety into the present application

REFERENCE TO SEQUENCE LISTING SUBMITTED ELECTRONICALLY

The official copy of the sequence listing is submitted electronically via EFS-Web as an ASCII formatted sequence listing with a file named "282591seqlist.txt", created on Aug. 28, 2018, and having a size of 13.4 megabytes and is filed concurrently with the specification. The sequence listing contained in this ASCII formatted document is part of the specification and is herein incorporated by reference in its entirety.

REFERENCE TO TABLE LISTING SUBMITTED ELECTRONICALLY

The official copy of the table listing is submitted electronically via EFS-Web as a .PDF formatted table listing with a file named "Table 3", created on Aug. 28, 2018, and having a size of 12 megabytes and is filed concurrently with the specification. The table listing contained in this .PDF formatted document is part of the specification and is herein incorporated by reference in its entirety.

BACKGROUND

The genome of numerous types of dicot plants, for example soybean plants, was successfully transformed with transgenes in the early 1990's. Over the last twenty years, numerous methodologies have been developed for transforming the genome of dicot plants, like soybean, wherein a transgene is stably integrated into the genome of dicot plants. This evolution of dicot transformation methodologies has resulted in the capability to successfully introduce a transgene comprising an agronomic trait within the genome of dicot plants, such as soybean. The introduction of insect resistance and herbicide tolerant traits within dicot plants in the late-1990's provided producers with a new and convenient technological innovation for controlling insects and a wide spectrum of weeds, which was unparalleled in cultivation farming methods. Currently, transgenic dicot plants are commercially available throughout the world, and new transgenic products such as Enlist™ Soybean offer improved solutions for ever-increasing weed challenges. The utilization of transgenic dicot plants in modern agronomic practices would not be possible, but for the development and improvement of transformation methodologies.

However, current transformation methodologies rely upon the random insertion of transgenes within the genome of dicot plants, such as soybean. Reliance on random insertion of genes into a genome has several disadvantages. The transgenic events may randomly integrate within gene transcriptional sequences, thereby interrupting the expression of endogenous traits and altering the growth and development of the plant. In addition, the transgenic events may indiscriminately integrate into locations of the genome that are susceptible to gene silencing, culminating in the reduced or complete inhibition of transgene expression either in the first or subsequent generations of transgenic plants. Finally, the random integration of transgenes within the plant genome requires considerable effort and cost in identifying the location of the transgenic event and selecting transgenic events that perform as designed without agronomic impact to the plant. Novel assays must be continually developed to determine the precise location of the integrated transgene for each transgenic event, such as a soybean transgenic event. The random nature of plant transformation methodologies results in a "position-effect" of the integrated transgene, which hinders the effectiveness and efficiency of transformation methodologies.

Targeted genome modification of plants has been a long-standing and elusive goal of both applied and basic research. Targeting genes and gene stacks to specific locations in the genome of dicot plants, such as soybean plants, will improve the quality of transgenic events, reduce costs associated with production of transgenic events and provide new methods for making transgenic plant products such as sequential gene stacking. Overall, targeting trangenes to specific genomic sites is likely to be commercially beneficial. Significant advances have been made in the last few years towards development of methods and compositions to target and cleave genomic DNA by site specific nucleases (e.g., Zinc Finger Nucleases (ZFNs), Meganucleases, Transcription Activator-Like Effector Nucleases (TALENS) and Clustered Regularly Interspaced Short Palindromic Repeats/CRISPR-associated nuclease (CRISPR/Cas) with an engineered crRNA/tracr RNA), to induce targeted mutagenesis, induce targeted deletions of cellular DNA sequences, and facilitate targeted recombination of an exogenous donor DNA polynucleotide within a predetermined genomic locus. See, for example, U.S. Patent Publication No. 20030232410; 20050208489; 20050026157; 20050064474; and 20060188987, and International Patent Publication No. WO 2007/014275, the disclosures of which are incorporated by reference in their entireties for all purposes. U.S. Patent Publication No. 20080182332 describes use of non-canonical zinc finger nucleases (ZFNs) for targeted modification of plant genomes and U.S. Patent Publication No. 20090205083 describes ZFN-mediated targeted modification of a plant EPSPs genomic locus. Current methods for targeted insertion of exogenous DNA typically involve co-transformation of plant tissue with a donor DNA polynucleotide containing at least one transgene and a site specific nuclease (e.g., ZFN) which is designed to bind and cleave a specific genomic locus of an actively transcribed coding sequence. This causes the donor DNA polynucleotide to stably insert within the cleaved genomic locus resulting in targeted gene addition at a specified genomic locus comprising an actively transcribed coding sequence.

An alternative approach is to target the transgene to preselected target nongenic loci within the genome of dicot plants like soybean. In recent years, several technologies have been developed and applied to plant cells for the targeted delivery of a transgene within the genome of dicot plants like soybean. However, much less is known about the attributes of genomic sites that are suitable for targeting. Historically, non-essential genes and pathogen (viral) integration sites in genomes have been used as loci for targeting. The number of such sites in genomes is rather limiting and there is therefore a need for identification and characterization of targetable optimal genomic loci that can be used for targeting of donor polynucleotide sequences. In addition to being amenable to targeting, optimal genomic loci are expected to be neutral sites that can support transgene expression and breeding applications. A need exists for compositions and methods that define criteria to identify optimal nongenic loci within the genome of dicot plants, for example soybean plants, for targeted transgene integration.

SUMMARY

In an embodiment, the subject disclosure relates to a recombinant sequence, comprising: a nucleic acid sequence of at least 1 Kb and having at least 90%, 95%, or 99% sequence identity with a nongenic sequence selected from the group consisting of soy_OGL_1423 (SEQ ID NO:639), soy_OGL_1434 (SEQ ID NO:137), soy_OGL_4625 (SEQ ID NO:76), soy_OGL_6362 (SEQ ID NO:440), soy_OGL_308 (SEQ ID NO:43), soy_OGL_307 (SEQ ID NO:566), soy_OGL_310 (SEQ ID NO:4236), soy_OGL_684 (SEQ ID NO:47), soy_OGL_682 (SEQ ID NO:2101), and soy_OGL_685 (SEQ ID NO:48). In one embodiment, the insertion of the DNA of interest modifies the original sequence of the nongenic loci by alterations of the nongenic loci sequence proximal to the insertion site including for example deletions, inversions, insertions, and duplications of the nongenic loci sequence. In a further aspect, an embodiment relates to a DNA of interest, wherein the DNA of interest is inserted into said nongenic sequence. In another aspect, an embodiment comprises the recombinant sequence, wherein a DNA of interest is inserted proximal to a zinc finger target site. In another aspect, an embodiment comprises the recombinant sequence, wherein a DNA of interest is inserted at a zinc finger target site. In another embodiment, the recombinant sequence comprises an inserted DNA of interest that further comprises an analytical domain. In another embodiment, the recombinant sequence comprises an inserted DNA of interest that does not encode a peptide. In a further embodiment, the recombinant sequence comprises a DNA of interest that encodes a peptide. In yet another embodiment, the recombinant sequence comprises an inserted DNA of interest that further comprises a gene expression cassette. In an embodiment, the gene expressions cassette contains a gene comprising an insecticidal resistance gene, herbicide tolerance gene, nitrogen use efficiency gene, water use efficiency gene, nutritional quality gene, DNA binding gene, and selectable marker gene. In a further embodiment, the recombinant sequence comprises two or more gene expression cassettes. In another embodiment, the recombinant sequence comprises two or more of said nongenic sequences that are located on a same chromosome. In an additional embodiment, the recombinant sequence comprises the DNA of interest and/or the nongenic sequence are modified during insertion of said DNA of interest into the nongenic sequence. In another embodiment, the subject disclosure relates to a soybean plant, soybean plant part, or soybean plant cell comprising a recombinant sequence.

In a further embodiment, the disclosure relates to a method of making a transgenic plant cell comprising a DNA of interest. In another aspect of the disclosure, the method comprises selecting a target nongenic soybean genomic locus having at least 90%, 95%, or 99% sequence identity with a target nongenic soybean genomic locus selected from the group consisting of soy_OGL_1423 (SEQ ID NO:639), soy_OGL_1434 (SEQ ID NO:137), soy_OGL_4625 (SEQ ID NO:76), soy_OGL_6362 (SEQ ID NO:440), soy_OGL_308 (SEQ ID NO:43), soy_OGL_307 (SEQ ID NO:566), soy_OGL_310 (SEQ ID NO:4236), soy_OGL_684 (SEQ ID NO:47), soy_OGL_682 (SEQ ID NO:2101), and soy_OGL_685 (SEQ ID NO:48); selecting a site specific nuclease that specifically binds and cleaves said target nongenic soybean genomic locus; introducing said site specific nuclease into a soybean plant cell; introducing the DNA of interest into the plant cell; inserting the DNA of interest into said target nongenic soybean genomic loci; and, selecting transgenic plant cells comprising the DNA of interest targeted to said nongenic locus. In a further aspect, an embodiment relates to a method of making a transgenic plant cell. In another embodiment, the DNA of interest comprises an analytical domain. In an embodiment, the DNA of interest does not encode a peptide. In yet another embodiment, the DNA of interest encodes a peptide. In a further embodiment, the DNA of interest comprises a gene expression cassette comprising a transgene. In another embodiment, the DNA of interest comprises two or more gene expression cassettes. In a subsequent embodiment, the site specific nuclease is selected from the group consisting of a zinc finger nuclease, a CRISPR nuclease, a TALEN, a homing endonuclease or a meganuclease. In an embodiment, the said DNA of interest is integrated within said nongenic locus via a homology directed repair integration method. In another embodiment, the said DNA of interest is integrated within said nongenic locus via a non-homologous end joining integration method. In a further embodiment, the method of making a transgenic plant cell provides for two or more of said DNA of interest that are inserted into two or more of said target nongenic soybean genomic loci. In another embodiment, the method of making a transgenic plant cell comprises two or more of said target nongenic soybean genomic loci that are located on a same chromosome. In an additional embodiment, the method of making a transgenic plant cell comprises the DNA of interest and/or the nongenic sequence that are modified during insertion of said DNA of interest into the nongenic sequence.

In accordance with one embodiment, a purified soybean polynucleotide loci is disclosed herein, wherein the purified sequence comprises a nongenic sequence of at least 1 Kb. In one embodiment the nongenic sequence is hypomethylated, exemplifies evidence of recombination and is located in proximal location to an expressing genic region in the soybean genome. In one embodiment, the nongenic sequence has a length ranging from about 1 Kb to about 8.4 Kb. In one embodiment, the DNA of interest comprises exogenous DNA sequences, including for example regulatory sequences, restriction cleavage sites, RNA encoding regions or protein encoding regions. In one embodiment, the DNA of interest comprises a gene expression cassette comprising one or more transgenes. In another embodiment, the purified sequence comprises a nongenic sequence having at least 90%, 95%, or 99% sequence identity with a nongenic sequence selected from the group consisting of soy_OGL_1423 (SEQ ID NO:639), soy_OGL_1434 (SEQ ID NO:137), soy_OGL_4625 (SEQ ID NO:76), soy_OGL_6362 (SEQ ID NO:440), soy_OGL_308 (SEQ ID NO:43), soy_OGL_307 (SEQ ID NO:566), soy_OGL_310 (SEQ ID NO:4236), soy_OGL_684 (SEQ ID NO:47), soy_OGL_682 (SEQ ID NO:2101), and soy_OGL_685 (SEQ ID NO:48). In a further embodiment, the purified nongenic soybean genomic loci comprise a DNA of interest, wherein said DNA of interest is inserted into said nongenic sequence. In another aspect, an embodiment comprises the purified nongenic soybean genomic loci, wherein said DNA of interest is inserted proximal to a zinc finger target site. In a different aspect, an embodiment comprises the purified nongenic soybean genomic loci, wherein said DNA of interest is inserted between a pair of zinc finger target sites. In yet another aspect, an embodiment comprises the purified nongenic soybean genomic loci, wherein said DNA of interest comprises an analytical domain. In another aspect, an embodiment comprises the purified nongenic soybean genomic loci, wherein said DNA of interest does not encode a peptide. In a subsequent aspect, an embodiment comprises the purified nongenic soybean genomic loci, wherein said DNA of interest encodes a peptide. In an embodiment, the gene expression cassette contains a gene comprising an insecticidal resistance gene, herbicide tolerance gene, nitrogen use efficiency gene, water use efficiency gene, nutritional quality gene, DNA binding gene, and selectable marker gene. In a subsequent embodiment, the site specific nuclease is selected from the group consisting of a zinc finger nuclease, a CRISPR nuclease, a TALEN, a homing endonuclease or a meganuclease. In an embodiment, the said DNA of interest is integrated within said nongenic sequence via a homology directed repair integration method. In another embodiment, the said DNA of interest is integrated within said nongenic sequence via a non-homologous end joining integration method. In a further embodiment, the DNA of interest comprises two or more gene expression cassettes. In a further embodiment, purified nongenic soybean genomic loci provides for two or more of said DNA of interest that are inserted into two or more of said target nongenic soybean genomic loci. In another embodiment, the purified nongenic soybean genomic loci provides for two or more of said target nongenic soybean genomic loci that are located on a same chromosome. In an additional embodiment, the purified nongenic soybean genomic comprises the DNA of interest and/or the nongenic sequence that are modified during insertion of said DNA of interest into the nongenic sequence. In another embodiment, the DNA of interest is inserted via a homology directed repair or a non-homologous end joining repair mechanism.

In another embodiment, the subject disclosure provides for a plant comprising a recombinant sequence, said recombinant sequence comprising: a nucleic acid sequence having at least 90%, 95%, or 99% sequence identity with a nongenic sequence; and, a DNA of interest, wherein the DNA of interest is inserted into said nongenic sequence. In another embodiment, the nongenic sequence is selected from the group consisting of soy_OGL_1423 (SEQ ID NO:639), soy_OGL_1434 (SEQ ID NO:137), soy_OGL_4625 (SEQ ID NO:76), soy_OGL_6362 (SEQ ID NO:440), soy_OGL_308 (SEQ ID NO:43), soy_OGL_307 (SEQ ID NO:566), soy_OGL_310 (SEQ ID NO:4236), soy_OGL_684 (SEQ ID NO:47), soy_OGL_682 (SEQ ID NO:2101), and soy_OGL_685 (SEQ ID NO:48). In an additional embodiment, the plant comprises two or more of said recombinant sequences. In a further aspect, an embodiment comprises the plant, wherein said recombinant sequences are located on the same chromosome. In another aspect, an embodiment comprises the plant, wherein said DNA of interest is inserted proximal to a zinc finger target site. In a subsequent aspect, an embodiment comprises the plant, wherein said DNA of interest is inserted between a pair of zinc finger target sites. In an embodiment, said DNA of interest comprises an analytical domain. In a further embodiment, said DNA of interest does not encode a peptide. In yet another embodiment, said DNA of interest encodes a peptide. In a subsequent embodiment, said DNA of interest comprises a gene expression cassette comprising an insecticidal resistance gene, herbicide tolerance gene, nitrogen use efficiency gene, water use efficiency gene, nutritional quality gene, DNA binding gene, and selectable marker gene. In another aspect, an embodiment comprises the plant, wherein, said DNA of interest and/or said nongenic sequence are modified during insertion of said DNA of interest into said nongenic sequence.

In another embodiment, the purified sequence comprises a nongenic sequence having at least 90%, 95%, or 99% sequence identity with a nongenic sequence selected from the group consisting of soy_OGL_1423 (SEQ ID NO:639), soy_OGL_1434 (SEQ ID NO:137), soy_OGL_308 (SEQ ID NO:43), soy_OGL_307 (SEQ ID NO:566), soy_OGL_310 (SEQ ID NO:4236), soy_OGL_684 (SEQ ID NO:47), soy_OGL_682 (SEQ ID NO:2101), and soy_OGL_685 (SEQ ID NO:48).

In another embodiment, the purified sequence comprises a nongenic sequence having at least 90%, 95%, or 99% sequence identity with a nongenic sequence selected from the group consisting of soy_OGL_1423 (SEQ ID NO:639), and soy_OGL_1434 (SEQ ID NO:137).

In another embodiment, the purified sequence comprises a nongenic sequence having at least 90%, 95%, or 99% sequence identity with a nongenic sequence selected from the group consisting of soy_OGL_308 (SEQ ID NO:43), soy_OGL_307 (SEQ ID NO:566), and soy_OGL_310 (SEQ ID NO:4236).

In another embodiment, the purified sequence comprises a nongenic sequence having at least 90%, 95%, or 99% sequence identity with a nongenic sequence selected from the group consisting of soy_OGL_684 (SEQ ID NO:47), soy_OGL_682 (SEQ ID NO:2101), and soy_OGL_685 (SEQ ID NO:48).

In another embodiment, the purified sequence comprises a nongenic sequence having at least 90%, 95%, or 99% sequence identity with a nongenic sequence selected from the group consisting of soy_OGL_1423 (SEQ ID NO:639), soy_OGL_1434 (SEQ ID NO:137), soy_OGL_308 (SEQ ID NO:43), soy_OGL_307 (SEQ ID NO:566), and soy_OGL_310 (SEQ ID NO:4236).

In another embodiment, the purified sequence comprises a nongenic sequence having at least 90%, 95%, or 99% sequence identity with a nongenic sequence selected from the group consisting of soy_OGL_308 (SEQ ID NO:43), soy_OGL_307 (SEQ ID NO:566), soy_OGL_310 (SEQ ID NO:4236), soy_OGL_684 (SEQ ID NO:47), soy_OGL_682 (SEQ ID NO:2101), and soy_OGL_685 (SEQ ID NO:48).

In another embodiment, the purified sequence comprises a nongenic sequence having at least 90%, 95%, or 99% sequence identity with a nongenic sequence selected from the group consisting of soy_OGL_4625 (SEQ ID NO:76), soy_OGL_6362 (SEQ ID NO:440), and soy_OGL_308 (SEQ ID NO:43).

BRIEF DESCRIPTION OF THE DRAWINGS

FIG. 15A illustrates a distribution of the polynucleotide sequence lengths of the optimal genomic loci (OGL). FIG. 15B illustrates the distribution of the optimal nongenic maize loci relative to their recombination frequency. FIG. 15C illustrates the distribution of expressed nucleic acid sequences relative to their proximity (log scale) to the optimal genomic loci (OGL).

DETAILED DESCRIPTION

Definitions

Figure 1:
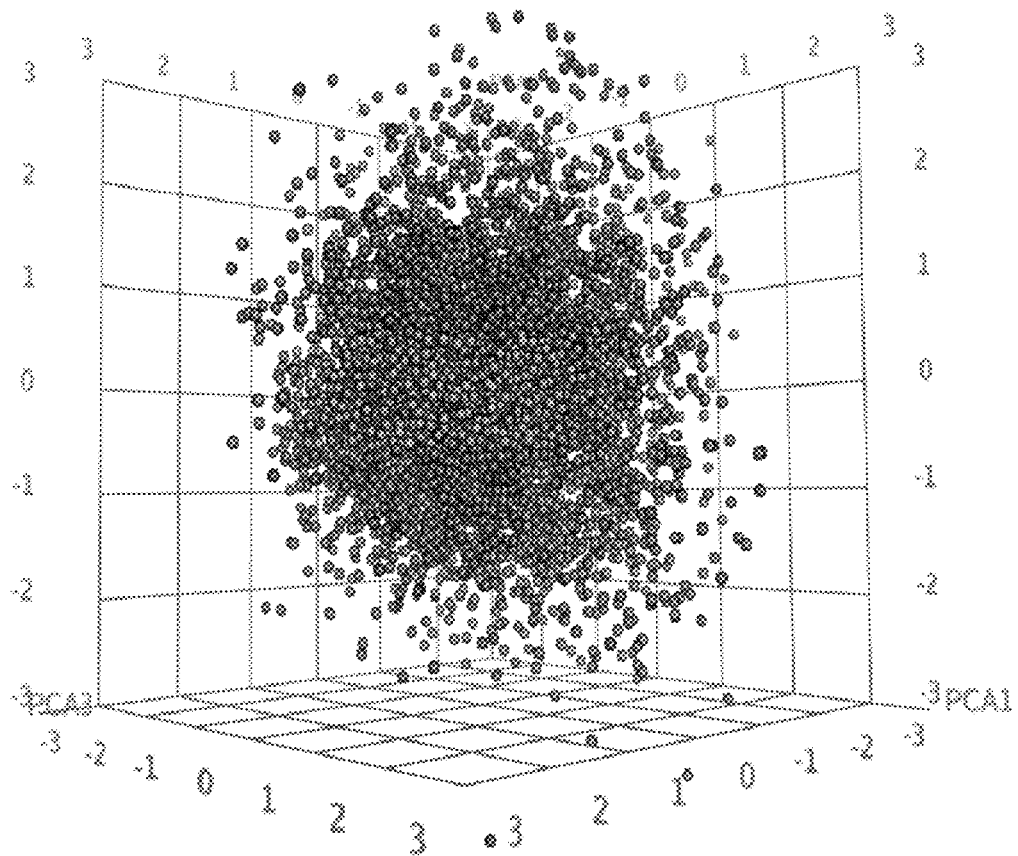
FIG. 1. Represents a three dimensional graph of the 7,018 select genomic loci clustered into 32 clusters. The clusters can be graphed three dimensionally and distinguished by color or other indicators. Each cluster was assigned a unique identifier for ease of visualization, wherein all select genomic loci with the same identifier belonging to the same cluster. After the clustering process, a representative select genomic loci was chosen from each cluster. This was performed by choosing a select genomic loci, within each cluster, that was closest to the centroid of that cluster.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant. Plant cells, as used herein, includes protoplasts and protoplasts with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant part" in embodiments herein. The term "protoplast", as used herein, refers to a plant cell that had its cell wall completely or partially removed, with the lipid bilayer membrane thereof naked. Typically, a protoplast is an isolated plant cell without cell walls which has the potency for regeneration into cell culture or a whole plant.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein, "endogenous sequence" defines the native form of a polynucleotide, gene or polypeptide in its natural location in the organism or in the genome of an organism.

The term "isolated" as used herein means having been removed from its natural environment.

The term "purified", as used herein relates to the isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The terms "polypeptide", "peptide" and "protein" are used interchangeably to refer to a polymer of amino acid residues. The term also applies to amino acid polymers in which one or more amino acids are chemical analogues or modified derivatives of a corresponding naturally-occurring amino acids.

As used herein an "optimal dicot genomic loci", "optimal nongenic dicot loci", "optimal nongenic loci", or "optimal genomic loci (OGL)" is a native DNA sequence found in the nuclear genome of a dicot plant that has the following properties: nongenic, hypomethylated, targetable, and in proximal location to a genic region, wherein the genomic region around the optimal dicot genomic loci exemplifies evidence of recombination.

As used herein an "optimal soybean genomic loci", "optimal nongenic soybean loci", "optimal nongenic loci", or "optimal genomic loci (OGL)" is a native DNA sequence found in the nuclear genome of a dicot plant that has the following properties: nongenic, hypomethylated, targetable, and in proximal location to a genic region, wherein the genomic region around the optimal dicot genomic loci exemplifies evidence of recombination.

As used herein, a "nongenic dicot sequence" or "nongenic dicot genomic sequence" is a native DNA sequence found in the nuclear genome of a dicot plant, having a length of at least 1 Kb, and devoid of any open reading frames, gene sequences, or gene regulatory sequences. Furthermore, the nongenic dicot sequence does not comprise any intron sequence (i.e., introns are excluded from the definition of nongenic). The nongenic sequence cannot be transcribed or translated into protein. Many plant genomes contain nongenic regions. As much as 95% of the genome can be nongenic, and these regions may be comprised of mainly repetitive DNA.

As used herein, a "nongenic soybean sequence" or "nongenic soybean genomic sequence" is a native DNA sequence found in the nuclear genome of a soybean plant, having a length of at least 1 Kb, and devoid of any open reading frames, gene sequences, or gene regulatory sequences. Furthermore, the nongenic soybean sequence does not comprise any intron sequence (i.e., introns are excluded from the definition of nongenic). The nongenic sequence cannot be transcribed or translated into protein. Many plant genomes contain nongenic regions. As much as 95% of the genome can be nongenic, and these regions may be comprised of mainly repetitive DNA.

As used herein, a "genic region" is defined as a polynucleotide sequence that comprises an open reading frame encoding an RNA and/or polypeptide. The genic region may also encompass any identifiable adjacent 5' and 3' non-coding nucleotide sequences involved in the regulation of expression of the open reading frame up to about 2 Kb upstream of the coding region and 1 Kb downstream of the coding region, but possibly further upstream or downstream. A genic region further includes any introns that may be present in the genic region. Further, the genic region may comprise a single gene sequence, or multiple gene sequences interspersed with short spans (less than 1 Kb) of nongenic sequences.

As used herein a "nucleic acid of interest", "DNA of interest", or "donor" is defined as a nucleic acid/DNA sequence that has been selected for site directed, targeted insertion into the dicot genome, like a soybean genome. A nucleic acid of interest can be of any length, for example between 2 and 50,000 nucleotides in length (or any integer value therebetween or thereabove), preferably between about 1,000 and 5,000 nucleotides in length (or any integer value therebetween). A nucleic acid of interest may comprise one or more gene expression cassettes that further comprise actively transcribed and/or translated gene sequences. Conversely, the nucleic acid of interest may comprise a polynucleotide sequence which does not comprise a functional gene expression cassette or an entire gene (e.g., may simply comprise regulatory sequences such as a promoter), or may not contain any identifiable gene expression elements or any actively transcribed gene sequence. The nucleic acid of interest may optionally contain an analytical domain. Upon insertion of the nucleic acid of interest into the dicot genome of soybean for example, the inserted sequences are referred to as the "inserted DNA of interest". Further, the nucleic acid of interest can be DNA or RNA, can be linear or circular, and can be single-stranded or double-stranded. It can be delivered to the cell as naked nucleic acid, as a complex with one or more delivery agents (e.g., liposomes, poloxamers, T-strand encapsulated with proteins, etc.) or contained in a bacterial or viral delivery vehicle, such as, for example, *Agrobacterium tumefaciens* or an adenovirus or an adeno-associated Virus (AAV), respectively.

As used herein the term "analytical domain" defines a nucleic acid sequence that contains functional elements that assist in the targeted insertion of nucleic acid sequences. For example, an analytical domain may contain specifically designed restriction enzyme sites, zinc finger binding sites, engineered landing pads or engineered transgene integration platforms and may or may not comprise gene regulatory elements or an open reading frame. See, for example, U.S. Patent Publication No 20110191899, incorporated herein by reference in its entirety.

As used herein the term "selected dicot sequence" defines a native genomic DNA sequence of a dicot plant that has been chosen for analysis to determine if the sequence qualifies as an optimal nongenic dicot genomic loci.

As used herein the term "selected soybean sequence" defines a native genomic DNA sequence of a soybean plant that has been chosen for analysis to determine if the sequence qualifies as an optimal nongenic soybean genomic loci.

As used herein, the term "hypomethylation" or "hypomethylated", in reference to a DNA sequence, defines a reduced state of methylated DNA nucleotide residues in a given sequence of DNA. Typically, the decreased methylation relates to the number of methylated adenine or cytosine residues, relative to the average level of methylation found in nongenic sequences present in the genome of a dicot plant like a soybean plant.

As used herein a "targetable sequence" is a polynucleotide sequence that is sufficiently unique in a nuclear genome to allow site specific, targeted insertion of a nucleic acid of interest into one specific sequence.

As used herein the term "non-repeating" sequence is defined as a sequence of at least 1 Kb in length that shares less than 40% identity to any other sequence within the genome of a dicot plant, like soybean. Calculations of sequence identity can be determined using any standard technique known to those skilled in the art including, for example, scanning a selected genomic sequence against the dicot genome, e.g., soybean c.v. Williams82 genome, using a BLAST™ based homology search using the NCBI BLAST™+ software (version 2.2.25) run using the default parameter settings (Stephen F. Altschul et al (1997), "Gapped BLAST and PSI-BLAST: a new generation of protein database search programs", Nucleic Acids Res. 25:3389-3402). For example, as the selected soybean sequences (from the *Glycine max* c.v. Williams82 genome) were analyzed, the first BLAST™ hit identified from such a search represents the dicot sequence, e.g., soybean c.v. Williams82 sequence, itself. The second BLAST™ hit for each selected soybean sequence was identified and the alignment coverage (represented as the percent of the selected soybean sequence covered by the BLAST™ hit) of the hit was used as a measure of uniqueness of the selected soybean sequence within the genome of a dicot plant, such as soybean. These alignment coverage values for the second BLAST™ hit ranged from a minimum of 0% to a maximum of 39.97% sequence identity. Any sequences that aligned at higher levels of sequence identity were not considered.

The term "in proximal location to a genic region" when used in reference to a nongenic sequence defines the relative location of the nongenic sequence to a genic region. Specifically, the number of genic regions within a 40 Kb neighborhood (i.e., within 40 Kb on either end of the selected optimal soybean genomic loci sequence) is analyzed. This analysis was completed by assaying gene annotation information and the locations of known genes in the genome of a known dicot, such as soybean, that were extracted from a moncot genome database, for example the Soybean Genome Database. For each of the optimal nongenic soybean genomic loci, e.g., 7,018 optimal nongenic soybean genomic loci, a 40 Kb window around the optimal genomic loci sequence was defined and the number of annotated genes with locations overlapping this window was counted. The number of genic regions ranged from a minimum of 1 gene to a maximum of 18 genes within the 40 Kb neighborhood.

The term "known soybean coding sequence" as used herein relates to any polynucleotide sequence identified from any dicot genomic database, including the Soybean Genomic Database (www.soybase.org, Shoemaker, R. C. et al. *SoyBase, the USDA-ARS soybean genetics and genomics database*. Nucleic Acids Res. 2010 January; 38(Database issue):D843-6.) that comprise an open reading frame, either before or after processing of intron sequences, and are transcribed into mRNA and optionally translated into a protein sequence when placed under the control of the appropriate genetic regulatory elements. The known soybean coding sequence can be a cDNA sequence or a genomic sequence. In some instances, the known soybean coding sequence can be annotated as a functional protein. In other instances, the known soybean coding sequence may not be annotated.

The term "predicted dicot coding sequence" as used herein relates to any Expressed Sequence Tag (EST) polynucleotide sequences described in a dicot genomic database, for example the Soybean Genomic Database. ESTs are identified from cDNA libraries constructed using oligo(dT) primers to direct first-strand synthesis by reverse transcriptase. The resulting ESTs are single-pass sequencing reads of less than 500 bp obtained from either the 5' or 3' end of the cDNA insert. Multiple ESTs may be aligned into a single contig. The identified EST sequences are uploaded into the dicot genomic database, e.g., Soybean Genomic Database and can be searched via bioinformatics methods to predict corresponding genomic polynucleotide sequences that comprise a coding sequence that is transcribed into mRNA and optionally translated into a protein sequence when placed under the control of the appropriate genetic regulatory elements.

The term "predicted soybean coding sequence" as used herein relates to any Expressed Sequence Tag (EST) polynucleotide sequences described in a soybean genomic database, for example the Soybean Genomic Database. ESTs are identified from cDNA libraries constructed using oligo(dT) primers to direct first-strand synthesis by reverse transcriptase. The resulting ESTs are single-pass sequencing reads of less than 500 bp obtained from either the 5' or 3' end of the cDNA insert. Multiple ESTs may be aligned into a single contig. The identified EST sequences are uploaded into the soybean genomic database, e.g., Soybean Genomic Database and can be searched via bioinformatics methods to predict corresponding genomic polynucleotide sequences that comprise a coding sequence that is transcribed into mRNA and optionally translated into a protein sequence when placed under the control of the appropriate genetic regulatory elements.

The term "evidence of recombination" as used herein relates to the meiotic recombination frequencies between any pair of dicot genomic markers, e.g., soybean genomic markers, across a chromosome region comprising the selected soybean sequence. The recombination frequencies were calculated based on the ratio of the genetic distance between markers (in centimorgan (cM)) to the physical distance between the markers (in megabases (Mb)). For a selected soybean sequence to have evidence of recombination, the selected soybean sequence must contain at least one recombination event between two markers flanking the selected soybean sequence as detected using a high resolution marker dataset generated from multiple mapping populations.

As used herein the term "relative location value" is a calculated value defining the distance of a genomic locus from its corresponding chromosomal centromere. For each selected soybean sequence, the genomic distance from the native location of the selected soybean sequence to the centromere of the chromosome that it is located on, is measured (in Bp). The relative location of selected soybean sequence within the chromosome is represented as the ratio of its genomic distance to the centromere relative to the length of the specific chromosomal arm (measured in Bp) that it lies on. These relative location values for the optimal nongenic soybean genomic loci can be generated for different dicot plants, the relative location values for the soybean dataset ranged from a minimum of 0 to a maximum of 0.99682 ratio of genomic distance.

The term "exogenous DNA sequence" as used herein is any nucleic acid sequence that has been removed from its native location and inserted into a new location altering the sequences that flank the nucleic acid sequence that has been moved. For example, an exogenous DNA sequence may comprise a sequence from another species.

"Binding" refers to a sequence-specific, interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant (Kd). "Affinity" refers to the strength of binding: increased binding affinity being correlated with a lower binding constant (Kd).

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

As used herein the term "zinc fingers," defines regions of amino acid sequence within a DNA binding protein binding domain whose structure is stabilized through coordination of a zinc ion.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073, incorporated by reference herein in its entirety.

The CRISPR (Clustered Regularly Interspaced Short Palindromic Repeats)/Cas (CRISPR Associated) nuclease system. Briefly, a "CRISPR DNA binding domain" is a short stranded RNA molecule that acting in concer with the CAS enzyme can selectively recognize, bind, and cleave genomic DNA. The CRISPR/Cas system can be engineered to create a double-stranded break (DSB) at a desired target in a genome, and repair of the DSB can be influenced by the use of repair inhibitors to cause an increase in error prone repair. See, e.g., Jinek et al (2012) Science 337, p. 816-821, Jinek et al, (2013), eLife 2:e00471, and David Segal, (2013) eLife 2:e00563).

Zinc finger, CRISPR and TALE binding domains can be "engineered" to bind to a predetermined nucleotide sequence, for example via engineering (altering one or more amino acids) of the recognition helix region of a naturally occurring zinc finger. Similarly, TALEs can be "engineered" to bind to a predetermined nucleotide sequence, for example by engineering of the amino acids involved in DNA binding (the repeat variable diresidue or RVD region). Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "selected" zinc finger protein, CRISPR or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084 and U.S. Publication Nos. 20110301073, 20110239315 and 20119145940.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the nucleotide sequence that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide. For HR-directed integration, the donor molecule contains at least 2 regions of homology to the genome ("homology arms") of at least 50-100 base pairs in length. See, e.g., U.S. Patent Publication No. 20110281361.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break for HR mediated integration or having no homology to the nucleotide sequence in the region of the break for NHEJ mediated integration, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins, CRISPRS or TALEN can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence (transgene) may produce one or more RNA molecules (e.g., small hairpin RNAs (shRNAs), inhibitory RNAs (RNAis), microRNAs (miRNAs), etc.) or protein.

"Cleavage" as used herein defines the breakage of the phosphate-sugar backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage. A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

A "target site" or "target sequence" refers to a portion of a nucleic acid to which a binding molecule will bind, provided sufficient conditions for binding exist.

Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

A "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, for example, covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

For the purposes of the present disclosure, a "gene", includes a DNA region encoding a gene product (see infra), as well as all DNA regions which regulate the production of the gene product, whether or not such regulatory sequences are adjacent or operably linked to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

Sequence identity: The term "sequence identity" or "identity," as used herein in the context of two nucleic acid or polypeptide sequences, refers to the residues in the two sequences that are the same when aligned for maximum correspondence over a specified comparison window.

As used herein, the term "percentage of sequence identity" refers to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10. The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

Specifically hybridizable/Specifically complementary: As used herein, the terms "specifically hybridizable" and "specifically complementary" are terms that indicate a sufficient degree of complementarity, such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ and/or Mg++ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) Molecular Cloning: A Laboratory Manual, 2nd ed., vol. 1-3, Cold Spring Harbor Laboratory Press, Cold Spring Harbor, N.Y., 1989, chapters 9 and 11; and Hames and Higgins (eds.) Nucleic Acid Hybridization, IRL Press, Oxford, 1985. Further detailed instruction and guidance with regard to the hybridization of nucleic acids may be found, for example, in Tijssen, "Overview of principles of hybridization and the strategy of nucleic acid probe assays," in Laboratory Techniques in Biochemistry and Molecular Biology-Hybridization with Nucleic Acid Probes, Part I, Chapter 2, Elsevier, N Y, 1993; and Ausubel et al., Eds., Current Protocols in Molecular Biology, Chapter 2, Greene Publishing and Wiley-Interscience, N Y, 1995.

As used herein, "stringent conditions" encompass conditions under which hybridization will only occur if there is less than 20% mismatch between the hybridization molecule and a sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize. The following are representative, non-limiting hybridization conditions.

High Stringency condition (detects sequences that share at least 90% sequence identity): Hybridization in 5×SSC buffer (wherein the SSC buffer contains a detergent such as SDS, and additional reagents like salmon sperm DNA, EDTA, etc.) at 65° C. for 16 hours; wash twice in 2×SSC buffer (wherein the SSC buffer contains a detergent such as SDS, and additional reagents like salmon sperm DNA, EDTA, etc.) at room temperature for 15 minutes each; and wash twice in 0.5×SSC buffer (wherein the SSC buffer contains a detergent such as SDS, and additional reagents like salmon sperm DNA, EDTA, etc.) at 65° C. for 20 minutes each.

Moderate Stringency condition (detects sequences that share at least 80% sequence identity): Hybridization in 5x-6×SSC buffer (wherein the SSC buffer contains a detergent such as SDS, and additional reagents like salmon sperm DNA, EDTA, etc.) at 65-70° C. for 16-20 hours; wash twice in 2×SSC buffer (wherein the SSC buffer contains a detergent such as SDS, and additional reagents like salmon sperm DNA, EDTA, etc.) at room temperature for 5-20 minutes each; and wash twice in 1×SSC buffer (wherein the SSC buffer contains a detergent such as SDS, and additional reagents like salmon sperm DNA, EDTA, etc.) at 55-70° C. for 30 minutes each.

Non-stringent control condition (sequences that share at least 50% sequence identity will hybridize): Hybridization in 6×SSC buffer (wherein the SSC buffer contains a detergent such as SDS, and additional reagents like salmon sperm DNA, EDTA, etc.) at room temperature to 55° C. for 16-20 hours; wash at least twice in 2x-3×SSC buffer (wherein the SSC buffer contains a detergent such as SDS, and additional reagents like salmon sperm DNA, EDTA, etc.) at room temperature to 55° C. for 20-30 minutes each.

As used herein, the term "substantially homologous" or "substantial homology," with regard to a contiguous nucleic acid sequence, refers to contiguous nucleotide sequences that hybridize under stringent conditions to the reference nucleic acid sequence. For example, nucleic acid sequences that are substantially homologous to a reference nucleic acid sequence are those nucleic acid sequences that hybridize under stringent conditions (e.g., the Moderate Stringency conditions set forth, supra) to the reference nucleic acid sequence. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

In some instances "homologous" may be used to refer to the relationship of a first gene to a second gene by descent from a common ancestral DNA sequence. In such instances, the term, homolog, indicates a relationship between genes separated by the event of speciation (see ortholog) or to the relationship between genes separated by the event of genetic duplication (see paralog). In other instances "homologous" may be used to refer to the level of sequence identity between one or more polynucleotide sequences, in such instances the one or more polynucleotide sequences do not necessarily descend from a common ancestral DNA sequence. Those with skill in the art are aware of the interchangeably of the term "homologous" and appreciate the proper application of the term.

As used herein, the term "ortholog" (or "orthologous") refers to a gene in two or more species that has evolved from a common ancestral nucleotide sequence, and may retain the same function in the two or more species.

As used herein, the term "paralogous" refers to genes related by duplication within a genome. Orthologs retain the same function in the course of evolution, whereas paralogs evolve new functions, even if these new functions are unrelated to the original gene function.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

When determining the percentage of sequence identity between amino acid sequences, it is well-known by those of skill in the art that the identity of the amino acid in a given position provided by an alignment may differ without affecting desired properties of the polypeptides comprising the aligned sequences. In these instances, the percent sequence identity may be adjusted to account for similarity between conservatively substituted amino acids. These adjustments are well-known and commonly used by those of skill in the art. See, e.g., Myers and Miller (1988) Computer Applications in Biosciences 4:11-7. Statistical methods are known in the art and can be used in analysis of the identified 7,018 optimal genomic loci.

As an embodiment, the identified optimal genomic loci comprising 7,018 individual optimal genomic loci sequences can be analyzed via an F-distribution test. In probability theory and statistics, the F-distribution is a continuous probability distribution. The F-distribution test is a statistical significance test that has an F-distribution, and is used when comparing statistical models that have been fit to a data set, to identify the best-fitting model. An F-distribution is a continuous probability distribution, and is also known as Snedecor's F-distribution or the Fisher-Snedecor distribution. The F-distribution arises frequently as the null distribution of a test statistic, most notably in the analysis of variance. The F-distribution is a right-skewed distribution. The F-distribution is an asymmetric distribution that has a minimum value of 0, but no maximum value. The curve reaches a peak not far to the right of 0, and then gradually approaches the horizontal axis the larger the F value is. The F-distribution approaches, but never quite touches the horizontal axis. It will be appreciated that in other embodiments, variations on this equation, or indeed different equations, may be derived and used by the skilled person and are applicable to the analysis of 7,018 individual optimal genomic loci sequences.

Operably linked: A first nucleotide sequence is "operably linked" with a second nucleotide sequence when the first nucleotide sequence is in a functional relationship with the second nucleotide sequence. For instance, a promoter is operably linked to a coding sequence if the promoter affects the transcription or expression of the coding sequence. When recombinantly produced, operably linked nucleotide sequences are generally contiguous and, where necessary to join two protein-coding regions, in the same reading frame. However, nucleotide sequences need not be contiguous to be operably linked.

The term, "operably linked," when used in reference to a regulatory sequence and a coding sequence, means that the regulatory sequence affects the expression of the linked coding sequence. "Regulatory sequences," "regulatory elements", or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

When used in reference to two or more amino acid sequences, the term "operably linked" means that the first amino acid sequence is in a functional relationship with at least one of the additional amino acid sequences.

The disclosed methods and compositions include fusion proteins comprising a cleavage domain operably linked to a DNA-binding domain (e.g., a ZFP) in which the DNA-binding domain by binding to a sequence in the soybean optimal genomic locus directs the activity of the cleavage domain to the vicinity of the sequence and, hence, induces a double stranded break in the optimal genomic locus. As set forth elsewhere in this disclosure, a zinc finger domain can be engineered to bind to virtually any desired sequence. Accordingly, one or more DNA-binding domains can be engineered to bind to one or more sequences in the optimal genomic locus. Expression of a fusion protein comprising a DNA-binding domain and a cleavage domain in a cell, effects cleavage at or near the target site.

EMBODIMENTS

Targeting transgenes and transgene stacks to specific locations in the genome of dicot plants, like a soybean plant, will improve the quality of transgenic events, reduce costs associated with production of transgenic events and provide new methods for making transgenic plant products such as sequential gene stacking. Overall, targeting trangenes to specific genomic sites is likely to be commercially beneficial. Significant advances have been made in the last few years towards development of site-specific nucleases such as ZFNs, CRISPRs, and TALENs that can facilitate addition of donor polynucleotides to pre-selected sites in plant and other genomes. However, much less is known about the attributes of genomic sites that are suitable for targeting. Historically, non-essential genes and pathogen (viral) integration sites in genomes have been used as loci for targeting. The number of such sites in genomes is rather limiting and there is therefore a need for identification and characterization of optimal genomic loci that can be used for targeting of donor polynucleotide sequences. In addition to being amenable to targeting, optimal genomic loci are expected to be neutral sites that can support transgene expression and breeding applications.

Applicants have recognized that additional criteria are desirable for insertion sites and have combined these criteria to identify and select optimal sites in the dicot genome, like the soybean genome, for the insertion of exogenous sequences. For targeting purposes, the site of selected insertion needs to be unique and in a non-repetitive region of the genome of a dicot plant, like a soybean plant. Likewise, the optimal genomic site for insertion should possess minimal undesirable phenotypic effects and be susceptible to recombination events to facilitate introgression into agronomically elite lines using traditional breeding techniques. In order to identify the genomic loci that meet the listed criteria, the genome of a soybean plant was scanned using a customized bioinformatics approach and genome scale datasets to identify novel genomic loci possessing characteristics that are beneficial for the integration of polynucleotide donor sequence and the subsequent expression of an inserted coding sequence.

I. Identification of Nongenic Soybean Genomic Loci

In accordance with one embodiment a method is provided for identifying optimal nongenic soybean genomic sequence for insertion of exogenous sequences. The method comprises the steps of first identifying soybean genomic sequences of at least 1 Kb in length that are hypomethylated. In one embodiment the hypomethylated genomic sequence is 1, 1.5, 2, 2.5, 3, 3.5, 4, 4.5, 5, 5.5, 6, 6.5, 7, 7.5, 8, 8.5, 9, 10, 11, 12, 13, 14, 15, 16 or 17 Kb in length. In one embodiment the hypomethylated genomic sequence is about 1 to about 5.7 Kb in length and in a further embodiment is about 2 Kb in length. A sequence is considered hypomethylated if it has less than 1% DNA methylation within the sequence. In one embodiment the methylation status is measured based on the presence of 5-methylcytosine at one or more CpG dinucleotides, CHG or CHH trinucleotides within a selected soybean sequence, relative to the amount of total cytosines found at corresponding CpG dinucleotides, CHG or CHH trinucleotides within a normal control DNA sample. More particularly, in one embodiment the selected soybean sequence has less than 1, 2 or 3 methylated nucleotides per 500 nucleotides of the selected soybean sequence. In one embodiment the selected soybean sequence has less than one, two, or three 5-methylcytosines at CpG dinucleotides per 500 nucleotides of the selected soybean sequence.

In one embodiment the selected soybean sequence is 1 to 4 Kb in length and comprises a 1 Kb sequence devoid of 5-methylcytosines. In one embodiment the selected soybean sequence is 1, 1.5, 2, 2.5, 3, 3.5, 4, 4.5, 5, 5.5, or 6, Kb in length and contains 1 or 0 methylated nucleotides in its entire length. In one embodiment the selected soybean sequence is 1, 1.5, 2, 2.5, 3, 3.5, 4, 4.5, 5, 5.5, or 6, Kb in length and contains no 5-methylcytosines at CpG dinucleotides within in its entire length. In accordance with one embodiment the methylation of a selected soybean sequence may vary based on source tissue. In such embodiments the methylation levels used to determine if a sequence is hypomethylated represents the average amount of methylation in the sequences isolated from two or more tissues (e.g., from root and shoot).

In addition to the requirement that an optimal genomic site be hypomethylated, the selected soybean sequence must also be nongenic. Accordingly, all hypomethylated genomic sequences are further screened to eliminate hypomethylated sequences that contain a genic region. This includes any open reading frames regardless of whether the transcript encodes a protein. Hypomethylated genomic sequences that include genic regions, including any identifiable adjacent 5' and 3' non-coding nucleotide sequences involved in the regulation of expression of an open reading frame and any introns that may be present in the genic region, are excluded from the optimal nongenic soybean genomic locus of the present disclosure.

Optimal nongenic soybean genomic loci must also be sequences that have demonstrated evidence of recombination. In one embodiment the selected soybean sequence must contain at least one recombination event between two markers flanking the selected soybean sequence as detected using a high resolution marker dataset generated from multiple mapping populations. In one embodiment the pair of markers flanking a 0.5, 1, 1.5 Mb dicot genomic sequence, such as a soybean genomic sequence, comprising the selected soybean sequence are used to calculate the recombinant frequency for the selected soybean sequence. Recombination frequencies between each pairs of markers (measured in centimorgan (cM)) to the genomic physical distance between the markers (in Mb)) must be greater than 0.0157 cM/Mb. In one embodiment the recombination frequency for a 1 Mb soybean genomic sequence comprising the selected soybean sequence ranges from about 0.01574 cM/Mb to about 83.52 cM/Mb. In one embodiment an optimal genomic loci is one where recombination events have been detected within the selected soybean sequence.

An optimal nongenic soybean genomic loci will also be a targetable sequence, i.e., a sequence that is relatively unique in the soybean genome such that a gene targeted to the selected soybean sequence will only insert in one location of the soybean genome. In one embodiment the entire length of the optimal genomic sequence shares less than 30%, 35%, or 40%, sequence identity with another sequence of similar length contained in the soybean genome. Accordingly, in one embodiment the selected soybean sequence cannot comprise a 1 Kb sequence that share more than 25%, 30%, 35%, or 40% sequence identity with another 1 Kb sequence contained in the soybean genome. In a further embodiment the selected soybean sequence cannot comprise a 500 bp sequence that share more than 30%, 35%, or 40% sequence identity with another 500 bp sequence contained in the soybean genome. In one embodiment the selected soybean sequence cannot comprise a 1 Kb sequence that share more than 40% sequence identity with another 1 Kb sequence contained in the genome of a dicot plant, like a soybean plant.

An optimal nongenic soybean genomic loci will also be proximal to a genic region. More particularly, a selected soybean sequence must be located in the vicinity of a genic region (e.g., a genic region must be located within 40 Kb of genomic sequence flanking and contiguous with either end of the selected soybean as found in the native genome). In one embodiment a genic region is located within 10, 20, 30 or 40 Kb of contiguous genomic sequence located at either end of the selected soybean sequence as found in the native soybean genome. In one embodiment two or more genic regions are located within 10, 20, 30 or 40 Kb of contiguous genomic sequence flanking the two ends of the selected soybean sequence. In one embodiment 1-18 genic regions are located within 10, 20, 30 or 40 Kb of contiguous genomic sequence flanking the two ends of the selected soybean sequence. In one embodiment two or more genic regions are located within a 20, 30 or 40 Kb genomic sequence comprising the selected soybean sequence. In one embodiment 1-18 genic regions are located within a 40 Kb genomic sequence comprising the selected soybean sequence. In one embodiment the genic region located within a 10, 20, 30 or 40 Kb of contiguous genomic sequence flanking the selected soybean sequence comprises a known gene in the genome of a dicot plant, such as a soybean plant.

In accordance with one embodiment a modified nongenic soybean genomic loci is provided wherein the loci is at least 1 Kb in length, is nongenic, comprises no methylated cytosine residues, has a recombination frequency of greater than 0.01574 cM/Mb over a 1 Mb genomic region encompassing the soybean genomic loci and a 1 Kb sequence of the soybean genomic loci shares less than 40% sequence identity with any other 1 Kb sequence contained in the dicot genome, wherein the nongenic soybean genomic loci is modified by the insertion of a DNA of interest into the nongenic soybean genomic loci.

A method for identifying optimal nongenic soybean genomic loci is provided. In some embodiments, the method first comprises screening the dicot genome to create a first pool of selected soybean sequences that have a minimal length of 1 Kb and are hypomethylated, optionally wherein the genomic sequence has less than 1% methylation, optionally wherein the genomic sequence is devoid of any methylated cytosine residues. This first pool of selected soybean sequences can be further screened to eliminate loci that do not meet the requirements for optimal nongenic soybean genomic loci. Dicot genomic sequences, such as those obtained from soybean, that encode dicot transcripts, share greater than 40% or higher sequence identity with another sequence of similar length, do not exhibit evidence of recombination, and do not have a known open reading frame within 40 Kb of the selected soybean sequence, are eliminated from the first pool of sequences, leaving a second pool of sequences that qualify as optimal nongenic soybean loci. In one embodiment any selected soybean sequences that do not have a known dicot gene (i.e., a soybean gene), or a sequence comprising a 2 Kb upstream and/or 1 Kb downstream region of a known dicot gene, within 40 Kb of one end of said nongenic sequence are eliminated from the first pool of sequences. In one embodiment any selected soybean sequences that do not contain a known gene that expresses a protein within 40 Kb of the selected soybean sequence are eliminated. In one embodiment any selected soybean sequences that do not have a recombination frequency of greater than 0.01574 cM/Mb are eliminated.

Using these selection criteria applicants have identified select optimal genomic loci of dicot, such as soybean, that serve as optimal nongenic soybean genomic loci, the sequences of which are disclosed as SEQ ID NO: 1-SEQ ID NO: 7,018. The present disclosure also encompasses natural variants or modified derivatives of the identified optimal nongenic soybean genomic loci wherein the variant or derivative loci comprise a sequence that differs from any sequence of SEQ ID NO: 1-SEQ ID NO: 7,018 by 1, 2, 3, 4, 5, 6, 7, 8, 9 or 10 nucleotides. In one embodiment optimal nongenic soybean genomic loci for use in accordance with the present disclosure comprise sequences selected from SEQ ID NO: 1-SEQ ID NO: 7,018 or sequences that share 90%, 91%, 92%, 93%, 94%, 95%, 96%, 97%, 98% or 99% sequence identity with a sequence selected from SEQ ID NO: 1-SEQ ID NO: 7,018.

In another embodiment, dicot plants for use in accordance with the present disclosure comprise any plant selected from the group consisting of a soybean plant, a canola plant, a rape plant, a *Brassica* plant, a cotton plant, and a sunflower plant. Examples of dicot plants that can be used include, but are not limited to, canola, cotton, potato, quinoa, amaranth, buckwheat, safflower, soybean, sugarbeet, sunflower, canola, rape, tobacco, *Arabidopsis, Brassica*, and cotton.

In another embodiment, optimal nongenic soybean genomic loci for use in accordance with the present disclosure comprise sequences selected from soybean plants. In a further embodiment, optimal nongenic soybean genomic loci for use in accordance with the present disclosure comprise sequences selected from *Glycine max* inbreds. Accordingly, a *Glycine max* inbred includes agronomically elite varieties thereof. In a subsequent embodiment, optimal nongenic soybean genomic loci for use in accordance with the present disclosure comprise sequences selected from transformable soybean lines. In an embodiment, representative transformable soybean lines include; Maverick, Williams82, Merrill JackPeking, Suzuyutaka, Fayette, Enrei, Mikawashima, WaseMidori, Jack, Leculus, Morocco, Serena, Maple prest, Thorne, Bert, Jungery, A3237, Williams, Williams79, AC Colibri, Hefeng 25, Dongnong 42, Hienong 37, Jilin 39, Jiyu 58, A3237, Kentucky Wonder, Minidoka, and derivatives thereof. One of skill in the art will appreciate that as a result of phylogenetic divergence, various types of soybean lines do not contain identical genomic DNA sequences, and that polymorphisms or allelic variation may be present within genomic sequences. In an embodiment, the present disclosure encompasses such polymorphism or allelic variations of the identified optimal nongenic soybean genomic loci wherein the polymorphisms or allelic variation comprise a sequence that differs from any sequence with SEQ ID NO: 1-SEQ ID NO: 7,018 by 1, 2, 3, 4, 5, 6, 7, 8, 9 or 10 nucleotides. In a further embodiment, the present disclosure encompasses such polymorphisms or allelic variations of the identified optimal nongenic soybean genomic loci wherein the sequences comprising the polymorphisms or allelic variation share 90%, 91%, 92%, 93%, 94%, 95%, 96%, 97%, 98% or 99% sequence identity with any sequence of SEQ ID NO: 1-SEQ ID NO: 7,018.

The identified optimal genomic loci comprising 7,018 individual sequences can be categorized into various sub-groupings by further analysis using a multivariate analysis method. Application of any multivariate analysis statistical programs is used to uncover the latent structure (dimensions) of a set of variables. A number of different types of multivariate algorithms can be used, for example the data set can be analyzed using multiple regression analysis, logistic regression analysis, discriminate analysis, multivariate analysis of variance (MANOVA), factor analysis (including both common factor analysis, and principal component analysis), cluster analysis, multidimensional scaling, correspondence analysis, conjoint analysis, canonical analysis, canonical correlation, and structural equation modeling.

In accordance with one embodiment the optimal nongenic soybean genomic loci are further analyzed using multivariate data analysis such as Principal Component Analysis (PCA). Only a brief description will be given here, more information can be found in H. Martens, T. Naes, Multivariate Calibration, Wiley, N.Y., 1989. PCA evaluates the underlying dimensionality (latent variables) of the data, and gives an overview of the dominant patterns and major trends in the data. In one embodiment, the optimal nongenic soybean genomic loci can be sorted into clusters via a principal component analysis (PCA) statistical method. The PCA is a mathematical procedure that uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it be orthogonal to (i.e., uncorrelated with) the preceding components. Principal components are guaranteed to be independent if the data set is jointly normally distributed. PCA is sensitive to the relative scaling of the original variables. Examples of the use of PCA to cluster a set of entities based on features of the entities include; Ciampitti, I. et al., (2012) Crop Science, 52(6); 2728-2742, Chemometrics: A Practical Guide, Kenneth R. Beebe, Randy J. Pell, and Mary Beth Seasholtz, Wiley-Interscience, 1 edition, 1998, U.S. Pat. No. 8,385,662, and European Patent No. 2,340,975.

In accordance with one embodiment a principal component analysis (PCA) was conducted on the 7,018 optimal soybean genomic loci using the following 10 features for each identified optimal soybean genomic loci:

1. Length of the Hypo-Methylated Region Around the Optimal Soybean Genomic Loci (OGL)
    a. DNA methylation profiles of root and shoot tissues isolated from a dicot plant, e.g., *Glycine Max* cultivar Williams82, were constructed using a high throughput whole genome sequencing approach. Extracted DNA was subjected to bisulphite treatment that converts unmethylated cytosines to uracils, but does not affect methylated cytosines, and then sequenced using Illumina HiSeq technology (Krueger, F. et al. DNA methylome analysis using short bisulfite sequencing data. Nature Methods 9, 145-151 (2012)). The raw sequencing reads were mapped to the dicot reference sequence, e.g., *Glycine max* reference sequence, using the Bismark™ mapping software (as described in Krueger F, Andrews S R (2011) Bismark: a flexible aligner and methylation caller for Bisulfite-Seq applications. (Bioinformatics 27: 1571-1572)). The length of the hypo-methylated region around each of the OGLs was calculated using the described methylation profiles.
2. Rate of Recombination in a 1 MB Region Around the OGL
    a. For each OGL, a pair of markers on either side of the OGL, within a 1 Mb window, was identified. Recombination frequencies between each pairs of markers across the chromosome were calculated based on the ratio of the genetic distance between markers (in centimorgan (cM)) to the genomic physical distance between the markers (in Mb).

3. Level of OGLsequence Uniqueness
   a. For each OGL, the nucleotide sequence of the OGL was scanned against the genome of a dicot plant, e.g., soybean c.v. Williams82 genome, using a BLAST based homology search. As these OGL sequences are identified from the genome of a dicot plant, e.g., soybean c.v. Williams82 genome, the first BLAST hit identified through this search represents the OGL sequence itself. The second BLAST hit for each OGL was identified and the alignment coverage of the hit was used as a measure of uniqueness of the OGL sequence within the dicot genome, e.g., soybean genome.

4. Distance from the OGL to the Closest Gene in its Neighborhood
   a. Gene annotation information and the location of known genes in the dicot genome, e.g., soybean c.v. Williams82 genome, were extracted from a known dicot genome database, e.g., Soybean Genome Database (www.soybase.org). For each OGL, the closest annotated gene in its upstream or downstream neighborhood was identified and the distance between the OGL sequence and the gene was measured (in bp).

5. GC % in the OGL Neighborhood
   a. For each OGL, the nucleotide sequence was analyzed to estimate the number of Guanine and Cytosine bases present. This count was represented as a percentage of the sequence length of each OGL and provides a measure for GC %.

6. Number of Genes in a 40 Kb Neighborhood Around the OGL
   a. Gene annotation information and the location of known genes in the dicot genome, e.g., soybean c.v. Williams82 genome, were extracted from a known dicot genomic database, e.g., Soybean Genome Database (www.soybase.org). For each OGL, a 40 Kb window around the OGL was defined and the number of annotated genes with locations overlapping this window was counted.

7. Average Gene Expression in a 40 Kb Neighborhood Around the OGL.
   a. Transcript level expression of dicot genes, e.g., soybean genes, was measured by analyzing transcriptome profiling data generated from dicot plant tissues, e.g., soybean c.v. Williams82 root and shoot tissues, using RNAseq technology. For each OGL, annotated genes within the dicot genome, soybean c.v. Williams82 genome, that were present in a 40 Kb neighborhood around the OGL were identified. Expression levels for each of the genes in the window were extracted from the transcriptome profiles and an average gene expression level was calculated.

8. Level of Nucleosome Occupancy Around the OGL
   a. Discerning the level of nucleosome occupancy for a particular nucleotide sequence provides information about chromosomal functions and the genomic context of the sequence. The NuPoP™ statistical package provides a user-friendly software tool for predicting the nucleosome occupancy and the most probable nucleosome positioning map for genomic sequences of any size (Xi, L., Fondufe-Mittendor, Y., Xia, L., Flatow, J., Widom, J. and Wang, J.-P., Predicting nucleosome positioning using a duration Hidden Markov Model, BMC Bioinformatics, 2010, doi:10.1186/1471-2105-11-346). For each OGL, the nucleotide sequence was submitted to the NuPoP™ software and a nucleosome occupancy score was calculated.

9. Relative Location within the Chromosome (Proximity to Centromere)
   a. Information on position of the centromere in each of the dicot chromosomes, e.g., soybean chromosomes, and the lengths of the chromosome arms was extracted from a dicot genomic database, e.g., Soybean Genome Database (www.soybase.org). For each OGL, the genomic distance from the OGL sequence to the centromere of the chromosome that it is located on, is measured (in bp). The relative location of a OGL within the chromosome is represented as the ratio of its genomic distance to the centromere relative to the length of the specific chromosomal arm that it lies on.

10. Number of OGLs in a 1 Mb Region Around the OGL
    a. For each OGL, a 1 Mb genomic window around the OGL location is defined and the number of OGLs, in the dicot 1 Kb OGL dataset, whose genomic locations overlap with this window is tallied.

The results or values for the score of the features and attributes of each optimal nongenic soybean genomic loci are further described in Table 3 of Example 2. The resulting dataset was used in the PCA statistical method to cluster the 7,018 identified optimal nongenic soybean genomic loci into clusters. During the clustering process, after estimating the "p" principle components of the optimal genomic loci, the assignment of the optimal genomic loci to one of the 32 clusters proceeded in the "p" dimensional Euclidean space. Each of the "p" axes was divided into "k" intervals. Optimal genomic loci assigned to the same interval were grouped together to form clusters. Using this analysis, each PCA axis was divided into two intervals, which was chosen based on a priori information regarding the number of clusters required for experimental validation. All analysis and the visualization of the resulting clusters were carried out with the Molecular Operating Environment™ (MOE) software from Chemical Computing Group Inc. (Montreal, Quebec, Canada). The PCA approach was used to cluster the set of 7,018 optimal soybean genomic loci into 32 distinct clusters based on their feature values, described above.

Figure 2:
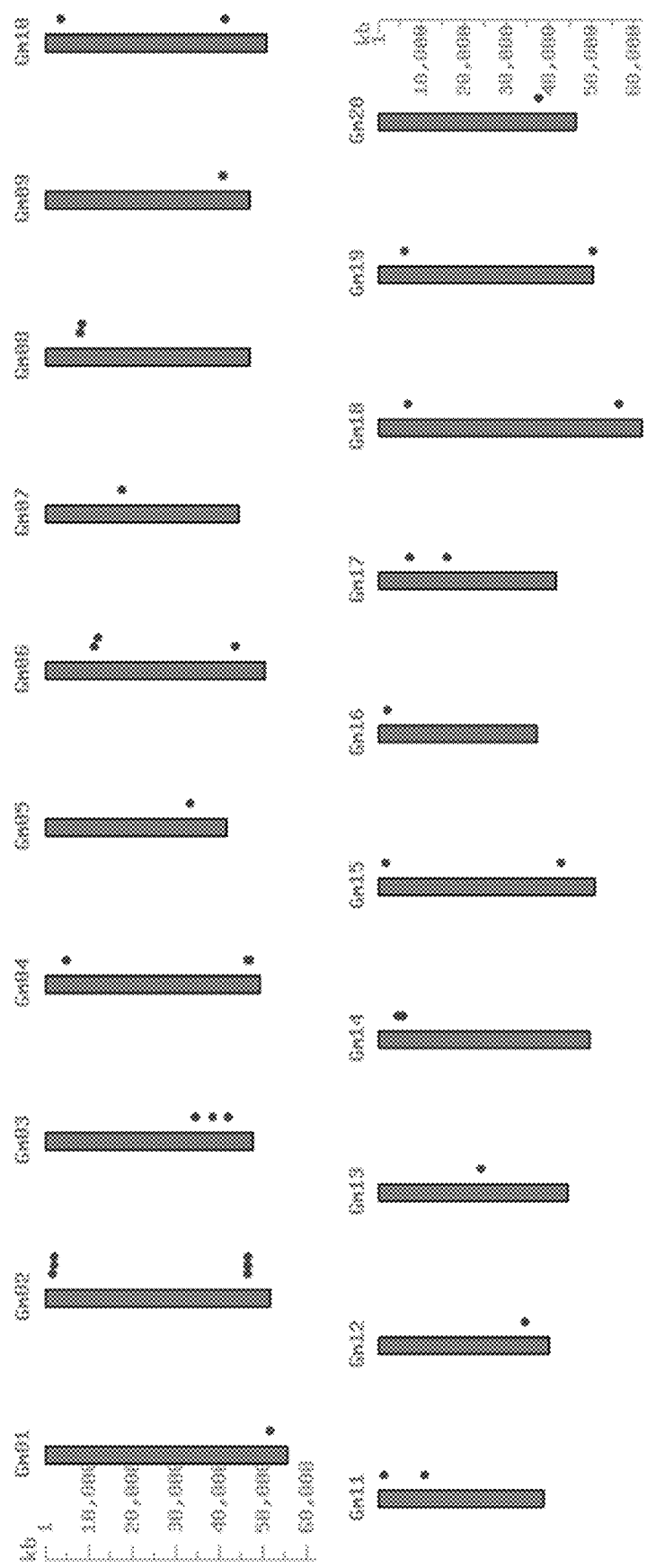
FIG. 2. Provides a schematic drawing indicating the chromosomal distribution of the optimal genomic loci, selected for being closest to the centroid of each of the 32 respective clusters.

During the PCA process, five principal components (PC) were generated, with the top three PCs containing about 90% of the total variation in the dataset (Table 4). These three PCs were used to graphically represent the 32 clusters in a three dimensional plot (see FIG. 1). After the clustering process, was completed, one representative optimal genomic loci was chosen from each cluster. This was performed by choosing a select optimal genomic locus, within each cluster, that was closest to the centroid of that cluster by computational methods (Table 4). The chromosomal locations of the 32 representative optimal genomic loci are uniformly distributed among the soybean chromosomes as shown in FIG. 2.

In accordance with one embodiment a modified optimal nongenic soybean genomic loci is provided wherein the optimal nongenic soybean genomic loci has been modified and comprise one or more nucleotide substitutions, deletions or insertions. In one embodiment the optimal nongenic soybean genomic loci is modified by the insertion of a DNA of interest.

In an embodiment the optimal nongenic soybean genomic loci to be modified is a genomic sequence selected from any sequence described in Table 7 and 8 of Example 7. In one embodiment the optimal nongenic soybean genomic loci to be modified is a genomic sequence selected from soy_OGL_1423 (SEQ ID NO:639), soy_OGL_1434 (SEQ ID NO:137), soy_OGL_4625 (SEQ ID NO:76), soy_OGL_6362 (SEQ ID NO:440), soy_OGL_308 (SEQ ID NO:43), soy_OGL_307 (SEQ ID NO:566), soy_OGL_310 (SEQ ID NO:4236), soy_OGL_684 (SEQ ID NO:47), soy_OGL_682 (SEQ ID NO:2101), and soy_OGL_685 (SEQ ID NO:48). In one embodiment the optimal nongenic soybean genomic loci to be modified is a genomic sequence selected from soy_OGL_1423 (SEQ ID NO:639). In one embodiment the optimal nongenic soybean genomic loci to be modified is a genomic sequence selected from soy_OGL_1434 (SEQ ID NO:137). In one embodiment the optimal nongenic soybean genomic loci to be modified is a genomic sequence selected from soy_OGL_4625 (SEQ ID NO:76). In one embodiment the optimal nongenic soybean genomic loci to be modified is a genomic sequence selected from soy_OGL_6362 (SEQ ID NO:440). In one embodiment the optimal nongenic soybean genomic loci to be modified is a genomic sequence selected from soy_OGL_308 (SEQ ID NO:43). In one embodiment the optimal nongenic soybean genomic loci to be modified is a genomic sequence selected from soy_OGL_307 (SEQ ID NO:566). In one embodiment the optimal nongenic soybean genomic loci to be modified is a genomic sequence selected from soy_OGL_310 (SEQ ID NO:4236). In one embodiment the optimal nongenic soybean genomic loci to be modified is a genomic sequence selected from soy_OGL_684 (SEQ ID NO:47). In one embodiment the optimal nongenic soybean genomic loci to be modified is a genomic sequence selected from soy_OGL_682 (SEQ ID NO:2101). In one embodiment the optimal nongenic soybean genomic loci to be modified is a genomic sequence selected from soy_OGL_685 (SEQ ID NO:48).

In a further embodiment the optimal nongenic soybean genomic loci to be modified is a genomic sequence selected from soy_OGL_1423 (SEQ ID NO:639), soy_OGL_1434 (SEQ ID NO:137), and soy_OGL_4625 (SEQ ID NO:76). In a further embodiment the optimal nongenic soybean genomic loci to be modified is a genomic sequence selected from loci_soy_OGL_6362 (SEQ ID NO:440), and soy_OGL_308 (SEQ ID NO:43). In a further embodiment the optimal nongenic soybean genomic loci to be modified is a genomic sequence selected from soy_OGL_307 (SEQ ID NO:566), soy_OGL_310 (SEQ ID NO:4236), soy_OGL_684 (SEQ ID NO:47), soy_OGL_682 (SEQ ID NO:2101), and soy_OGL_685 (SEQ ID NO:48). In a further embodiment the optimal nongenic soybean genomic loci to be modified is a genomic sequence selected from loci soy_OGL_307 (SEQ ID NO:566), soy_OGL_310 (SEQ ID NO:4236), soy_OGL_684 (SEQ ID NO:47), and soy_OGL_682 (SEQ ID NO:2101). In a further embodiment the optimal nongenic soybean genomic loci to be modified is a genomic sequence selected from loci soy_OGL_307 (SEQ ID NO:566), soy_OGL_310 (SEQ ID NO:4236), and soy_OGL_684 (SEQ ID NO:47). In a further embodiment the optimal nongenic soybean genomic loci to be modified is a genomic sequence selected from loci soy_OGL_307 (SEQ ID NO:566), and soy_OGL_310 (SEQ ID NO:4236). In a further embodiment the optimal nongenic soybean genomic loci to be modified is a genomic sequence selected from loci soy_OGL_310 (SEQ ID NO:4236), soy_OGL_684 (SEQ ID NO:47), soy_OGL_682 (SEQ ID NO:2101), and soy_OGL_685 (SEQ ID NO:48). In a further embodiment the optimal nongenic soybean genomic loci to be modified is a genomic sequence selected from loci soy_OGL_684 (SEQ ID NO:47), soy_OGL_682 (SEQ ID NO:2101), and soy_OGL_685 (SEQ ID NO:48). In a further embodiment the optimal nongenic soybean genomic loci to be modified is a genomic sequence selected from loci soy_OGL_682 (SEQ ID NO:2101), and soy_OGL_685 (SEQ ID NO:48).

In a further embodiment the optimal nongenic soybean genomic loci to be modified is a genomic sequence selected from loci soy_OGL_307 (SEQ ID NO:566), soy_OGL_310 (SEQ ID NO:4236), and soy_OGL_308 (SEQ ID NO:566). In a further embodiment the optimal nongenic soybean genomic loci to be modified is a genomic sequence selected from loci soy_OGL_6362 (SEQ ID NO:440), soy_OGL_4625 (SEQ ID NO:76), and soy_OGL_308 (SEQ ID NO:566). In a further embodiment the optimal nongenic soybean genomic loci to be modified is a genomic sequence selected from loci soy_OGL_1423 (SEQ ID NO:639) and soy_OGL_1434 (SEQ ID NO:137). In a further embodiment the optimal nongenic soybean genomic loci to be modified is a genomic sequence selected from loci soy_OGL_682 (SEQ ID NO:47), soy_OGL_684 (SEQ ID NO:2101), and soy_OGL_85 (SEQ ID NO:48).

In one embodiment the optimal nongenic soybean genomic loci is selected from the genomic sequences of soy_ogl_2474 (SEQ ID NO: 1), soy_ogl_768 (SEQ ID NO: 506), soy_ogl_2063 (SEQ ID NO: 2063), soy_ogl_1906 (SEQ ID NO: 1029), soy_ogl_1112 (SEQ ID NO: 1112), soy_ogl_3574 (SEQ ID NO: 1452), soy_ogl_2581 (SEQ ID NO: 1662), soy_ogl_3481 (SEQ ID NO: 1869), soy_ogl_1016 (SEQ ID NO: 2071), soy_ogl_937 (SEQ ID NO: 2481), soy_ogl_6684 (SEQ ID NO: 2614), soy_ogl_6801 (SEQ ID NO: 2874), soy_ogl_6636 (SEQ ID NO: 2970), soy_ogl_4665 (SEQ ID NO: 3508), soy_ogl_3399 (SEQ ID NO: 3676), soy_ogl_4222 (SEQ ID NO: 3993), soy_ogl_2543 (SEQ ID NO: 4050), soy_ogl_275 (SEQ ID NO: 4106), soy_ogl_598 (SEQ ID NO: 4496), soy_ogl_1894 (SEQ ID NO: 4622), soy_ogl_5454 (SEQ ID NO: 4875), soy_ogl_6838 (SEQ ID NO: 4888), soy_ogl_4779 (SEQ ID NO: 5063), soy_ogl_3333 (SEQ ID NO: 5122), soy_ogl_2546 (SEQ ID NO: 5520), soy_ogl_796 (SEQ ID NO: 5687), soy_ogl_873 (SEQ ID NO: 6087), soy_ogl_5475 (SEQ ID NO: 6321), soy_ogl_2115 (SEQ ID NO: 6520), soy_ogl_2518 (SEQ ID NO: 6574), soy_ogl_5551 (SEQ ID NO: 6775), and soy_ogl_4563 (SEQ ID NO: 6859).

In one embodiment the optimal nongenic soybean genomic loci is selected from the genomic sequences of soy_ogl_308 (SEQ ID NO: 43), soy_ogl_307 (SEQ ID NO: 566), soy_ogl_2063 (SEQ ID NO: 748), soy_ogl_1906 (SEQ ID NO: 1029), soy_ogl_262 (SEQ ID NO: 1376), soy_ogl_5227 (SEQ ID NO: 1461), soy_ogl_4074 (SEQ ID NO: 1867), soy_ogl_3481 (SEQ ID NO: 1869), soy_ogl_1016 (SEQ ID NO: 2071), soy_ogl_937 (SEQ ID NO: 2481), soy_ogl_5109 (SEQ ID NO: 2639), soy_ogl_6801 (SEQ ID NO: 2874), soy_ogl_6636 (SEQ ID NO: 2970), soy_ogl_4665 (SEQ ID NO: 3508), soy_ogl_6189 (SEQ ID NO: 3682), soy_ogl_4222 (SEQ ID NO: 3993), soy_ogl_2543 (SEQ ID NO: 4050), soy_ogl_310 (SEQ ID NO: 4326), soy_ogl_2353 (SEQ ID NO: 4593), soy_ogl_1894 (SEQ ID NO: 4622), soy_ogl_3669 (SEQ ID NO: 4879), soy_ogl_3218 (SEQ ID NO: 4932), soy_ogl_5689 (SEQ ID NO: 5102), soy_ogl_3333 (SEQ ID NO: 5122), soy_ogl_2546 (SEQ ID NO: 5520), soy_ogl_1208 (SEQ ID NO: 5698), soy_ogl_873 (SEQ ID NO: 6087), soy_ogl_5957 (SEQ ID NO: 6515), soy_ogl_4846 (SEQ ID NO: 6571), soy_ogl_3818 (SEQ ID NO: 6586), soy_ogl_5551 (SEQ ID NO: 6775), soy_ogl_7 (SEQ ID NO: 6935), soy_OGL_684 (SEQ ID NO: 47), soy_OGL_682 (SEQ ID NO: 2101), soy_OGL_685 (SEQ ID NO: 48), soy_OGL_1423 (SEQ ID NO: 639), soy_OGL_1434 (SEQ ID NO: 137), soy_OGL_4625 (SEQ ID NO: 76), and soy_OGL_6362 (SEQ ID NO: 440).

In one embodiment the optimal nongenic soybean genomic loci is targeted with a DNA of interest, wherein the DNA of interest integrates within or proximal to the zinc finger nuclease target sites. In accordance with an embodiment, exemplary zinc finger target sites of optimal maize select genomic loci are provided in Table 8. In accordance with an embodiment, integration of a DNA of interest occurs within or proximal to the exemplary target sites of: SEQ ID NO: 7363 and SEQ ID NO: 7364, SEQ ID NO: 7365 and SEQ ID NO: 7366, SEQ ID NO: 7367 and SEQ ID NO: 7368, SEQ ID NO: 7369 and SEQ ID NO: 7370, SEQ ID NO: 7371 and SEQ ID NO: 7372, SEQ ID NO: 7373 and SEQ ID NO: 7374, SEQ ID NO: 7375 and SEQ ID NO: 7376, SEQ ID NO: 7377 and SEQ ID NO: 7378, SEQ ID NO: 7379 and SEQ ID NO: 7380, SEQ ID NO: 7381 and SEQ ID NO: 7382, SEQ ID NO: 7383 and SEQ ID NO: 7384, SEQ ID NO: 7385 and SEQ ID NO: 7386, SEQ ID NO: 7387 and SEQ ID NO: 7388, SEQ ID NO: 7389 and SEQ ID NO: 7390, SEQ ID NO: 7391 and SEQ ID NO: 7392, SEQ ID NO: 7393 and SEQ ID NO: 7394, SEQ ID NO: 7395 and SEQ ID NO: 7396, SEQ ID NO: 7397 and SEQ ID NO: 7398, SEQ ID NO: 7399 and SEQ ID NO: 7400, SEQ ID NO: 7401 and SEQ ID NO: 7402, SEQ ID NO: 7403 and SEQ ID NO: 7404, SEQ ID NO: 7405 and SEQ ID NO: 7406, SEQ ID NO: 7407 and SEQ ID NO: 7408, SEQ ID NO: 7409 and SEQ ID NO: 7410, SEQ ID NO: 7411 and SEQ ID NO: 7412, SEQ ID NO: 7413 and SEQ ID NO: 7414, SEQ ID NO: 7415 and SEQ ID NO: 7416, SEQ ID NO: 7417 and SEQ ID NO: 7418, SEQ ID NO: 7419 and SEQ ID NO: 7420, SEQ ID NO: 7421 and SEQ ID NO: 7422, SEQ ID NO: 7423 and SEQ ID NO: 7424, SEQ ID NO: 7425 and SEQ ID NO: 7426.

In one embodiment the optimal nongenic soybean genomic loci is targeted with a DNA of interest, wherein the DNA of interest integrates within or proximal to the zinc finger nuclease target sites. In accordance with an embodiment, the zinc finger nuclease binds to the zinc finger target site and cleaves the unique soybean genomic polynucleotide target sites, whereupon the DNA of interest integrates within or proximal to the soybean genomic polynucleotide target sites. In an embodiment, integration of the DNA of interest occurs within the zinc finger target site may result with rearrangements. In accordance with one embodiment, the rearrangements may comprise deletions, insertions, inversions, and repeats. In an embodiment, integration of the DNA of interest proximal to the zinc finger target site. According to an aspect of the embodiment, the integration of the DNA is proximal to the zinc finger target site, and may integrate within 1.5 Kb, 1.25 Kb, 1.0 Kb, 0.75 Kb, 0.5 Kb, or 0.25 Kb to the zinc finger target site. Insertion within a genomic region proximal to the zinc finger target site is known in the art, see US Patent Pub No. 2010/0257638 A1 (herein incorporated by reference in its entirety).

In accordance with one embodiment the selected nongenic sequence comprise the following characteristics:

a) the nongenic sequence does not contain greater than 1% DNA methylation within the sequence;

b) the nongenic sequence has a relative location value from 0.211 to 0.976 ratio of genomic distance from a soybean chromosomal centromere;

c) the nongenic sequence has a guanine/cytosine percent content range of 25.62 to 43.76%; and, d) the nongenic sequence is from about 1 Kb to about 4.4 Kb in length.

II. Recombinant Derivatives of Identified Optimal Nongenic Soybean Genomic Loci

In accordance with one embodiment, after having identified a genomic loci of a dicot plant, such as a soybean plant, as a highly desirable location for inserting polynucleotide donor sequences, one or more nucleic acids of interest can be inserted into the identified genomic locus. In one embodiment the nucleic acid of interest comprises exogenous gene sequences or other desirable polynucleotide donor sequences. In another embodiment, after having identified a genomic loci of a dicot plant, such as a soybean plant, as a highly desirable location for inserting polynucleotide donor sequences, one or more nucleic acids of interest or the optimal nongenic soybean genomic loci can optionally be deleted, excised or removed with the subsequent integration of the DNA of interest into the identified genomic locus. In one embodiment the insertion of a nucleic acid of interest into the optimal nongenic soybean genomic loci comprises removal, deletion, or excision of the exogenous gene sequences or other desirable polynucleotide donor sequences.

The present disclosure further relates to methods and compositions for targeted integration into the select soybean genomic locus using ZFNs and a polynucleotide donor construct. The methods for inserting a nucleic acid sequence of interest into the optimal nongenic soybean genomic loci, unless otherwise indicated, use conventional techniques in molecular biology, biochemistry, chromatin structure and analysis, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Methods for Nucleic Acid Insertion into the Soybean Genome

Any of the well known procedures for introducing polynucleotide donor sequences and nuclease sequences as a DNA construct into host cells may be used in accordance with the present disclosure. These include the use of calcium phosphate transfection, polybrene, protoplast fusion, PEG, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular nucleic acid insertion procedure used be capable, of successfully introducing at least one gene into the host cell capable of expressing the protein of choice.

As noted above, DNA constructs may be introduced into the genome of a desired plant species by a variety of conventional techniques. For reviews of such techniques see, for example, Weissbach & Weissbach Methods for Plant Molecular Biology (1988, Academic Press, N.Y.) Section VIII, pp. 421-463; and Grierson & Corey, Plant Molecular Biology (1988, 2d Ed.), Blackie, London, Ch. 7-9. A DNA construct may be introduced directly into the genomic DNA of the plant cell using techniques such as electroporation and microinjection of plant cell protoplasts, by agitation with silicon carbide fibers (See, e.g., U.S. Pat. Nos. 5,302,523 and 5,464,765), or the DNA constructs can be introduced directly to plant tissue using biolistic methods, such as DNA particle bombardment (see, e.g., Klein et al. (1987) Nature 327:70-73). Alternatively, the DNA construct can be introduced into the plant cell via nanoparticle transformation (see, e.g., US Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al. (1984) Science 233:496-498, and Fraley et al. (1983) Proc. Nat'l. Acad. Sci. USA 80:4803.

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) Trends Plant Sci. 11(1):1-4. The virulence functions of the *Agrobacterium tumefaciens* host will direct the insertion of a T-strand containing the construct and adjacent marker into the plant cell DNA when the cell is infected by the bacteria using binary T DNA vector (Bevan (1984) Nuc. Acid Res. 12:8711-8721) or the co-cultivation procedure (Horsch et al. (1985) Science 227:1229-1231). Generally, the *Agrobacterium* transformation system is used to engineer dicotyledonous plants (Bevan et al. (1982) Ann. Rev. Genet. 16:357-384; Rogers et al. (1986) Methods Enzymol. 118:627-641). The *Agrobacterium* transformation system may also be used to transform, as well as transfer, DNA to monocotyledonous plants and plant cells. See U.S. Pat. No. 5,591,616; Hernalsteen et al. (1984) EMBO J. 3:3039-3041; Hooykass-Van Slogteren et al. (1984) Nature 311:763-764; Grimsley et al. (1987) Nature 325:1677-179; Boulton et al. (1989) Plant Mol. Biol. 12:31-40; and Gould et al. (1991) Plant Physiol. 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) EMBO J. 3:2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276) and electroporation of plant tissues (D'Halluin et al. (1992) Plant Cell 4:1495-1505). Additional methods for plant cell transformation include microinjection, silicon carbide mediated DNA uptake (Kaeppler et al. (1990) Plant Cell Reporter 9:415-418), and microprojectile bombardment (see Klein et al. (1988) Proc. Nat. Acad. Sci. USA 85:4305-4309; and Gordon-Kamm et al. (1990) Plant Cell 2:603-618).

In one embodiment a nucleic acid of interest introduced into a host cell for targeted insertion into the genome comprises homologous flanking sequences on one or both ends of the targeted nucleic acid of interest. In such an embodiment, the homologous flanking sequences contain sufficient levels of sequence identity to a dicot genomic sequence, such as a genomic sequence from soybean, to support homologous recombination between it and the genomic sequence to which it bears homology. Approximately 25, 50, 100, 200, 500, 750, 1000, 1500, or 2000 nucleotides, or more of sequence identity, ranging from 70% to 100%, between a donor and a genomic sequence (or any integral value between 10 and 200 nucleotides, or more) will support homologous recombination therebetween.

In another embodiment the targeted nucleic acid of interest lacks homologous flanking sequences, and the targeted nucleic acid of interest shares low to very low levels of sequence identity with a genomic sequence.

In other embodiments of targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present. Double-strand breaks in cellular chromatin can also stimulate cellular mechanisms of non-homologous end joining. In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80, 85, 90, 95, 97.5, to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs.

In certain cases, a non-homologous portion of the donor sequence can contain sequences not present in the region of interest, such that new sequences are introduced into the region of interest. In these instances, the non-homologous sequence is generally flanked by sequences of 50 to 2,000 base pairs (or any integral value therebetween) or any number of base pairs greater than 2,000, that are homologous or identical to sequences in the region of interest. In other embodiments, the donor sequence is non-homologous to the first sequence, and is inserted into the genome by non-homologous recombination mechanisms.

In accordance with one embodiment a zinc finger nuclease (ZFN) is used to introduce a double strand break in a targeted genomic locus to facilitate the insertion of a nucleic acid of interest. Selection of a target site within the selected genomic locus for binding by a zinc finger domain can be accomplished, for example, according to the methods disclosed in U.S. Pat. No. 6,453,242, the disclosure of which is incorporated herein, that also discloses methods for designing zinc finger proteins (ZFPs) to bind to a selected sequence. It will be clear to those skilled in the art that simple visual inspection of a nucleotide sequence can also be used for selection of a target site. Accordingly, any means for target site selection can be used in the methods described herein.

For ZFP DNA-binding domains, target sites are generally composed of a plurality of adjacent target subsites. A target subsite refers to the sequence, usually either a nucleotide triplet or a nucleotide quadruplet which may overlap by one nucleotide with an adjacent quadruplet that is bound by an individual zinc finger. See, for example, WO 02/077227, the disclosure of which is incorporated herein. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also consistent with the subject disclosure.

In accordance with one embodiment, it is not necessary for a target site to be a multiple of three nucleotides. In cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. One nonlimiting example would be a four-finger binding domain that binds to a 13-nucleotide target site comprising, in sequence, two contiguous 3-nucleotide subsites, an intervening nucleotide, and two contiguous triplet subsites.

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; a Tet repressor; LacR; and a steroid hormone receptor.

In some examples, a DNA-binding polypeptide is a zinc finger. Individual zinc finger motifs can be designed to target and bind specifically to any of a large range of DNA sites. Canonical $Cys_2His_2$ (as well as non-canonical $Cys_3His$) zinc finger polypeptides bind DNA by inserting an α-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell. Preferably, the zinc finger protein is non-naturally occurring in that it is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128.

As another alternative, the DNA-binding domain may be derived from a leucine zipper protein. Leucine zippers are a class of proteins that are involved in protein-protein interactions in many eukaryotic regulatory proteins that are important transcription factors associated with gene expression. The leucine zipper refers to a common structural motif shared in these transcriptional factors across several kingdoms including animals, plants, yeasts, etc. The leucine zipper is formed by two polypeptides (homodimer or heterodimer) that bind to specific DNA sequences in a manner where the leucine residues are evenly spaced through an α-helix, such that the leucine residues of the two polypeptides end up on the same face of the helix. The DNA binding specificity of leucine zippers can be utilized in the DNA-binding domains disclosed herein.

In some embodiments, the DNA-binding domain is an engineered domain from a TAL effector derived from the plant pathogen *Xanthomonas* (see, Miller et al. (2011) Nature Biotechnology 29(2):143-8; Boch et al, (2009) Science 29 Oct. 2009 (10.1126/science.117881) and Moscou and Bogdanove, (2009) Science 29 Oct. 2009 (10.1126/science.1178817; and U.S. Patent Publication Nos. 20110239315, 20110145940 and 20110301073).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al (2012) Science 337, p. 816-821, Jinek et al, (2013), eLife 2:e00471, and David Segal, (2013) eLife 2:e00563). Thus, the CRISPR/Cas system can be engineered to create a double-stranded break (DSB) at a desired target in a genome, and repair of the DSB can be influenced by the use of repair inhibitors to cause an increase in error prone repair.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. The Cas protein is deployed in mammalian cells (and putatively within plant cells) by co-expressing the Cas nuclease with guide RNA. Two forms of guide RNAs can be used to facilitate Cas-mediated genome cleavage as disclosed in Le Cong, F., et al., (2013) *Science* 339(6121):819-823.

In other embodiments, the DNA-binding domain may be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease (ZFN). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press, 1993). Non limiting examples of homing endonucleases and meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) Proc. Natl. Acad. Sci. USA 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain. Exemplary Type IIS restriction enzymes are described in International Publication WO 2007/014275, incorporated by reference herein in its entirety.

To enhance cleavage specificity, cleavage domains may also be modified. In certain embodiments, variants of the cleavage half-domain are employed these variants minimize or prevent homodimerization of the cleavage half-domains. Non-limiting examples of such modified cleavage half-domains are described in detail in WO 2007/014275, incorporated by reference in its entirety herein. In certain embodiments, the cleavage domain comprises an engineered cleavage half-domain (also referred to as dimerization domain mutants) that minimize or prevent homodimerization. Such embodiments are known to those of skill the art and described for example in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Additional engineered cleavage half-domains of FokI that form obligate heterodimers can also be used in the ZFNs described herein. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499. In one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey'" mutations (see Guo et al, (2010) J. Mol. Biol. 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055. Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Distance between target sites refers to the number of nucleotides or nucleotide pairs intervening between two target sites as measured from the edges of the sequences nearest each other. In certain embodiments in which cleavage depends on the binding of two zinc finger domain/cleavage half-domain fusion molecules to separate target sites, the two target sites can be on opposite DNA strands. In other embodiments, both target sites are on the same DNA strand. For targeted integration into the optimal genomic locus, one or more ZFPs are engineered to bind a target site at or near the predetermined cleavage site, and a fusion protein comprising the engineered DNA-binding domain and a cleavage domain is expressed in the cell. Upon binding of the zinc finger portion of the fusion protein to the target site, the DNA is cleaved, preferably via a double-stranded break, near the target site by the cleavage domain.

The presence of a double-stranded break in the optimal genomic locus facilitates integration of exogenous sequences via homologous recombination. Thus, in one embodiment the polynucleotide comprising the nucleic acid sequence of interest to be inserted into the targeted genomic locus will include one or more regions of homology with the targeted genomic locus to facilitate homologous recombination.

In addition to the fusion molecules described herein, targeted replacement of a selected genomic sequence also involves the introduction of a donor sequence. The polynucleotide donor sequence can be introduced into the cell prior to, concurrently with, or subsequent to, expression of the fusion protein(s). The donor polynucleotide contains sufficient homology to the optimal genomic locus to support homologous recombination between it and the optimal genomic locus genomic sequence to which it bears homology. Approximately 25, 50, 100, 200, 500, 750, 1,000, 1,500, 2,000 nucleotides or more of sequence homology between a donor and a genomic sequence, or any integral value between 10 and 2,000 nucleotides or more, will support homologous recombination. In certain embodiments, the homology arms are less than 1,000 basepairs in length. In other embodiments, the homology arms are less than 750 base pairs in length. Additionally, donor polynucleotide sequences can comprise a vector molecule containing sequences that are not homologous to the region of interest in cellular chromatin. A donor polynucleotide molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest. The donor polynucleotide can be DNA or RNA, single-stranded or double-stranded and can be introduced into a cell in linear or circular form. See, e.g., U.S. Patent Publication Nos. 20100047805, 20110281361, 20110207221 and U.S. application Ser. No. 13/889,162. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In accordance with one embodiment a method of preparing a transgenic dicot plant, such as a soybean plant, is provided wherein a DNA of interest has been inserted into an optimal nongenic soybean genomic locus. The method comprises the steps of:

a. selecting an optimal nongenic soybean locus as a target for insertion of the nucleic acid of interest;

b. introducing a site specific nuclease into a dicot plant cell, such as a soybean plant cell, wherein the site specific nuclease cleaves the nongenic sequence;

c. introducing the DNA of interest into the plant cell; and d. selecting transgenic plant cells comprising the DNA of interest targeted to said nongenic sequence.

In accordance with one embodiment a method of preparing a transgenic dicot protoplast cell, like a soybean protoplast cell, is provided wherein a DNA of interest has been inserted into an optimal nongenic soybean genomic locus. The method comprises the steps of:

a. selecting an optimal nongenic soybean locus as a target for insertion of the nucleic acid of interest;

b. introducing a site specific nuclease into a dicot protoplast cell, like a soybean protoplast cell, wherein the site specific nuclease cleaves the nongenic sequence;

c. introducing the DNA of interest into the dicot protoplast cell, like a soybean protoplast cell; and d. selecting the transgenic dicot protoplast cell, like a soybean protoplast cell, comprising the DNA of interest targeted to said nongenic sequence.

In one embodiment the site specific nuclease is selected from the group consisting of a Zinc Finger nuclease, a CRISPR nuclease, a TALEN nuclease, or a meganuclease, and more particularly in one embodiment the site specific nuclease is a Zinc Finger nuclease. In accordance with one embodiment the DNA of interest is integrated within said nongenic sequence via a homology directed repair integration method. Alternatively, in some embodiments the DNA of interest is integrated within said nongenic sequence via a non-homologous end joining integration method. In additional embodiments, the DNA of interest is integrated within said nongenic sequence via a previously undescribed integration method. In one embodiment the method comprises selecting a optimal nongenic soybean genomic locus for targeted insertion of a DNA of interest that has the following characteristics:

a. the nongenic sequence is at least 1 Kb in length and does not contain greater than 1% DNA methylation within the sequence b. the nongenic sequence exhibits a 0.01574 to 83.52 cM/Mb rate of recombination within the dicot genome, like a soybean genome;

c. the nongenic sequence exhibits a 0 to 0.494 level of nucleosome occupancy of the dicot genome, like a soybean genome;

d. the nongenic sequence shares less than 40% sequence identity with any other sequence contained in the dicot genome, like a soybean genome;

e. the nongenic sequence has a relative location value from 0 to 0.99682 ratio of genomic distance from a dicot chromosomal centromere, like soybean;

f. the nongenic sequence has a guanine/cytosine percent content range of 14.4 to 45.9%;

g. the nongenic sequence is located proximally to a genic sequence; and, h. a 1 Mb region of dicot genomic sequence, like a soybean genomic sequence, comprising said nongenic sequence comprises one or more additional nongenic sequences. In one embodiment the optimal nongenic soybean locus is selected from a loci of cluster 1, 2, 3, 4, 5, 6, 7, 8, 9, 10, 11, 2, 3, 4, 5, 6, 7, 8, 9, 20, 21, 22, 23, 24, 25, 26, 27, 28, 29, 30, 31 or 32.

Delivery

The donor molecules disclosed herein are integrated into a genome of a cell via targeted, homology-independent and/or homology-dependent methods. For such targeted integration, the genome is cleaved at a desired location (or locations) using a nuclease, for example, a fusion between a DNA-binding domain (e.g., zinc finger binding domain, CRISPR or TAL effector domain is engineered to bind a target site at or near the predetermined cleavage site) and nuclease domain (e.g., cleavage domain or cleavage half-domain). In certain embodiments, two fusion proteins, each comprising a DNA-binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two DNA-binding domains. One or both of the DNA-binding domains can be engineered. See, also, U.S. Pat. No. 7,888,121; U.S. Patent Publication 20050064474 and International Patent Publications WO05/084190, WO05/014791 and WO 03/080809.

The nucleases as described herein can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

Following the introduction of a double-stranded break in the region of interest, the transgene is integrated into the region of interest in a targeted manner via non-homology dependent methods (e.g., non-homologous end joining (NHEJ)) following linearization of a double-stranded donor molecule as described herein. The double-stranded donor is preferably linearized in vivo with a nuclease, for example one or more of the same or different nucleases that are used to introduce the double-stranded break in the genome. Synchronized cleavage of the chromosome and the donor in the cell may limit donor DNA degradation (as compared to linearization of the donor molecule prior to introduction into the cell). The nuclease target sites used for linearization of the donor preferably do not disrupt the transgene(s) sequence(s).

The transgene may be integrated into the genome in the direction expected by simple ligation of the nuclease overhangs (designated "forward" or "AB" orientation) or in the alternate direction (designated "reverse" or "BA" orientation). In certain embodiments, the transgene is integrated following accurate ligation of the donor and chromosome overhangs. In other embodiments, integration of the transgene in either the BA or AB orientation results in deletion of several nucleotides.

Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more donor polynucleotide acid sequences in the genome of the transgenic plant.

The delivery of nucleic acids may be introduced into a plant cell in embodiments of the invention by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by Agrobacterium-mediated transformation (See, e.g., U.S. Pat. Nos. 5,563,055, 5,591,616, 5,693,512, 5,824,877, 5,981,840, and 6,384,301), by acceleration of DNA-coated particles (See, e.g., U.S. Pat. Nos. 5,015,580, 5,550,318, 5,538,880, 6,160,208, 6,399,861, and 6,403,865) and by Nanoparticles, nanocarriers and cell penetrating peptides (WO201126644A2; WO2009046384A1; WO2008148223A1) in the methods to deliver DNA, RNA, Peptides and/or proteins or combinations of nucleic acids and peptides into plant cells.

The most widely-utilized method for introducing an expression vector into plants is based on the natural transformation system of Agrobacterium. A. tumefaciens and A. rhizogenes are plant pathogenic soil bacteria that genetically transform plant cells. The $T_i$ and $R_i$ plasmids of A. tumefaciens and A. rhizogenes, respectively, carry genes responsible for genetic transformation of the plant. The $T_i$ (tumor-inducing)-plasmids contain a large segment, known as T-DNA, which is transferred to transformed plants. Another segment of the $T_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the invention.

Thus, in some embodiments, a plant transformation vector is derived from a $T_i$ plasmid of A. tumefaciens (See, e.g., U.S. Pat. Nos. 4,536,475, 4,693,977, 4,886,937, and 5,501,967; and European Patent EP 0 122 791) or a $R_i$ plasmid of A. rhizogenes. Additional plant transformation vectors include, for example and without limitation, those described by Herrera-Estrella et al. (1983) Nature 303:209-13; Bevan et al. (1983), supra; Klee et al. (1985) Bio/Technol. 3:637-42; and in European Patent EP 0 120 516, and those derived from any of the foregoing. Other bacteria, such as Sinorhizobium, Rhizobium, and Mesorhizobium, that naturally interact with plants can be modified to mediate gene transfer to a number of diverse plants. These plant-associated symbiotic bacteria can be made competent for gene transfer by acquisition of both a disarmed $T_i$ plasmid and a suitable binary vector.

The Nucleic Acid of Interest

The polynucleotide donor sequences for targeted insertion into a genomic locus of a dicot plant, like a soybean plant, typically range in length from about 10 to about 5,000 nucleotides. However, nucleotides substantially longer, up to 20,000 nucleotides can be used, including sequences of about 5, 6, 7, 8, 9, 10, 11 and 12 Kb in length. Additionally, donor sequences can comprise a vector molecule containing sequences that are not homologous to the replaced region. In one embodiment the nucleic acid of interest will include one or more regions that share homology with the targeted genomic loci. Generally, the homologous region(s) of the nucleic acid sequence of interest will have at least 50% sequence identity to a genomic sequence with which recombination is desired. In certain embodiments, the homologous region(s) of the nucleic acid of interest shares 60%, 70%, 80%, 90%, 95%, 98%, 99%, or 99.9% sequence identity with sequences located in the targeted genomic locus. However, any value between 1% and 100% sequence identity can be present, depending upon the length of the nucleic acid of interest.

A nucleic acid of interest can contain several, discontinuous regions of sequence sharing relatively high sequence identity to cellular chromatin. For example, for targeted insertion of sequences not normally present in a targeted genomic locus, the unique sequences can be present in a donor nucleic acid molecule and flanked by regions of sequences that share a relatively high sequence identity to a sequence present in the targeted genomic locus.

A nucleic acid of interest can also be inserted into a targeted genomic locus to serve as a reservoir for later use. For example, a first nucleic acid sequence comprising sequences homologous to a nongenic region of the genome of a dicot plant, like a soybean plant, but containing a nucleic acid of interest (optionally encoding a ZFN under the control of an inducible promoter), may be inserted in a targeted genomic locus. Next, a second nucleic acid sequence is introduced into the cell to induce the insertion of a DNA of interest into an optimal nongenic genomic locus of a dicot plant, like a soybean plant. Either the first nucleic acid sequence comprises a ZFN specific to the optimal nongenic soybean genomic locus and the second nucleic acid sequence comprises the DNA sequence of interest, or vice versa. In one embodiment the ZFN will cleave both the optimal nongenic soybean genomic locus and the nucleic acid of interest. The resulting double stranded break in the genome can then become the integration site for the nucleic acid of interest released from the optimal genomic locus. Alternatively, expression of a ZFN already located in the genome can be induced after introduction of the DNA of interest to induce a double stranded break in the genome that can then become the integration site for the introduced nucleic acid of interest. In this way, the efficiency of targeted integration of a DNA of interest at any region of interest may be improved since the method does not rely on simultaneous uptake of both the nucleic acids encoding the ZFNs and the DNA of interest.

A nucleic acid of interest can also be inserted into an optimal nongenic soybean genomic locus to serve as a target site for subsequent insertions. For example, a nucleic acid of interest comprised of DNA sequences that contain recognition sites for additional ZFN designs may be inserted into the locus. Subsequently, additional ZFN designs may be generated and expressed in cells such that the original nucleic acid of interest is cleaved and modified by repair or homologous recombination. In this way, reiterative integrations of nucleic acid of interests may occur at the optimal nongenic genomic locus of a dicot plant, like a soybean plant.

Exemplary exogenous sequences that can be inserted into an optimal nongenic soybean genomic locus include, but are not limited to, any polypeptide coding sequence (e.g., cDNAs), promoter, enhancer and other regulatory sequences (e.g., interfering RNA sequences, shRNA expression cassettes, epitope tags, marker genes, cleavage enzyme recognition sites and various types of expression constructs. Such sequences can be readily obtained using standard molecular biological techniques (cloning, synthesis, etc.) and/or are commercially available.

To express ZFNs, sequences encoding the fusion proteins are typically subcloned into an expression vector that contains a promoter to direct transcription. Suitable prokaryotic and eukaryotic promoters are well known in the art and described, e.g., in Sambrook et al., Molecular Cloning, A Laboratory Manual (2nd ed. 1989; 3.sup.rd ed., 2001); Kriegler, Gene Transfer and Expression: A Laboratory Manual (1990); and Current Protocols in Molecular Biology (Ausubel et al., supra. Bacterial expression systems for expressing the ZFNs are available in, e.g., E. coli, Bacillus sp., and Salmonella (Palva et al., Gene 22:229-235 (1983)). Kits for such expression systems are commercially available. Eukaryotic expression systems for mammalian cells, yeast, and insect cells are well known by those of skill in the art and are also commercially available.

The particular expression vector used to transport the genetic material into the cell is selected with regard to the intended use of the fusion proteins, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014791 and WO03/080809.

Standard transfection methods can be used to produce bacterial, mammalian, yeast or insect cell lines that express large quantities of protein, which can then be purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds., 1983).

The disclosed methods and compositions can be used to insert polynucleotide donor sequences into a predetermined location such as one of the optimal nongenic soybean genomic loci. This is useful inasmuch as expression of an introduced transgene into the soybean genome depends critically on its integration site. Accordingly, genes encoding herbicide tolerance, insect resistance, nutrients, antibiotics or therapeutic molecules can be inserted, by targeted recombination.

In one embodiment the nucleic acid of interest is combined or "stacked" with gene encoding sequences that provide additional resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical or other uses. The "stacking" of two or more nucleic acid sequences of interest within a plant genome can be accomplished, for example, via conventional plant breeding using two or more events, transformation of a plant with a construct which contains the sequences of interest, re-transformation of a transgenic plant, or addition of new traits through targeted integration via homologous recombination.

Such polynucleotide donor nucleotide sequences of interest include, but are not limited to, those examples provided below:

1. Genes or Coding Sequence (e.g. iRNA) that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium fulvum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al. (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyubiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a soybean calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 Plant Sci. 89:43) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al. (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).

(R) A developmental-arrestive protein produced in nature by a plant, such as the barley ribosome-inactivating gene that provides an increased resistance to fungal disease (Longemann et al., 1992). Bio/Technology 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

2. Genes that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for mutant acetolactate synthase (ALS) (Lee et al., 1988 EMBOJ. 7:1241) also known as acetohydroxyacid synthase (AHAS) enzyme (Miki et al., 1990 Theor. Appl. Genet. 80:449).

(B) One or more additional genes encoding resistance or tolerance to glyphosate imparted by mutant EPSP synthase and aroA genes, or through metabolic inactivation by genes such as DGT-28, 2mEPSPS, GAT (glyphosate acetyltransferase) or GOX (glyphosate oxidase) and other phosphono compounds such as glufosinate (pat, bar, and dsm-2 genes), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione 5-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for soybean, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2phenyl)propane-1,3-dione, triketones (EP625505, EP625508, U.S. Pat. No. 5,506, 195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

3. Genes that Confer or Contribute to a Value-Added Trait (A) Modified fatty acid metabolism, for example, by transforming soybean or Brassica with an antisense gene or stearoyl-ACP desaturase to increase stearic acid content of the plant (Knultzon et al., 1992) Proc. Nat. Acad. Sci. USA 89:2624.

(B) Decreased Phytate Content (1) Introduction of a phytase-encoding gene, such as the *Aspergillus niger* phytase gene (Van Hartingsveldt et al., 1993 Gene 127:87), enhances breakdown of phytate, adding more free phosphate to the transformed plant.

(2) A gene could be introduced that reduces phytate content. In dicots, this, for example, could be accomplished by cloning and then reintroducing DNA associated with the single allele which is responsible for soybean mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, *Streptococcus* mucus fructosyltransferase gene (Shiroza et al., 1988) J. Bacteriol. 170:810, *Bacillus subtilis* levansucrase gene (Steinmetz et al., 1985 Mol. Gen. Genel. 200:220), *Bacillus licheniformis* α-amylase (Pen et al., 1992 Bio/Technology 10:292), tomato invertase genes (Elliot et al., 1993), barley amylase gene (Sogaard et al., 1993 J. Biol. Chem. 268:22480), and soybean endosperm starch branching enzyme II (Fisher et al., 1993 Plant Physiol. 102:10450).

III. Recombinant Constructs

As disclosed herein the present disclosure provides recombinant genomic sequences comprising an optimal nongenic soybean genomic sequence of at least 1 Kb and a DNA of interest, wherein the inserted DNA of interest is inserted into said nongenic sequence. In one embodiment the DNA of interest is an analytical domain, a gene or coding sequence (e.g. iRNA) that confers resistance to pests or disease, genes that confer resistance to a herbicide or genes that confer or contribute to a value-added trait, and the optimal nongenic soybean genomic sequence comprises the following characteristics:

a. the nongenic sequence is about 1 Kb to about 5.7 Kb in length and does not contain a methylated polynucleotide;

b. the nongenic sequence exhibits a 0.01574 to 83.52 cM/Mb rate of recombination within the genome of a dicot plant, like a soybean plant;

c. the nongenic sequence exhibits a 0 to 0.494 level of nucleosome occupancy of the dicot genome, like a soybean genome;

d. the nongenic sequence shares less than 40% sequence identity with any other sequence contained in the dicot genome, like a soybean genome;

e. the nongenic sequence has a relative location value from 0 to 0.99682 ratio of genomic distance from a dicot chromosomal centromere, like a soybean chromosomal center;

f. the nongenic sequence has a guanine/cytosine percent content range of 14.4 to 45.9%;

g. the nongenic sequence is located proximally to an genic sequence, comprising a known or predicted dicot coding sequence, such as a soybean coding sequence, within 40 Kb of contiguous genomic DNA comprising the native nongenic sequence; and, h. the nongenic sequence is located in a 1 Mb region of dicot genomic sequence, such as a genomic sequence, that comprises at least a second nongenic sequence.

In one embodiment the optimal nongenic soybean genomic sequence is further characterized as having a genic region comprisings 1 to 18 known or predicted soybean coding sequence within 40 Kb of contiguous genomic DNA comprising the native nongenic sequence. In one embodiment the optimal nongenic soybean locus is selected from a loci of cluster 1, 2, 3, 4, 5, 6, 7, 8, 9, 10, 11, 2, 3, 4, 5, 6, 7, 8, 9, 20, 21, 22, 23, 24, 25, 26, 27, 28, 29, 30, 31 or 32.

IV. Transgenic Plants

Transgenic plants comprising the recombinant optimal nongenic soybean loci are also provided in accordance with one embodiment of the present disclosure. Such transgenic plants can be prepared using techniques known to those skilled in the art.

A transformed dicot cell, callus, tissue or plant (i.e., a soybean cell, callus, tissue or plant) may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the yellow fluorescence protein, green fluorescence protein, red fluorescence protein, beta-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, Northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-12 (aryloxyalkanoate dioxygenase; see WO 2011/066360) and PAT (phosphinothricin-N-acetyl-transferase (PAT)) proteins using an ELISA assay is described in U.S. Patent Publication No. 20090093366 which is herein incorporated by reference in its entirety. The transgene may be selectively expressed in some tissues of the plant or at some developmental stages, or the transgene may be expressed in substantially all plant tissues, substantially along its entire life cycle. However, any combinatorial expression mode is also applicable.

One of skill in the art will recognize that after the exogenous polynucleotide donor sequence is stably incorporated in transgenic plants and confirmed to be operable, it can be introduced into other plants by sexual crossing. Any of a number of standard breeding techniques can be used, depending upon the species to be crossed.

The present disclosure also encompasses seeds of the transgenic plants described above wherein the seed has the transgene or gene construct. The present disclosure further encompasses the progeny, clones, cell lines or cells of the transgenic plants described above wherein the progeny, clone, cell line or cell has the transgene or gene construct.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in Handbook of Plant Cell Culture, pp. 124-176, Macmillian Publishing Company, New York, 1983; and Binding, Regeneration of Plants, Plant Protoplasts, pp. 21-73, CRC Press, Boca Raton, 1985. Regeneration can also be obtained from plant callus, explants, organs, pollens, embryos or parts thereof. Such regeneration techniques are described generally in Klee et al. (1987) Ann. Rev. of Plant Phys. 38:467-486.

A transgenic plant or plant material comprising a nucleotide sequence encoding a polypeptide may in some embodiments exhibit one or more of the following characteristics: expression of the polypeptide in a cell of the plant; expression of a portion of the polypeptide in a plastid of a cell of the plant; import of the polypeptide from the cytosol of a cell of the plant into a plastid of the cell; plastid-specific expression of the polypeptide in a cell of the plant; and/or localization of the polypeptide in a cell of the plant. Such a plant may additionally have one or more desirable traits other than expression of the encoded polypeptide. Such traits may include, for example: resistance to insects, other pests, and disease-causing agents; tolerances to herbicides; enhanced stability, yield, or shelf-life; environmental tolerances; pharmaceutical production; industrial product production; and nutritional enhancements.

In accordance with one embodiment a transgenic dicot protoplast (i.e., a soybean protoplast) is provided comprising a recombinant optimal nongenic soybean locus. More particularly, a dicot protoplast, such as a soybean protoplast, is provided comprising a DNA of interest inserted into an optimal nongenic soybean genomic loci of the dicot protoplast (i.e, a soybean protoplast), wherein said nongenic soybean genomic loci is about 1 Kb to about 5.7 Kb in length and lacks any methylated nucleotides. In one embodiment the transgenic dicot protoplast (i.e., a transgenic soybean protoplat), comprises a DNA of interest inserted into the optimal nongenic soybean genomic locus wherein the DNA of interest comprises an analytical domain, and/or an open reading frame. In one embodiment the inserted DNA of interest encodes a peptide and in a further embodiment the DNA of interest comprises at least one gene expression cassette comprising a transgene.

In accordance with one embodiment a transgenic dicot plant, dicot plant part, or dicot plant cell (i.e., a transgenic soybean plant, soybean plant part, or soybean plant cell) is provided comprising a recombinant optimal nongenic soybean locus. More particularly, a dicot plant, dicot plant part, or dicot plant cell (i.e., a soybean plant, soybean plant part, or soybean plant cell) is provided comprising a DNA of interest inserted into an optimal nongenic soybean genomic loci of the dicot plant, dicot plant part, or dicot plant cell (i.e., a soybean plant, soybean plant part, or soybean plant cell), wherein said nongenic soybean genomic loci is about 1 Kb to about 5.7 Kb in length and lacks any methylated nucleotides. In one embodiment the transgenic dicot plant, dicot plant part, or dicot plant cell (i.e., a transgenic soybean plant, soybean plant part, or soybean plant cell) comprises a DNA of interest inserted into the optimal nongenic soybean genomic locus wherein the DNA of interest comprises an analytical domain, and/or an open reading frame. In one embodiment the inserted DNA of interest encodes a peptide and in a further embodiment the DNA of interest comprises at least one gene expression cassette comprising a transgene.

EXAMPLES

Example 1: Identification of Targetable Genomic Loci in Soybean

The soybean genome was screened with a bioinformatics approach using specific criteria to select optimal genomic loci for targeting of a polynucleotide donor. The specific criteria used for selecting the genomic loci were developed using considerations for optimal expression of a transgene within the plant genome, considerations for optimal binding of genomic DNA by a site specific DNA-binding protein, and transgenic plant product development requirements. In order to identify and select the genomic loci, genomic and epigenomic datasets of the soybean genome were scanned using a bioinformatics approach. Screening genomic and epigenomic datasets resulted in select loci which met the following criteria: 1) hypomethylated and greater than 1 Kb in length; 2) targetable via site specific nuclease-mediated integration of a polynucleotide donor; 3) agronomically neutral or non-genic; 4) regions from which an integrated transgene can be expressed; and 5) regions with recombination within/around the locus. Accordingly, a total of 7,018 genomic loci (SEQ ID NO:1-SEQ ID NO:7,018) were identified using these specific criteria. The specific criteria are further described in detail below.

Hypomethylation

The soybean genome was scanned to select optimal genomic loci larger than 1 Kb that were DNA hypomethylated. DNA methylation profiles of root and shoot tissues isolated from *Glycine Max* cultivar Williams82 were constructed using a high throughput whole genome sequencing approach. Extracted DNA was subjected to bisulphite treatment that converts unmethylated cytosines to uracils, but does not affect methylated cytosines, and then sequenced using Illumina HiSeq technology (Krueger, F. et al. DNA methylome analysis using short bisulfite sequencing data. Nature Methods 9, 145-151 (2012)). The raw sequencing reads were collected and mapped to the soybean c.v. Williams82 reference genome using the Bismark™ mapping software as described in Krueger F, Andrews S R (2011) Bismark: a flexible aligner and methylation caller for Bisulfite-Seq applications. Bioinformatics 27: 1571-1572).

Since, during the bisulphite conversion process, cytosines in the DNA sequence that are methylated do not get converted to uracils, occurrence of cytosine bases in the sequencing data indicate the presence of DNA methylation. The reads that are mapped to the reference sequence were analyzed to identify genomic positions of cytosine residues with support for DNA methylation. The methylation level for each cytosine base in the genome was calculated as a percentage of the number of methylated reads mapping a particular cytosine base location to the total number of reads mapping to that location. The following hypothetical explains how methylation levels were calculated for each base within the soybean genome. For example, consider that there is a cytosine base at position 100 in chromosome 1 of the soybean c.v. Williams82 reference sequence. If there are a total of 20 reads mapped to cytosine base at position 100, and 10 of these reads are methylated, then the methylation level for the cytosine base at position 100 in chromosome 1 is estimated to be 50%. Accordingly, a profile of the methylation level for all of the genomic DNA base pairs obtained from the root and shoot tissue of soybean was calculated. The reads that could not be correctly mapped to unique locations in the soybean genome matched repetitive sequences that are widespread in the soybean genome, and are known in the art to be predominantly methylated.

Using the above described protocol, the methylation levels for the soybean c.v. Williams82 genome were measured. As such, regions of the soybean genome containing methylated reads indicated that these regions of the soybean genome were methylated. Conversely, the regions of the soybean genome that were absent of methylated reads indicated these regions of the soybean genome were non-methylated. The regions of the soybean genome from the shoot and root tissues that were non-methylated and did not contain any methylated reads are considered as "hypomethylated" regions. To make the root and shoot methylation profiles available for visualization, wiggle plots (http://useast.ensembl.org/info/website/upload/wig.html) were generated for each of the soybean c.v. Williams82 chromosomes.

After obtaining the DNA methylation level at the resolution of a single base pair in root and shoot tissues, as described above, the soybean genome was screened using 100 bp windows to identify genomic regions that are methylated. For each window screened in the genome, a DNA methylation level was obtained by calculating the average level of methylation at every cytosine base in that window. Genomic windows with a DNA methylation level greater than 1% were termed as genomic regions that were methylated. The methylated windows identified in root and shoot profiles were combined to create a consensus methylation profile. Conversely, regions in the genome that did not meet these criteria and were not identified as methylated regions in the consensus profile were termed as hypo-methylated regions. Table 1 summarizes the identified hypo-methylated regions.

TABLE 1

| Hypomethylation profile of soybean c.v. Williams82 genome. | |
|---|---|
| Total soybean c.v. Williams82 genome size | ~970 Mb |
| Total combined length of hypomethylated region | ~354 Mb (36.5% of the soybean c.v. Williams82 genome) |
| Number of hypomethylated regions above 100 Bp | 763,709 |
| Number of hypomethylated regions above 1 Kb | 94,745 |
| Number of hypomethylated regions above 2 Kb | 19,369 |
| Number of hypomethylated regions above 10 Kb | 354 |
| Minimum length of hypomethylated region | 100 Bp |
| Maximum length of hypomethylated region | 84,100 Bp |

These hypomethylated regions of the soybean c.v. WILLIAMS82 genome were further characterized to identify and select specific genomic loci as the methylation free context of these regions indicated the presence of open chromatin. As such, all subsequent analyses were conducted on the identified hypomethylated regions.

Targetability

The hypomethylated sites identified in the soybean c.v. WILLIAMS82 were further analyzed to determine which sites were targetable via site specific nuclease-mediated integration of a polynucleotide donor. *Glycine max* is known to be a palaeopolyploid crop which has undergone genome duplications in its genomic history (Jackson et al Genome sequence of the palaeopolyploid soybean, *Nature* 463, 178-183 (2010)). The soybean genome is known in the art to contain long stretches of highly repetitive DNA that are methylated and have high levels of sequence duplication. Annotation information of known repetitive regions in the soybean genome was collected from the Soybean Genome Database (www.soybase.org, Shoemaker, R. C. et al. *Soy-Base, the USDA-ARS soybean genetics and genomics database. Nucleic Acids Res.* 2010 January; 38(Database issue): D843-6.).

Accordingly, the hypomethylated sites identified above were screened to remove any sites that aligned with known repetitive regions annotated on the soybean genome. The remaining hypomethylated sites that passed this first screen were subsequently scanned using a BLAST™ based homology search of a soybean genomic database via the NCBI BLAST™+ software (version 2.2.25) run using default parameter settings (Stephen F. Altschul et al (1997) Gapped BLAST and PSI-BLAST: a new generation of protein database search programs. *Nucleic Acids Res.* 25:3389-3402). As a result of the BLAST™ screen, any hypomethylated sites that had significant matches elsewhere in the genome, with sequence alignment coverage of over 40%, were removed from further analyses.

Agronomically Neutral or Nongenic

The hypomethylated sites identified in the soybean c.v. William82 were further analyzed to determine which sites were agronomically neutral or nongenic. As such, the hypomethylated sites described above were screened to remove any sites that overlapped or contained any known or predicted endogenous soybean c.v. William82 coding sequences. For this purpose, annotation data of known genes and mapping information of expressed sequence tag (EST) data were collected from Soybean Genomic Database (www.soybase.org—version 1.1 gene models were used, Jackson et al Genome sequence of the palaeopolyploid soybean Nature 463, 178-183 (2010)). Any genomic region immediately 2 Kb upstream and 1 Kb downstream to an open reading frame were also considered. These upstream and downstream regions may contain known or unknown conserved regulatory elements that are essential for gene function. The hypomethylated sites previously described above were analyzed for the presence of the known genes (including the 2 Kb upstream and 1 Kb downstream regions) and ESTs. Any hypomethylated sites that aligned with or overlapped with known genes (including the 2 Kb upstream and 1 Kb downstream regions) or ESTs were removed from downstream analysis.

Expression

The hypomethylated sites identified in the soybean c.v. Williams82 were further analyzed to determine which sites were within proximity to an expressed soybean gene. The transcript level expression of soybean genes was measured by analyzing transcriptome profiling data generated from soybean c.v. Williams82 root and shoot tissues using RNAseg™ technology as described in Mortazavi et al., Mapping and quantifying mammalian transcriptomes by RNA-Seq. *Nat Methods.* 2008; 5(7):621-628, and Shoemaker R C et al., RNA-Seq Atlas of *Glycine max*: a guide to the soybean Transcriptome. *BMC Plant Biol.* 2010 Aug. 5; 10:160. For each hypomethylated site, an analysis was completed to identify any annotated genes present within a 40 Kb region in proximity of the hypomethylated site, and an average expression level of the annotated gene(s) located in proximity to the hypomethylated site. Hypomethylated sites located greater than 40 Kb from an annotated gene with a non-zero average expression level were determined to not be proximal to an expressed soybean gene and were removed from further analyses.

Recombination

The hypomethylated sites identified in the soybean c.v. Williams82 were further analyzed to determine which sites had evidence of recombination and could facilitate introgression of the optimal genomic loci into other lines of soybean via conventional breeding. Diverse soybean genotypes are routinely crossed during conventional breeding to develop new and improved soybean lines containing traits of agronomic interest. As such, agronomic traits that are introgressed into optimal genomic loci within a soybean line via plant-mediated transformation of a transgene should be capable of further being introgressed into other soybean lines, especially elite lines, via meiotic recombination during conventional plant breeding. The hypomethylated sites described above were screened to identify and select sites that possessed some level of meiotic recombination. Any hypomethylated sites that were present within chromosomal regions characterized as recombination "cold-spots" were identified and removed. In soybean, these cold spots were defined using a marker dataset generated from recombinant inbred mapping population (Williams 82×PI479752). This dataset consisted of ~16,600 SNP markers that could be physically mapped to the *Glycine max* reference genome sequence.

The meiotic recombination frequencies between any pair of soybean genomic markers across a chromosome were calculated based on the ratio of the genetic distance between markers (in centimorgan (cM)) to the physical distance between the markers (in megabases (Mb)). For example, if the genetic distance between a pair of markers was 1 cM, and the physical distance between the same pair of markers was 2 Mb, then the calculated recombination frequency was determined to be 0.5 cM/Mb. For each hypomethylated site identified above, a pair of markers at least 1 Mb apart was chosen and the recombination frequency was calculated. Deployment of this method was used to calculate the recombination frequency of the hypomethylated sites. Any hypomethylated sites with a recombination frequency of 0 cM/Mb were identified and removed from further analysis. The remaining hypomethylated regions comprising a recombination frequency greater than 0 cM/Mb were selected for further analysis.

Identification of Optimal Genomic Loci

Application of the selection criteria described above resulted in the identification of a total of 90,325 optimal genomic loci from the soybean genome. Table 2 summarizes the lengths of the identified optimal genomic loci. These optimal genomic loci possess the following characteristics: 1) hypomethylated genomic loci greater than 1 Kb in length; 2) genomic loci that are targetable via site specific nuclease-mediated integration of a polynucleotide donor; 3) genomic loci that are agronomically neutral or nongenic; 4) genomic loci from which a transgene can be expressed; and 5) evidence of recombination within the genomic loci. Of all of the optimal genomic loci described in Table 2, only the optimal genomic loci that were greater than 1 Kb were further analyzed and utilized for targeting of a donor polynucleotide sequence. The sequences of these optimal genomic loci are disclosed as SEQ ID NO:1-SEQ ID NO:7, 018. Collectively, these optimal genomic loci are locations within the soybean genome that can be targeted with a donor polynucleotide sequence, as further demonstrated herein below.

TABLE 2

Lists the size range of optimal genomic loci identified in the soybean genome that are hypomethylated, show evidence of recombination, targetable, agronomically neutral or nongenic, and are in proximity to an expressed endogenous gene.

| | |
|---|---|
| Number of optimal genomic loci larger than 100 Bp | 90,325 |
| Number of optimal genomic loci larger than 1 Kb | 7,018 |
| Number of optimal genomic loci larger than 2 Kb | 604 |
| Number of optimal genomic loci larger than 4 Kb | 9 |

Example 2: F-Distribution and Principal Component Analysis to Cluster Optimal Genomic Loci from Soybean The 7,018 identified optimal genomic loci (SEQ ID NO: 1-SEQ ID NO: 7,018) were further analyzed using the F-distribution and Principal Component Analysis statistical methods to define a representative population and clusters for grouping of the optimal genomic loci.

F-Distribution Analysis

The identified 7,018 optimal genomic loci were statistically analyzed using a continuous probability distribution statistical analysis. As an embodiment of the continuous probability distribution statistical analysis, an F-distribution test was completed to determine a representative number of optimal genomic loci. The F-distribution test analysis was completed using equations and methods known by those with skill in the art. For more guidance, the F-distribution test analysis as described in K. M Remund, D. Dixon, D L. Wright and L R. Holden. Statistical considerations in seed purity testing for transgenic traits. *Seed Science Research* (2001) 11, 101-119, herein incorporated by reference, is a non-limiting example of an F-distribution test. The F-distribution test assumes random sampling of the optimal genomic loci, so that any non-valid loci are evenly distributed across the 7,018 optimal genomic loci, and that the number of optimal genomic loci sampled is 10% or less of the total population of 7,018 optimal genomic loci.

The F-distribution analysis indicated that 32 of the 7,018 optimal genomic loci provided a representative number of the 7,018 optimal genomic loci, at a 95% confidence level. Accordingly, the F-distribution analysis showed that if 32 optimal genomic loci were tested and all were targetable with a donor polynucleotide sequence, then these results would indicate that 91 or more of the 7,018 optimal genomic loci are positive at the 95% confidence level. The best estimate of validating the total percentage of the 7,018 optimal genomic loci would be if 100% of the 32 tested optimal genomic loci were targetable. Accordingly, 91% is actually the lower bound of the true percent validated at the 95% confidence level. This lower bound is based on the 0.95 quantile of the F-distribution, for the 95% confidence level (Remund K, Dixon D, Wright D, and Holden L. Statistical considerations in seed purity testing for transgenic traits. *Seed Science Research* (2001) 11, 101-119).

Principal Component Analysis

Next, a Principal Component Analysis (PCA) statistical method was completed to further assess and visualize similarities and differences of the data set comprising the 7,018 identified optimal genomic loci to enable sampling of diverse loci for targeting validation. The PCA involves a mathematical algorithm that transforms a larger number of correlated variables into a smaller number of uncorrelated variables called principal components.

The PCA was completed on the 7,018 identified optimal genomic loci by generating a set of calculable features or attributes that could be used to describe the 7,018 identified optimal genomic loci. Each feature is numerically calculable and is defined specifically to capture the genomic and epigenomic context of the 7,018 identified optimal genomic loci. A set of 10 features for each soybean optimal genomic loci was identified and are described in greater detail below.

1. Length of the Optimal Genomic Loci
   a. The length of the optimal genomic loci in this data set ranged from a minimum of 1,000 Bp to a maximum of 5,713 Bp.
2. Recombination Frequency in a 1 MB Region Around the Optimal Genomic Loci
   a. In soybean, recombination frequency for a chromosomal location was defined using an internal high resolution marker dataset generated from multiple mapping populations.
   b. Recombination frequencies between any pairs of markers across the chromosome were calculated based on the ratio of the genetic distance between markers (in centimorgan (cM)) to the physical distance between the markers (in Mb). For example, if the genetic distance between a pair of markers is 1 cM and the physical distance between the same pairs of markers is 2 Mb, the calculated recombination frequency is 0.5 cM/Mb. For each optimal genomic loci, a pair of markers at least 1 Mb apart was chosen and the recombination frequency was calculated in this manner. These recombination values ranged from a minimum of 0.01574 cM/Mb to a maximum of 83.52 cM/Mb.
3. Level of Optimal Genomic Loci Sequence Uniqueness
   a. For each optimal genomic loci, the nucleotide sequence of the optimal genomic loci was scanned against the soybean c.v. Williams82 genome using a BLAST™ based homology search using the NCBI BLAST™+ software (version 2.2.25) run using the default parameter settings (Stephen F. Altschul et al (1997), "Gapped BLAST and PSI-BLAST: a new generation of protein database search programs", Nucleic Acids Res. 25:3389-3402). As these optimal genomic loci sequences are identified from the soybean c.v. Williams82 genome, the first BLAST™ hit identified through this search represents the soybean c.v. Williams82 sequence itself. The second BLAST™ hit for each optimal genomic loci sequence was identified and the alignment coverage (represented as the percent of the optimal genomic loci covered by the BLAST™ hit) of the hit was used as a measure of uniqueness of the optimal genomic loci sequence within the soybean genome. These alignment coverage values for the second BLAST™ hit ranged from a minimum of 0% to a maximum of 39.97% sequence identity. Any sequences that aligned at higher levels of sequence identity were not considered.
4. Distance from the Optimal Genomic Loci to the Closest Gene in its Neighborhood
   a. Gene annotation information and the location of known genes in the Soybean genome were extracted from Soybean Genome Database (available at, www.soybase.org—version 1.1 gene models were used, Jackson et al Genome sequence of the palaeopolyploid soybean, *Nature* 463, 178-183 (2010)). For each optimal genomic loci, the closest annotated gene, considering both upstream and downstream locations, was identified and the distance between the optimal genomic loci sequence and the gene was measured (in Bp). For example, if a optimal genomic locus is located in chromosome Gm01 from position 2,500 to position 3,500, and the closest gene to this optimal genomic locus is located in chromosome Gm01 from position 5,000 to position 6,000, the distance from the optimal genomic loci to this closest gene is calculated to be 1500 Bp. These values for all 7,018 of the optimal genomic loci dataset ranged from a minimum of 1,001 Bp to a maximum of 39,482 Bp.
5. GC % in the Optimal Genomic Loci Sequence
   a. For each optimal genomic locus, the nucleotide sequence was analyzed to estimate the number of Guanine and Cytosine bases present. This count was represented as a percentage of the sequence length of each optimal genomic locus and provides a measure for GC %. These GC % values for the soybean optimal genomic loci dataset range from 14.4% to 45.9%.

6. Number of Genes in a 40 Kb Neighborhood Around the Optimal Genomic Loci Sequence
   a. Gene annotation information and the location of known genes in the soybean c.v. Williams82 genome were extracted from Soybean Genome Database. For each of the 7,018 optimal genomic loci sequence, a 40 Kb window around the optimal genomic loci sequence was defined and the number of annotated genes with locations overlapping this window was counted. These values ranged from a minimum of 1 gene to a maximum of 18 genes within the 40 Kb neighborhood.

7. Average Gene Expression in a 40 Kb Neighborhood Around the Optimal Genomic Loci
   a. Transcript level expression of soybean genes was measured by analyzing available transcriptome profiling data generated from soybean c.v. Williams82 root and shoot tissues using RNAseg™ technology. Gene annotation information and the location of known genes in the soybean c.v. Williams82 genome were extracted from Soybean Genome Database For each optimal genomic locus, annotated genes within the soybean c.v. Williams82 genome that were present in a 40 Kb neighborhood around the optimal genomic loci were identified. Expression levels for each of the genes were extracted from the transcriptome profiles described in the above referenced citations and an average gene expression level was calculated. Expression values of all genes within the genome of soybean vary greatly. The average expression values for all of the 7,018 optimal genomic loci dataset ranged from a minimum of 0.000415 to a maximum of 872.7198.

8. Level of Nucleosome Occupancy Around the Optimal Genomic Loci
   a. Understanding the level of nucleosome occupancy for a particular nucleotide sequence provides information about chromosomal functions and the genomic context of the sequence. The NuPoP™ statistical package was used to predict the nucleosome occupancy and the most probable nucleosome positioning map for any size of genomic sequences (Xi, L., Fondufe-Mittendor, Y., Xia, L., Flatow, J., Widom, J. and Wang, J.-P., Predicting nucleosome positioning using a duration Hidden Markov Model, *BMC Bioinformatics,* 2010, doi: 10.1186/1471-2105-11-346.). For each of the 7,018 optimal genomic loci, the nucleotide sequence was submitted for analysis with the NuPoP™ software and a nucleosome occupancy score was calculated. These nucleosome occupancy scores for the soybean optimal genomic loci dataset ranged from a minimum of 0 to a maximum of 0.494.

9. Relative Location within the Chromosome (Proximity to Centromere)
   a. A centromere is a region on a chromosome that joins two sister chromatids. The portions of a chromosome on either side of the centromere are known as chromosomal arms. Genomic locations of centromeres on all 20 Soybean chromosomes were identified in the published soybean c.v. Williams82 reference sequence (Jackson et al Genome sequence of the palaeopolyploid soybean *Nature* 463, 178-183 (2010)). Information on the position of the centromere in each of the Soybean chromosomes and the lengths of the chromosome arms was extracted from Soybean Genome Database. For each optimal genomic locus, the genomic distance from the optimal genomic locus sequence to the centromere of the chromosome that it is located on, is measured (in Bp). The relative location of optimal genomic loci within the chromosome is represented as the ratio of its genomic distance to the centromere relative to the length of the specific chromosomal arm that it lies on. These relative location values for the soybean optimal genomic loci dataset ranged from a minimum of 0 to a maximum of 0.99682 ratio of genomic distance.

10. Number of Optimal Genomic Loci in a 1 Mb Region
    a. For each optimal genomic loci, a 1 Mb genomic window around the optimal genomic loci location was defined and the number of other, additional optimal genomic loci present within or overlapping this region were calculated, including the optimal genomic loci under consideration. The number of optimal genomic loci in a 1 Mb ranged from a minimum of 1 to a maximum of 49.

All of the 7,018 optimal genomic loci were analyzed using the features and attributes described above. The results or values for the score of the features and attributes of each optimal genomic locus are further described in Table 3 (herein incorporated by reference as a separate electronic filing). The resulting dataset was used in the PCA statistical method to cluster the 7,018 identified optimal genomic loci into clusters. During the clustering process, after estimating the "p" principle components of the optimal genomic loci, the assignment of the optimal genomic loci to one of the 32 clusters proceeded in the "p" dimensional Euclidean space. Each of the "p" axes was divided into "k" intervals. Optimal genomic loci assigned to the same interval were grouped together to form clusters. Using this analysis, each PCA axis was divided into two intervals, which was chosen based on a priori information regarding the number of clusters required for experimental validation. All analysis and the visualization of the resulting clusters were carried out with the Molecular Operating Environment™ (MOE) software from Chemical Computing Group Inc. (Montreal, Quebec, Canada).

The PCA approach was used to cluster the set of 7,018 identified optimal genomic loci into 32 distinct clusters based on their feature values, described above. During the PCA process, five principal components (PC) were generated, with the top three PCs containing about 90% of the total variation in the dataset (Table 4). These three PCAs were used to graphically represent the 32 clusters in a three dimensional plot (FIG. 1). After the clustering process, was completed, one representative optimal genomic locus was chosen from each cluster. This was performed by choosing a select optimal genomic locus, within each cluster, that was closest to the centroid of that cluster (Table 4). The chromosomal locations of the 32 representative optimal genomic loci are uniformly distributed among the 20 soybean chromosomes and are not biased toward any particular genomic location, as shown in FIG. 2.

TABLE 4

Description of the 32 soybean representative optimal genomic loci identified from the PCA

| Optimal Genomic Loci Name | Genomic Location | Length (Bp) | Cluster Number | SEQ ID NO: |
|---|---|---|---|---|
| soy_ogl_2474 | Gm08: 2764201..2766752 | 2552 | 1 | 1 |
| soy_ogl_768 | Gm03: 339101..341100 | 2000 | 2 | 506 |
| soy_ogl_2063 | Gm06: 43091928..43094600 | 2673 | 3 | 748 |
| soy_ogl_1906 | Gm06: 11576991..11578665 | 1675 | 4 | 1029 |
| soy_ogl_1112 | Gm03: 46211408..46213400 | 1993 | 5 | 1166 |
| soy_ogl_3574 | Gm10: 46279901..46281026 | 1126 | 6 | 1452 |
| soy_ogl_2581 | Gm08: 9631801..9632800 | 1000 | 7 | 1662 |

TABLE 4-continued

Description of the 32 soybean representative optimal genomic loci identified from the PCA

| Optimal Genomic Loci Name | Genomic Location | Length (Bp) | Cluster Number | SEQ ID NO: |
|---|---|---|---|---|
| soy_ogl_3481 | Gm10: 40763663..40764800 | 1138 | 8 | 1869 |
| soy_ogl_1016 | Gm03: 41506001..41507735 | 1735 | 9 | 2071 |
| soy_ogl_937 | Gm03: 37707001..37708600 | 1600 | 10 | 2481 |
| soy_ogl_6684 | Gm20: 1754801..1755800 | 1000 | 11 | 2614 |
| soy_ogl_6801 | Gm20: 36923690..36924900 | 1211 | 12 | 2874 |
| soy_ogl_6636 | Gm19: 49977101..49978357 | 1257 | 13 | 2970 |
| soy_ogl_4665 | Gm14: 5050547..5051556 | 1010 | 14 | 3508 |
| soy_ogl_3399 | Gm10: 6612501..6613500 | 1000 | 15 | 3676 |
| soy_ogl_4222 | Gm13: 23474923..23476100 | 1178 | 16 | 3993 |
| soy_ogl_2543 | Gm08: 7532001..7534800 | 2800 | 17 | 4050 |
| soy_ogl_275 | Gm01: 51869201..51870400 | 1200 | 18 | 4106 |
| soy_ogl_598 | Gm02: 41665601..41667900 | 2300 | 19 | 4496 |
| soy_ogl_1894 | Gm06: 10540801..10542300 | 1500 | 20 | 4622 |
| soy_ogl_5454 | Gm17: 1944101..1945800 | 1700 | 21 | 4875 |
| soy_ogl_6838 | Gm20: 38263922..38265300 | 1379 | 22 | 4888 |
| soy_ogl_4779 | Gm14: 45446301..45447700 | 1400 | 23 | 5063 |
| soy_ogl_3333 | Gm10: 2950701..2951800 | 1100 | 24 | 5122 |
| soy_ogl_2546 | Gm08: 7765875..7767500 | 1626 | 25 | 5520 |
| soy_ogl_796 | Gm03: 1725501..1726600 | 1100 | 26 | 5687 |
| soy_ogl_873 | Gm03: 33650665..33653000 | 2336 | 27 | 6087 |
| soy_ogl_5475 | Gm17: 3403108..3404200 | 1093 | 28 | 6321 |
| soy_ogl_2115 | Gm07: 1389701..1390900 | 1200 | 29 | 6520 |
| soy_ogl_2518 | Gm08: 5229501..5230667 | 1167 | 30 | 6574 |
| soy_ogl_5551 | Gm17: 6541901..6543200 | 1300 | 31 | 6775 |
| soy_ogl_4563 | Gm13: 38977701..38978772 | 1072 | 32 | 6859 |

Figure 3:
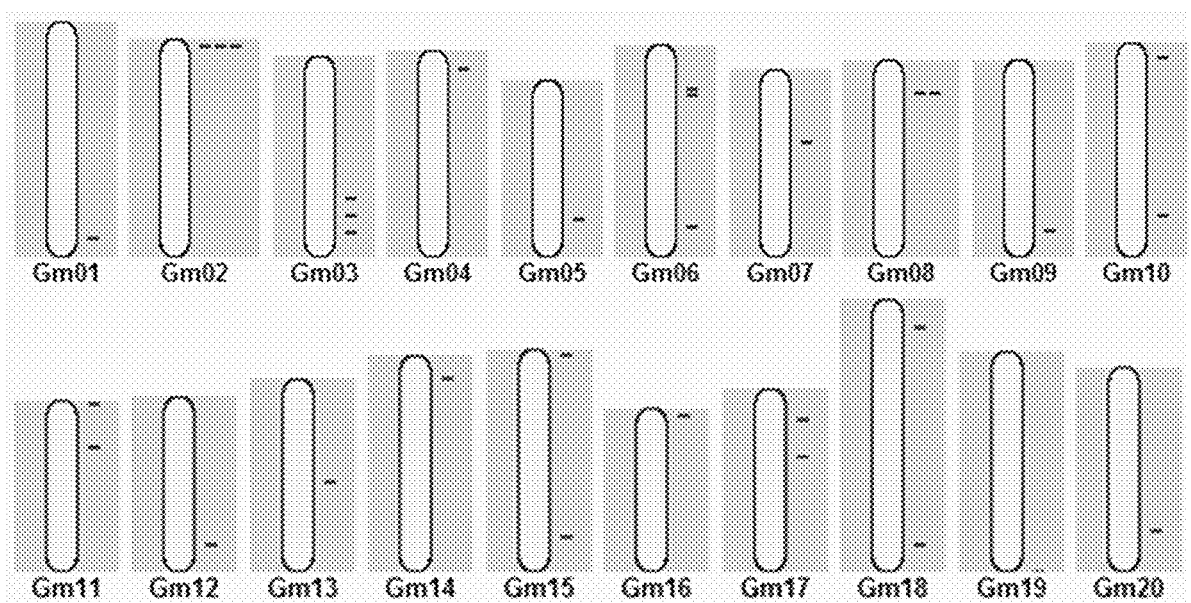
FIG. 3. Provides a schematic drawing indicating the soybean chromosomal location of the optimal genomic loci selected for targeting validation.

Final Selection of Genomic Loci for Targeting of a Polynucleotide Donor Polynucleotide Sequence A total of 32 genomic loci were identified and selected for targeting with a donor polynucleotide sequence from the 7,018 genomic loci that were clustered within 32 distinct clusters. For each of the 32 clusters, a representative genomic locus (closest to the centroid of the cluster as described above in Table 4) or an additional locus with homology to targeting line were chosen. The additional optimal genomic loci were selected by first screening all of the 7,018 selected optimal genomic sequences against a whole genome database consisting of genomic DNA sequence data for both *Glycine max* c.v. Maverick (transformation and targeting screening line) and *Glycine max* c.v. Williams82 (reference line) to determine the coverage (how many optimal genomic loci were present in both genomes) and percentage of sequence identity in the genome from both lines. The optimal genomic loci with 100% coverage (the entire sequence length of the optimal loci aligned between both genomes) and 100% identity in the Williams82 genomic databases were selected for targeting validation. Other criteria such as genomic loci size, extent of uniqueness, GC % content and chromosomal distribution of the optimal genomic loci were also taken into consideration in selecting the additional optimal genomic loci. The chromosomal location of the 32 selected optimal genomic loci and the specific genomic configuration of each soybean optimal genomic loci are shown in FIG. 3 and Table 5, respectively.

TABLE 5

Description of the 32 soybean selected optimal genomic loci chosen for targeting validation. From these optimal genomic loci listed in this table, exemplification of cleavage and targeting of 32 soybean optimal genomic loci are representative of the identified total of 7,018 soybean selected optimal genomic loci.

| Optimal Genomic Loci Name | Genomic Location | Length (Bp) | Cluster Number | SEQ ID NO: |
|---|---|---|---|---|
| soy_ogl_308 | Gm02: 1204801..1209237 | 4437 | 1 | 43 |
| soy_ogl_307 | Gm02: 1164701..1168400 | 3700 | 2 | 566 |
| soy_ogl_2063 | Gm06: 43091928..43094600 | 2673 | 3 | 748 |
| soy_ogl_1906 | Gm06: 11576991..11578665 | 1675 | 4 | 1029 |
| soy_ogl_262 | Gm01: 51061272..51062909 | 1638 | 5 | 1376 |
| soy_ogl_5227 | Gm16: 1298889..1300700 | 1812 | 6 | 1461 |
| soy_ogl_4074 | Gm12: 33610401..33611483 | 1083 | 7 | 1867 |
| soy_ogl_3481 | Gm10: 40763663..40764800 | 1138 | 8 | 1869 |
| soy_ogl_1016 | Gm03: 41506001..41507735 | 1735 | 9 | 2071 |
| soy_ogl_937 | Gm03: 37707001..37708600 | 1600 | 10 | 2481 |
| soy_ogl_5109 | Gm15: 42391349..42393400 | 2052 | 11 | 2639 |
| soy_ogl_6801 | Gm20: 36923690..36924900 | 1211 | 12 | 2874 |
| soy_ogl_6636 | Gm19: 49977101..49978357 | 1257 | 13 | 2970 |
| soy_ogl_4665 | Gm14: 5050547..5051556 | 1010 | 14 | 3508 |
| soy_ogl_6189 | Gm18: 55694401..55695900 | 1500 | 15 | 3682 |
| soy_ogl_4222 | Gm13: 23474923..23476100 | 1178 | 16 | 3993 |
| soy_ogl_2543 | Gm08: 7532001..7534800 | 2800 | 17 | 4050 |
| soy_ogl_310 | Gm02: 1220301..1222300 | 2000 | 18 | 4326 |
| soy_ogl_2353 | Gm07: 17194521..17196553 | 2032 | 19 | 4593 |
| soy_ogl_1894 | Gm06: 10540801..10542300 | 1500 | 20 | 4622 |
| soy_ogl_3669 | Gm11: 624301..626200 | 1900 | 21 | 4879 |
| soy_ogl_3218 | Gm09: 40167479..40168800 | 1322 | 22 | 4932 |
| soy_ogl_5689 | Gm17: 15291601..15293400 | 1800 | 23 | 5102 |
| soy_ogl_3333 | Gm10: 2950701..2951800 | 1100 | 24 | 5122 |
| soy_ogl_2546 | Gm08: 7765875..7767500 | 1626 | 25 | 5520 |
| soy_ogl_1208 | Gm04: 4023654..4025650 | 1997 | 26 | 5698 |
| soy_ogl_873 | Gm03: 33650665..33653000 | 2336 | 27 | 6087 |
| soy_ogl_5957 | Gm18: 6057701..6059100 | 1400 | 28 | 6515 |
| soy_ogl_4846 | Gm15: 924901..926200 | 1300 | 29 | 6571 |
| soy_ogl_3818 | Gm11: 10146701..10148200 | 1500 | 30 | 6586 |
| soy_ogl_5551 | Gm17: 6541901..6543200 | 1300 | 31 | 6775 |
| soy_ogl_7 | Gm05: 32631801..32633200 | 1400 | 32 | 6935 |
| soy_OGL_684 | Gm02: 45903201..45907300 | 4100 | 1 | 47 |
| soy_OGL_682 | Gm02: 45816543..45818777 | 2235 | 9 | 2101 |

TABLE 5-continued

Description of the 32 soybean selected optimal genomic loci chosen for targeting validation. From these optimal genomic loci listed in this table, exemplification of cleavage and targeting of 32 soybean optimal genomic loci are representative of the identified total of 7,018 soybean selected optimal genomic loci.

| Optimal Genomic Loci Name | Genomic Location | Length (Bp) | Cluster Number | SEQ ID NO: |
|---|---|---|---|---|
| soy_OGL_685 | Gm02: 45910501..45913200 | 2700 | 1 | 48 |
| soy_OGL_1423 | Gm04: 45820631..45822916 | 2286 | 2 | 639 |
| soy_OGL_1434 | Gm04: 46095801..46097968 | 2168 | 1 | 137 |
| soy_OGL_4625 | Gm14: 3816738..3820070 | 3333 | 1 | 76 |
| soy_OGL_6362 | Gm19: 5311001..5315000 | 4000 | 1 | 440 |

A large suite of 7,018 genomic locations have been identified in the soybean genome as optimal genomic loci for targeting with a donor polynucleotide sequence using precision genome engineering technologies. A statistical analysis approach was deployed to group the 7,018 selected genomic loci into 32 clusters with similar genomic contexts, and to identify a subset of 32 selected genomic loci representative of the set of 7,018 selected genomic loci. The 32 representative loci were validated as optimal genomic loci via targeting with a donor polynucleotide sequence. By performing the PCA statistical analysis for the numerical values generated for the ten sets of features or attributes that are described above, the ten features or attributes were computed into PCA components of fewer dimensions. As such, PCA components were reduced into five dimensions that are representative of the ten features or attributes described above (Table 6). Each PCA component is equivalent to a combination of the ten features or attributes described above. From these PCA components comprising five dimensions, as computed using the PCA statistical analysis, the 32 clusters were determined.

TABLE 6

The five PCA components (PCA1, PCA2, PCA3, PCA4, and PCA5) that define each of the 32 clusters and the sequences (SEQ ID NO: 1-SEQ ID NO: 7,018) which make up each cluster. These five dimensions are representative of the ten features or attributes described above that were used to identify the optimal genomic loci. The minimum (Min), mean, median and maximum (Max) values for each PCA component are provided.

| | | Cluster1 (SEQ ID NO: 1-- SEQ ID NO: 505) | Cluster2 (SEQ ID NO: 506-- SEQ ID NO: 747) | Cluster3 (SEQ ID NO: 748-- SEQ ID NO: 1028) | Cluster4 (SEQ ID NO: 1029-- SEQ ID NO: 1165) | Cluster5 (SEQ ID NO: 1166-- SEQ ID NO: 1451) | Cluster6 (SEQ ID NO: 1452-- SEQ ID NO: 1661) | Cluster7 (SEQ ID NO: 1662-- SEQ ID NO: 1868) | Cluster8 (SEQ ID NO: 1869-- SEQ ID NO: 2070) |
|---|---|---|---|---|---|---|---|---|---|
| PCA1 | Min | −1.70227 | 0.022046 | −4.54911 | −1.72266 | −0.36976 | 0.287697 | −3.34863 | −1.0806 |
| | Mean | 0.349775 | 0.812634 | −1.47305 | −0.00185 | 0.540899 | 0.967917 | −0.58528 | 0.313491 |
| | Median | 0.363103 | 0.796321 | −1.18164 | 0.049082 | 0.52498 | 0.918269 | −0.34364 | 0.291582 |
| | Max | 1.507894 | 1.834871 | 0.032399 | 2.027233 | 1.499719 | 2.461219 | 0.417058 | 1.718384 |
| PCA2 | Min | −0.65485 | −0.6907 | −1.37642 | −1.15246 | −2.2623 | −2.69847 | −2.33499 | −2.05394 |
| | Mean | 0.803591 | 0.805611 | 0.42863 | 0.549053 | −0.97646 | −0.63594 | −1.07926 | −0.67684 |
| | Median | 0.640172 | 0.690953 | 0.30208 | 0.435896 | −0.92946 | −0.51848 | −1.03176 | −0.62625 |
| | Max | 6.750318 | 4.21286 | 3.492035 | 2.037537 | 0.224862 | 0.316075 | 0.014994 | 0.262266 |
| PCA3 | Min | −4.63386 | 6.20928 | −3.64977 | −7.46971 | −2.4347 | −3.28026 | −2.79672 | −2.36222 |
| | Mean | −1.0374 | 0.87017 | −1.09511 | −1.21149 | −0.49711 | −0.30392 | −0.4893 | −0.36718 |
| | Median | −0.94654 | −0.7282 | −0.92816 | −0.96309 | −0.45901 | −0.19996 | −0.43677 | −0.27515 |
| | Max | 0.240454 | 0.010148 | −0.11534 | −0.13414 | 0.476554 | 0.457804 | 0.452481 | 0.453505 |
| PCA4 | Min | −2.22011 | 1.02405 | −1.33923 | 0.069312 | −1.70627 | −0.80904 | −1.29231 | 0.360563 |
| | Mean | −0.71495 | 0.283541 | 0.212841 | 1.084988 | −0.35855 | 0.479481 | 0.459736 | 1.348666 |
| | Median | −0.70787 | 0.306108 | 0.209055 | 1.116651 | −0.35772 | 0.435449 | 0.436138 | 1.307628 |
| | Max | 0.786678 | 1.575184 | 2.221794 | 2.571196 | 0.755949 | 2.664817 | 2.193427 | 3.122114 |
| PCA5 | Min | −0.17971 | 3.06393 | −0.53749 | −4.5557 | 0.159064 | −2.0539 | −0.70289 | −1.90857 |
| | Mean | 0.943093 | 0.368965 | 0.713771 | −0.21905 | 0.876745 | 0.463248 | 0.768677 | 0.285719 |
| | Median | 0.854279 | 0.3771 | 0.670629 | −0.10817 | 0.846543 | 0.459296 | 0.763885 | 0.338391 |
| | Max | 3.583402 | 2.613815 | 2.279238 | 2.341478 | 1.913726 | 1.633977 | 2.164417 | 1.422805 |

| | | Cluster9 (SEQ ID NO: 2071-- SEQ ID NO: 2480) | Cluster10 (SEQ ID NO: 2481-- SEQ ID NO: 2613) | Cluster11 (SEQ ID NO: 2614-- SEQ ID NO: 2873) | Cluster12 (SEQ ID NO: 2874-- SEQ ID NO: 2969) | Cluster13 (SEQ ID NO: 2970-- SEQ ID NO: 3507) | Cluster14 (SEQ ID NO: 3508-- SEQ ID NO: 3675) | Cluster15 (SEQ ID NO: 3676-- SEQ ID NO: 3992) | Cluster16 (SEQ ID NO: 3993-- SEQ ID NO: 4049) |
|---|---|---|---|---|---|---|---|---|---|
| PCA1 | Min | −1.5084417 | −0.06921 | −4.85854 | −2.10567 | −0.78413 | −0.1362 | −3.50478 | −1.06581 |
| | Mean | 0.178145825 | 0.746656 | −1.77485 | 0.215254 | 0.402511 | 0.841125 | −0.99405 | 0.054644 |
| | Median | 0.204892845 | 0.729936 | −1.59613 | 0.167943 | 0.421486 | 0.793343 | −0.86435 | 0.043314 |
| | Max | 1.4452823 | 2.258209 | −0.10335 | 2.638122 | 1.521265 | 2.011089 | 0.254192 | 1.078006 |
| PCA2 | Min | −0.85615188 | −1.07918 | −1.48917 | −3.24885 | −2.49287 | −2.07915 | −2.50642 | −2.60289 |
| | Mean | 0.0131018 | 0.201017 | −0.12584 | −0.53611 | −1.09247 | −0.94959 | −1.29395 | −1.20352 |
| | Median | −0.061526693 | 0.165577 | −0.16842 | −0.33651 | −1.08189 | −0.91699 | −1.24996 | −1.17679 |
| | Max | 2.8737593 | 1.883538 | 2.389063 | 2.608386 | −0.24001 | 0.020389 | −0.4655 | −0.31958 |

TABLE 6-continued

The five PCA components (PCA1, PCA2, PCA3, PCA4, and PCA5) that define each of the 32 clusters and the sequences (SEQ ID NO: 1-SEQ ID NO: 7,018) which make up each cluster. These five dimensions are representative of the ten features or attributes described above that were used to identify the optimal genomic loci. The minimum (Min), mean, median and maximum (Max) values for each PCA component are provided.

| | | | | | | | | |
|---|---|---|---|---|---|---|---|---|
| PCA3 | Min | −1.7842444 | −3.17428 | −2.64864 | −14.6314 | −1.01198 | −1.91077 | −1.7135 | −2.73956 |
| | Mean | 0.137149779 | −0.20772 | −0.28997 | −3.0284 | 0.137956 | 0.208329 | 0.071922 | −0.21452 |
| | Median | 0.068803158 | −0.04455 | −0.18716 | −1.93463 | 0.177648 | 0.306399 | 0.132791 | −0.00072 |
| | Max | 0.9092167 | 0.928412 | 0.782125 | 0.72284 | 1.034171 | 1.086972 | 0.996862 | 0.765974 |
| PCA4 | Min | −2.9615474 | −2.44418 | −2.7613 | −1.00771 | −2.10637 | −1.17239 | −1.48955 | −0.78727 |
| | Mean | −1.407512305 | −0.75615 | −0.85361 | 0.594551 | −0.85746 | −0.33529 | −0.37717 | 0.438916 |
| | Median | −1.38790425 | −0.78738 | −0.81593 | 0.392421 | −0.86062 | −0.4333 | −0.47105 | 0.356632 |
| | Max | −0.40942505 | 0.783523 | 0.985444 | 4.86024 | 0.27396 | 0.580863 | 0.978394 | 2.500934 |
| PCA5 | Min | −1.897981 | −4.47156 | −2.35152 | −18.7726 | −0.77506 | −3.53913 | −1.20206 | −3.51125 |
| | Mean | −0.029561107 | −0.90424 | −0.18625 | −4.21943 | 0.229577 | −0.3992 | 0.08327 | −0.93398 |
| | Median | 0.034177913 | −0.68409 | −0.12264 | −2.90093 | 0.240883 | −0.33338 | 0.087451 | −0.70513 |
| | Max | 0.84937429 | 0.242494 | 0.940019 | −0.33401 | 1.115681 | 0.396515 | 1.044241 | 0.040091 |

| | | Cluster17 (SEQ ID NO: 4050-- SEQ ID NO: 4105) | Cluster18 (SEQ ID NO: 4106-- SEQ ID NO: 4495) | Cluster19 (SEQ ID NO: 4496-- SEQ ID NO: 4621) | Cluster20 (SEQ ID NO: 4622-- SEQID NO: 4874) | Cluster21 (SEQ ID NO: 4875-- SEQ ID NO: 4887) | Cluster22 (SEQ ID NO: 4888-- SEQ ID NO: 5062) | Cluster23 (SEQ ID NO: 5063-- SEQ ID NO: 5121) | Cluster24 (SEQ ID NO: 5122-- SEQ ID NO: 5519) |
|---|---|---|---|---|---|---|---|---|---|
| PCA1 | Min | −0.48995 | −0.12394 | −3.44417 | −2.5926 | 0.041919 | 0.192262 | −3.01097 | −2.17545 |
| | Mean | 0.218477 | 0.705185 | −1.60324 | −0.21989 | 0.498017 | 0.919859 | −1.10273 | 0.189203 |
| | Median | 0.186449 | 0.69823 | −1.62442 | −0.07645 | 0.530588 | 0.860249 | −1.05343 | 0.274006 |
| | Max | 1.212386 | 1.894809 | −0.14778 | 1.10593 | 0.937608 | 1.90419 | 0.215051 | 1.539568 |
| PCA2 | Min | 0.060129 | 0.131404 | −0.33368 | −0.05632 | −1.56352 | −1.38005 | −1.37504 | −1.29996 |
| | Mean | 1.419729 | 1.150768 | 1.001573 | 0.843814 | −0.4111 | −0.07498 | −0.52564 | −0.24039 |
| | Median | 1.280417 | 1.065186 | 0.789798 | 0.776486 | −0.28559 | −0.02529 | −0.48207 | −0.18651 |
| | Max | 3.913198 | 3.040107 | 6.340514 | 2.929741 | 0.123387 | 0.788801 | 0.176255 | 0.87503 |
| PCA3 | Min | −1.73844 | −1.13076 | −1.78506 | −0.92532 | 0.00053 | −0.17801 | −0.26777 | −0.37688 |
| | Mean | −0.27811 | 0.161876 | −0.14195 | 0.233953 | 0.437291 | 0.567525 | 0.293 | 0.505379 |
| | Median | −0.15148 | 0.163129 | −0.06546 | 0.23185 | 0.450869 | 0.560588 | 0.264634 | 0.473588 |
| | Max | 0.427866 | 1.323874 | 0.948736 | 1.409277 | 0.918483 | 1.635718 | 0.932042 | 1.841691 |
| PCA4 | Min | −1.60097 | −0.69878 | −1.09012 | 0.172103 | −0.51316 | −0.24073 | 0.213129 | 0.305131 |
| | Mean | −0.23831 | 0.47476 | 0.670052 | 1.210219 | 0.100213 | 0.936613 | 1.158602 | 1.628149 |
| | Median | −0.21174 | 0.451745 | 0.638494 | 1.196036 | 0.075167 | 0.954165 | 1.088302 | 1.633074 |
| | Max | 0.871996 | 1.775638 | 2.468554 | 2.614263 | 0.536589 | 2.449815 | 2.046121 | 2.833294 |
| PCA5 | Min | 0.008136 | −0.77069 | −0.62934 | −1.42543 | 0.258308 | −0.57322 | −0.00876 | −1.17026 |
| | Mean | 0.701934 | 0.233117 | 0.369827 | −0.02377 | 0.648857 | 0.282176 | 0.59606 | 0.172591 |
| | Median | 0.602369 | 0.225125 | 0.29277 | −0.01138 | 0.603284 | 0.263371 | 0.577423 | 0.151654 |
| | Max | 2.01268 | 1.665714 | 1.937356 | 1.791794 | 1.079582 | 1.412132 | 1.322481 | 1.497953 |

| | | Cluster25 (SEQ ID NO: 5520-- SEQ ID NO: 5686) | Cluster26 (SEQ ID NO: 5687-- SEQ ID NO: 6086) | Cluster27 (SEQ ID NO: 6087-- SEQ ID NO: 6320) | Cluster28 (SEQ ID NO: 6321-- SEQ ID NO: 6519) | Cluster29 (SEQ ID NO: 6520-- SEQ ID NO: 6573) | Cluster30 (SEQ ID NO: 6574-- SEQ ID NO: 6774) | Cluster31 (SEQ ID NO: 6775-- SEQ ID NO: 6588) | Cluster32 (SEQ ID NO: 6589- SEQ ID NO: 7018) |
|---|---|---|---|---|---|---|---|---|---|
| PCA1 | Min | −1.47203 | −0.82652 | −4.22215 | −2.8128 | −0.55955 | −0.14823 | −3.68328 | −2.1948 |
| | Mean | 0.026625 | 0.609339 | −1.7704 | −0.5307 | 0.365085 | 0.695365 | −1.17291 | −0.20762 |
| | Median | 0.000548 | 0.622131 | −1.68559 | −0.44093 | 0.372341 | 0.679272 | −1.05591 | −0.07481 |
| | Max | 1.204076 | 2.040596 | −0.20599 | 1.026142 | 1.082778 | 1.542552 | −0.04543 | 1.044939 |
| PCA2 | Min | −0.49733 | −0.35268 | −0.8685 | −0.39322 | −1.70938 | −1.71589 | −1.7904 | −1.39851 |
| | Mean | 0.701345 | 0.996746 | 0.520887 | 0.744232 | −0.66621 | −0.41853 | −0.82975 | −0.40126 |
| | Median | 0.497651 | 0.817435 | 0.384759 | 0.686377 | −0.69103 | −0.33802 | −0.8047 | −0.39539 |
| | Max | 3.880586 | 4.311936 | 3.021218 | 3.474901 | 0.015191 | 0.704506 | −0.11251 | 0.595757 |
| PCA3 | Min | −0.16467 | −0.23246 | −0.47501 | −0.00111 | 0.538379 | 0.435168 | 0.337445 | 0.222405 |
| | Mean | 0.71742 | 1.077263 | 0.78187 | 1.005429 | 1.055894 | 1.156804 | 1.045676 | 1.227425 |
| | Median | 0.674781 | 1.053549 | 0.727749 | 1.007761 | 1.085427 | 1.14325 | 1.036725 | 1.200613 |
| | Max | 2.234525 | 2.790854 | 2.556613 | 2.483974 | 1.565017 | 3.16182 | 1.973707 | 2.509435 |
| PCA4 | Min | −3.03078 | −3.22656 | −2.78298 | −0.8606 | −1.61996 | −1.16215 | −1.17888 | −2.50044 |
| | Mean | −1.25321 | −0.49661 | −0.42577 | 0.564935 | −0.67182 | −0.02267 | 0.109856 | 0.973061 |
| | Median | −1.21889 | −0.46274 | −0.40653 | 0.537203 | −0.72684 | −0.03125 | 0.201603 | 0.930979 |
| | Max | −0.00705 | 1.301237 | 1.30015 | 2.491648 | 0.122389 | 1.218455 | 1.682597 | 2.614402 |
| PCA5 | Min | −2.49874 | −3.23886 | −2.76649 | −4.07782 | −0.9589 | −1.70771 | −1.41474 | −2.02076 |
| | Mean | −0.46655 | −0.94402 | −0.73067 | −1.02591 | −0.15265 | −0.47755 | −0.34837 | −0.70651 |
| | Median | −0.39547 | −0.84381 | −0.69992 | −0.89159 | −0.17176 | −0.40794 | −0.32927 | −0.61785 |
| | Max | 0.404344 | 0.182532 | 0.480085 | −0.10675 | 0.562286 | 0.446026 | 0.347785 | −0.0103 |

Example 3: Design of Zinc Fingers to Bind Genomic Loci in Soybean

Zinc finger proteins directed against the identified DNA sequences of the representative genomic loci were designed as previously described. See, e.g., Urnov et al., (2005) Nature 435:646-551. Exemplary target sequence and recognition helices are shown in Table 7 (recognition helix regions designs) and Table 8 (target sites). In Table 8, nucleotides in the target site that are contacted by the ZFP recognition helices are indicated in uppercase letters and non-contacted nucleotides are indicated in lowercase. Zinc Finger Nuclease (ZFN) target sites were designed for all of the previously described 32 selected optimal genomic loci. Numerous ZFP designs were developed and tested to identify the fingers which bound with the highest level of efficiency with 32 different representative genomic loci target sites which were identified and selected in soybean as described above. The specific ZFP recognition helices (Table 7) which bound with the highest level of efficiency to the zinc finger recognition sequences were used for targeting and integration of a donor sequence within the soybean genome.

TABLE 7 zinc finger designs for the soybean selected genomic loci (N/A indicates "not applicable").

| pDAB Number | ZFP Number | F1 | F2 | F3 | F4 | F5 | F6 |
|---|---|---|---|---|---|---|---|
| 124201 | 391 | SEQ ID NO: 7019 QSANRTK | SEQ ID NO: 7020 HRSSLRR | SEQ ID NO: 7021 QSANRTK | SEQ ID NO: 7022 DSSDRKK | SEQ ID NO: 7023 DRSNRTT | SEQ ID NO: 7024 DNSNRIK |
| | | SEQ ID NO: 7025 RSDNLSV | SEQ ID NO: 7026 QKATRIN | SEQ ID NO: 7027 RSDHLSE | SEQ ID NO: 7028 RNDNRKN | SEQ ID NO: 7029 DRSNRTT | SEQ ID NO: 7030 RKYYLAK |
| 124221 | 411 | SEQ ID NO: 7031 DRSNRTT | SEQ ID NO: 7032 QSAHRIT | SEQ ID NO: 7033 HAQGLRH | SEQ ID NO: 7034 QSGHLSR | SEQ ID NO: 7035 QSGHLSR | N/A |
| | | SEQ ID NO: 7036 QSGSLTR | SEQ ID NO: 7037 RLDWLPM | SEQ ID NO: 7038 RPYTLRL | SEQ ID NO: 7039 DNSNRIK | N/A | N/A |
| 125332 | 651 | SEQ ID NO: 7040 TSGNLTR | SEQ ID NO: 7041 TSGNLTR | SEQ ID NO: 7042 QSGDLTR | SEQ ID NO: 7043 HKWVLRQ | N/A | N/A |
| | | SEQ ID NO: 7044 QSGHLAR | SEQ ID NO: 7045 TSSNRKT | SEQ ID NO: 7046 DSSDRKK | SEQ ID NO: 7047 QSGNLAR | SEQ ID NO: 7048 HNSSLKD | N/A |
| 125309 | 655 | SEQ ID NO: 7049 TSGSLSR | SEQ ID NO: 7050 QLNNLKT | SEQ ID NO: 7051 QSADRTK | SEQ ID NO: 7052 DNSNRIK | SEQ ID NO: 7053 TSGSLSR | SEQ ID NO: 7054 QSGDLTR |
| | | SEQ ID NO: 7055 QSANRTK | SEQ ID NO: 7056 DRSNRTT | SEQ ID NO: 7057 QSGDLTR | SEQ ID NO: 7058 HRSSLLN | N/A | N/A |
| 124884 | 195 | SEQ ID NO: 7059 IDHGRYR | SEQ ID NO: 7060 DRSNLTR | SEQ ID NO: 7061 QSGDLTR | SEQ ID NO: 7062 QSGDLTR | SEQ ID NO: 7063 QRNARTL | N/A |
| | | SEQ ID NO: 7064 TSGNLTR | SEQ ID NO: 7065 DRTGLRS | SEQ ID NO: 7066 SQYTLRD | SEQ ID NO: 7067 TSGHLSR | SEQ ID NO: 7068 RSDHLSE | SEQ ID NO: 7069 QSASRKN |
| 124234 | 424 | SEQ ID NO: 7070 TNQNRIT | SEQ ID NO: 7071 HSNARKT | SEQ ID NO: 7072 QSADRTK | SEQ ID NO: 7073 DNSNRIK | SEQ ID NO: 7074 RSDALTQ | N/A |
| | | SEQ ID NO: 7075 TSGNLTR | SEQ ID NO: 7076 QSNQLRQ | SEQ ID NO: 7077 QSGNLAR | SEQ ID NO: 7078 RQEHRVA | SEQ ID NO: 7079 QSGALAR | SEQ ID NO: 7080 QSGHLSR |
| 124257 | 447 | SEQ ID NO: 7081 QSGSLTR | SEQ ID NO: 7082 WRSCRSA | SEQ ID NO: 7083 QSGNLAR | SEQ ID NO: 7084 WRISLAA | SEQ ID NO: 7085 QKHHLGD | SEQ ID NO: 7086 RSADLSR |
| | | SEQ ID NO: 7087 DRSNRTT | SEQ ID NO: 7088 QSANRTK | SEQ ID NO: 7089 QSANRTK | SEQ ID NO: 7090 DRSNRTT | SEQ ID NO: 7091 QSGNLAR | N/A |
| 125316 | 662 | SEQ ID NO: 7092 QSGNLAR | SEQ ID NO: 7093 TSGNLTR | SEQ ID NO: 7094 DRSNRTT | SEQ ID NO: 7095 QNATRIN | SEQ ID NO: 7096 TSSNRKT | SEQ ID NO: 7097 QSGHLSR |
| | | SEQ ID NO: 7098 DSSTRKT | SEQ ID NO: 7099 QSGNLAR | SEQ ID NO: 7100 RSDVLST | SEQ ID NO: 7101 QSGPLTQ | N/A | N/A |
| 124265 | 455 | SEQ ID NO: 7102 QSGNLAR | SEQ ID NO: 7103 DKSCLPT | SEQ ID NO: 7104 WELNRRT | SEQ ID NO: 7105 TSGNLTR | SEQ ID NO: 7106 DRSNLTR | N/A |
| | | SEQ ID NO: 7107 DRSDLSR | SEQ ID NO: 7108 RREHLRA | SEQ ID NO: 7109 RSDNLAR | SEQ ID NO: 7110 QWNYRGS | SEQ ID NO: 7111 RSHSLLR | SEQ ID NO: 7112 RRDTLLD |
| 124273 | 463 | SEQ ID NO: 7113 QSGDLTR | SEQ ID NO: 7114 QSGNLAR | SEQ ID NO: 7115 HQCCLTS | SEQ ID NO: 7116 RSANLTR | SEQ ID NO: 7117 RSANLAR | SEQ ID NO: 7118 TNQNRIT |
| | | SEQ ID NO: 7119 ATKDLAA | SEQ ID NO: 7120 TSGHLSR | SEQ ID NO: 7121 RSDNLSE | SEQ ID NO: 7122 TSSNRKT | SEQ ID NO: 7123 DRSALAR | SEQ ID NO: 7124 RSDYLAK |
| 124888 | 213 | SEQ ID NO: 7125 rsdnlar | SEQ ID NO: 7126 qsnalnr | SEQ ID NO: 7127 qkgtlge | SEQ ID NO: 7128 qsgsltr | SEQ ID NO: 7129 rsdsllr | SEQ ID NO: 7130 wscclrd |

TABLE 7-continued zinc finger designs for the soybean selected genomic loci (N/A indicates "not applicable").

| pDAB Number | ZFP Number | F1 | F2 | F3 | F4 | F5 | F6 |
|---|---|---|---|---|---|---|---|
| | | SEQ ID NO: 7131 qsgsltr | SEQ ID NO: 7132 drsyrnt | SEQ ID NO: 7133 dqsnlra | SEQ ID NO: 7134 rhshlts | SEQ ID NO: 7135 qsgnlar | N/A |
| 124885 | 215 | SEQ ID NO: 7136 tsgnltr | SEQ ID NO: 7137 lsqdlnr | SEQ ID NO: 7138 rsdslsr | SEQ ID NO: 7139 dssartk | SEQ ID NO: 7140 rsdhlsa | SEQ ID NO: 7141 crrnln |
| | | SEQ ID NO: 7142 seadrsk | SEQ ID NO: 7143 drsnltr | SEQ ID NO: 7144 drsalsr | SEQ ID NO: 7145 tssnrkt | SEQ ID NO: 7146 ergtlar | SEQ ID NO: 7147 drsalar |
| 124610 | 480 | SEQ ID NO: 7148 STDYRYP | SEQ ID NO: 7149 QSGNLAR | SEQ ID NO: 7150 RSDNLSV | SEQ ID NO: 7151 TRWWLPE | SEQ ID NO: 7152 RSDHLSQ | SEQ ID NO: 7153 TRSPLTT |
| | | SEQ ID NO: 7154 TNQSLHW | SEQ ID NO: 7155 QSGNLAR | SEQ ID NO: 7156 RPYTLRL | SEQ ID NO: 7157 QSGSLTR | SEQ ID NO: 7158 RSDVLSE | SEQ ID NO: 7159 TSSNRKT |
| 124614 | 484 | SEQ ID NO: 7160 RSDVLST | SEQ ID NO: 7161 RNSYLIS | SEQ ID NO: 7162 RSANLAR | SEQ ID NO: 7163 TNQNRIT | SEQ ID NO: 7164 RSDNLSV | N/A |
| | | SEQ ID NO: 7165 RSDHLSA | SEQ ID NO: 7166 RSANLTR | SEQ ID NO: 7167 LRHHLTR | SEQ ID NO: 7168 DRSTLRQ | SEQ ID NO: 7169 HNHDLRN | SEQ ID NO: 7170 TSGNLTR |
| 124636 | 506 | SEQ ID NO: 7171 QSANRTT | SEQ ID NO: 7172 QNAHRKT | SEQ ID NO: 7173 QSGNLAR | SEQ ID NO: 7174 QRNHRTT | SEQ ID NO: 7175 QSANRTK | N/A |
| | | SEQ ID NO: 7176 RSDHLSE | SEQ ID NO: 7177 TSGSLTR | SEQ ID NO: 7178 QSGALAR | SEQ ID NO: 7179 QSGHLSR | N/A | N/A |
| 124648 | 518 | SEQ ID NO: 7180 YRWLRNS | SEQ ID NO: 7181 TNSNRKR | SEQ ID NO: 7182 QSANRTT | SEQ ID NO: 7183 HRSSLRR | SEQ ID NO: 7184 RSDVLSA | SEQ ID NO: 7185 QNATRIN |
| | | SEQ ID NO: 7186 RSDSLLR | SEQ ID NO: 7187 QSCARNV | SEQ ID NO: 7188 RPYTLRL | SEQ ID NO: 7189 HRSSLRR | SEQ ID NO: 7190 RSDSLLR | SEQ ID NO: 7191 QSCARNV |
| 121225 | 233 | SEQ ID NO: 7192 QSSDLSR | SEQ ID NO: 7193 YHWYLKK | SEQ ID NO: 7194 QSANRTK | SEQ ID NO: 7195 DNSNRIK | SEQ ID NO: 7196 QSGNLAR | SEQ ID NO: 7197 DRTNLNA |
| | | SEQ ID NO: 7198 RSDNLSE | SEQ ID NO: 7199 TSANLSR | SEQ ID NO: 7200 QSANRTK | SEQ ID NO: 7201 DNSYLPR | SEQ ID NO: 7202 LKQNLDA | SEQ ID NO: 7203 RSHHLKA |
| 121227 | 235 | SEQ ID NO: 7204 RSDHLSQ | SEQ ID NO: 7205 TARLLLL | SEQ ID NO: 7206 RSDNLTR | SEQ ID NO: 7207 QSSDLSR | SEQ ID NO: 7208 YHWYLKK | N/A |
| | | SEQ ID NO: 7209 DRSNLSR | SEQ ID NO: 7210 TSGNLTR | SEQ ID NO: 7211 DRSNRTT | SEQ ID NO: 7212 TNSNRKR | SEQ ID NO: 7213 RSDSLSV | SEQ ID NO: 7214 QNANRKT |
| 121233 | 241 | SEQ ID NO: 7215 TSGNLTR | SEQ ID NO: 7216 QRSHLSD | SEQ ID NO: 7217 RSDNLSE | SEQ ID NO: 7218 VRRALSS | SEQ ID NO: 7219 RSDNLSV | N/A |
| | | SEQ ID NO: 7220 QSSNLAR | SEQ ID NO: 7221 TSGSLTR | SEQ ID NO: 7222 QSGNLAR | SEQ ID NO: 7223 QKVNRAG | SEQ ID NO: 7224 TSGSLSR | SEQ ID NO: 7225 DSSALAK |
| 121235 | 243 | SEQ ID NO: 7226 QSGDLTR | SEQ ID NO: 7227 RKDPLKE | SEQ ID NO: 7228 QSGNLAR | SEQ ID NO: 7229 ATCCLAH | SEQ ID NO: 7230 QSSDLSR | SEQ ID NO: 7231 RRDNLHS |
| | | SEQ ID NO: 7232 QSGNLAR | SEQ ID NO: 7233 HNSSLKD | SEQ ID NO: 7234 QSGALAR | SEQ ID NO: 7235 QSANRTK | SEQ ID NO: 7236 RSDHLST | SEQ ID NO: 7237 RSDHLSR |
| 121238 | 250 | SEQ ID NO: 7238 TSGNLTR | SEQ ID NO: 7239 DSTNLRA | SEQ ID NO: 7240 DRSHLAR | SEQ ID NO: 7241 RSDDLTR | SEQ ID NO: 7242 TSSNRKT | N/A |
| | | SEQ ID NO: 7243 TSGNLTR | SEQ ID NO: 7244 QSGALVI | SEQ ID NO: 7245 QNAHRKT | SEQ ID NO: 7246 LKHHLTD | SEQ ID NO: 7247 RSDNLST | SEQ ID NO: 7248 DRSNRKT |
| 121246 | 259 | SEQ ID NO: 7249 DRSALSR | SEQ ID NO: 7250 RSDALTQ | SEQ ID NO: 7251 DRSTRTK | SEQ ID NO: 7252 QSGNLHV | SEQ ID NO: 7253 RSDNLTR | N/A |
| | | SEQ ID NO: 7254 DRSNLSR | SEQ ID NO: 7255 QSGNLAR | SEQ ID NO: 7256 RSDSLLR | SEQ ID NO: 7257 WLSSLSA | N/A | N/A |
| 121249 | 262 | SEQ ID NO: 7258 RSDNLST | SEQ ID NO: 7259 DSSSRIK | SEQ ID NO: 7260 QSGALAR | SEQ ID NO: 7261 QSGNLHV | SEQ ID NO: 7262 RSDVLST | SEQ ID NO: 7263 RYAYLTS |

TABLE 7-continued zinc finger designs for the soybean selected genomic loci (N/A indicates "not applicable").

| pDAB Number | ZFP Number | F1 | F2 | F3 | F4 | F5 | F6 |
|---|---|---|---|---|---|---|---|
| | | SEQ ID NO: 7264 RSDNLSE | SEQ ID NO: 7265 TRSPLRN | SEQ ID NO: 7266 QNAHRKT | SEQ ID NO: 7267 RSDHLSE | SEQ ID NO: 7268 RNDNRKN | N/A |
| 125324 | 670 | SEQ ID NO: 7269 QRTNLVE | SEQ ID NO: 7270 ASKTRTN | SEQ ID NO: 7271 RSANLAR | SEQ ID NO: 7272 RSDHLTQ | SEQ ID NO: 7273 RSAHLSR | N/A |
| | | SEQ ID NO: 7274 RSDNLSV | SEQ ID NO: 7275 QNANRIT | SEQ ID NO: 7276 DQSNLRA | SEQ ID NO: 7277 QNAHRKT | SEQ ID NO: 7278 RSAHLSR | N/A |
| 121265 | 282 | SEQ ID NO: 7279 DRSALAR | SEQ ID NO: 7280 RSDYLAK | SEQ ID NO: 7281 RSDDLSR | SEQ ID NO: 7282 RNDNRKK | SEQ ID NO: 7283 RSDHLST | SEQ ID NO: 7284 HSNTRKN |
| | | SEQ ID NO: 7285 RSDVLSE | SEQ ID NO: 7286 QRSNLKV | SEQ ID NO: 7287 QSSNLAR | SEQ ID NO: 7288 QSGHLSR | N/A | N/A |
| 121271 | 288 | SEQ ID NO: 7289 DRSDLSR | SEQ ID NO: 7290 LRFNLRN | SEQ ID NO: 7291 RSDSLSV | SEQ ID NO: 7292 QNANRKT | N/A | N/A |
| | | SEQ ID NO: 7293 QSGDLTR | SEQ ID NO: 7294 TSGSLTR | SEQ ID NO: 7295 RSDDLTR | SEQ ID NO: 7296 YRWLLRS | SEQ ID NO: 7297 QSGDLTR | N/A |
| 124666 | 538 | SEQ ID NO: 7298 RSDNLST | SEQ ID NO: 7299 AACNRNA | SEQ ID NO: 7300 RPYTLRL | SEQ ID NO: 7301 QSGSLTR | SEQ ID NO: 7302 SQYTLRD | SEQ ID NO: 7303 TSGHLSR |
| | | SEQ ID NO: 7304 QSANRTK | SEQ ID NO: 7305 DRSNRTT | SEQ ID NO: 7306 RSDVLST | SEQ ID NO: 7307 CRRNLRN | N/A | N/A |
| 124814 | 598 | SEQ ID NO: 7308 QSGDLTR | SEQ ID NO: 7309 HRSSLLN | SEQ ID NO: 7310 TNQSLHW | SEQ ID NO: 7311 QSGNLAR | SEQ ID NO: 7312 QSGNLAR | N/A |
| | | SEQ ID NO: 7313 RSCCLHL | SEQ ID NO: 7314 RNASRTR | SEQ ID NO: 7315 QSGNLAR | SEQ ID NO: 7316 RQEHRVA | SEQ ID NO: 7317 RSDNLSE | SEQ ID NO: 7318 TSSNRKT |
| 124690 | 560 | SEQ ID NO: 7319 RSDVLSE | SEQ ID NO: 7320 QRSNLKV | SEQ ID NO: 7321 QSGALAR | SEQ ID NO: 7322 YRWLRNS | SEQ ID NO: 7323 QSANRTT | SEQ ID NO: 7324 DRSNRTT |
| | | SEQ ID NO: 7325 QNAHRKT | SEQ ID NO: 7326 LAHHLVQ | SEQ ID NO: 7327 HAQGLRH | SEQ ID NO: 7328 QSGHLSR | SEQ ID NO: 7329 RSDDLTR | SEQ ID NO: 7330 RRFTLSK |
| 124815 | 599 | SEQ ID NO: 7331 RSDNLSE | SEQ ID NO: 7332 KSWSRYK | SEQ ID NO: 7333 RSAHLSR | SEQ ID NO: 7334 RSDDLTR | SEQ ID NO: 7335 YSWTLRD | SEQ ID NO: 7336 TSGNLTR |
| | | SEQ ID NO: 7337 RSDVLST | SEQ ID NO: 7338 DNSSRTR | SEQ ID NO: 7339 RSDALAR | SEQ ID NO: 7340 RSDSLSA | SEQ ID NO: 7341 DRSDLSR | N/A |
| 124816 | 600 | SEQ ID NO: 7342 GTQGLGI | SEQ ID NO: 7343 DRSNLTR | SEQ ID NO: 7344 RNDDRKK | SEQ ID NO: 7345 RSDVLSE | SEQ ID NO: 7346 RSSDRTK | N/A |
| | | SEQ ID NO: 7347 QSANRTK | SEQ ID NO: 7348 DSSHRTR | SEQ ID NO: 7349 QSANRTK | SEQ ID NO: 7350 SVGNLNQ | SEQ ID NO: 7351 TSGNLTR | N/A |
| 124842 | 631 | SEQ ID NO: 7352 TNQNRIT | SEQ ID NO: 7353 HSNARKT | SEQ ID NO: 7354 QSSHLTR | SEQ ID NO: 7355 RLDNRTA | SEQ ID NO: 7356 QSGNLAR | SEQ ID NO: 7357 QGANLIK |
| | | SEQ ID NO: 7358 RSDNLST | SEQ ID NO: 7359 QKSPLNT | SEQ ID NO: 7360 QSSDLSR | SEQ ID NO: 7361 QSSDLSR | SEQ ID NO: 7362 YHWYLK | N/A |
| 125338 | 37 | SEQ ID NO: 7574 TSSNRKT | SEQ ID NO: 7575 RSDELRG | SEQ ID NO: 7576 RSDTLSA | SEQ ID NO: 7577 DKSTRTK | N/A | N/A |
| | | SEQ ID NO: 7578 DRSTRTK | SEQ ID NO: 7579 QSGNLHV | SEQ ID NO: 7580 QNAHRKT | SEQ ID NO: 7581 QSANRTK | SEQ ID NO: 7582 TSGSLSR | SEQ ID NO: 7583 FYMQLSR |

TABLE 8

Zinc finger target site of soybean selected genomic loci

| Locus ID Name | pDAB Number | ZFP Number and Binding Sites (5'→3') |
|---|---|---|
| OGL01soy_ogl_308 | 124201 | 391 SEQ ID NO: 7363 TGGTACTAGGGGAT TACTATTCCTAAGAAAG TTAAA SEQ ID NO: 7364 |

TABLE 8-continued

Zinc finger target site of soybean selected genomic loci

| Locus ID Name | pDAB Number | ZFP Number and Binding Sites (5'→3') | |
|---|---|---|---|
| OGL02soy_ogl_ 307 | 124221 411 | SEQ ID NO: 7365 GGAGGAATTTAG ATAC | SEQ ID NO: 7366 TACTTGCTGGTA |
| OGL03soy_ogl_ 2063 | 125305 651 | SEQ ID NO: 7367 ATCATCTGCAAA | SEQ ID NO: 7368 CTTGAATTCCTATGG A |
| OGL04soy_ogl_ 1906 | 125309 655 | SEQ ID NO: 7369 AACTTGTGAGTA AACTGC | SEQ ID NO: 7370 ATTGCATAATAA |
| OGL05soy_ogl_ 262 | 124884 195 | SEQ ID NO: 7371 GTTGTCTTGCTGC TAT | SEQ ID NO: 7372 ACACAGGGTATCTTC GAT |
| OGL06soy_ogl_ 5227 | 124234 424 | SEQ ID NO: 7373 ATGTACTCATATT CAT | SEQ ID NO: 7374 GGAGTAAGGGAAAA AGAT |
| OGL07soy_ogl_ 4074 | 124257 447 | SEQ ID NO: 7375 GCTCGTCATTGAA TTGTGTA | SEQ ID NO: 7376 GAAAAATAATTAAT AC |
| OGL08soy_ogl_ 3481 | 125316 662 | SEQ ID NO: 7377 GGATATATAAAC GATGAA | SEQ ID NO: 7378 ATAATGGAACCC |
| OGL09soy_ogl_ 1016 | 124265 455 | SEQ ID NO: 7379 GACGATCACCTC GAA | SEQ ID NO: 7380 CCGGTGTCAGAGAG GGCC |
| OGL10soy_ogl_ 937 | 124273 463 | SEQ ID NO: 7381 AATGAGAGAGAG AGAAGCA | SEQ ID NO: 7382 CAGATCAATCAGGG TCCC |
| OGL11soy_ogl_ 5109 | 124888 213 | SEQ ID NO: 7383 CTCTACATGGTAC CACTCG | SEQ ID NO: 7384 GAAAGGCACCTCGT A |
| OGL12soy_ogl_ 6801 | 124885 215 | SEQ ID NO: 7385 ATCAGCCACGAT CCTGCA | SEQ ID NO: 7386 GTCGCCCATGTCTGA CTCA |
| OGL13soy_ogl_ 6636 | 124610 480 | SEQ ID NO: 7387 CTATAGTTTTAAG TGAATTA | SEQ ID NO: 7388 TATATGGTATTGGAA ATT |
| OGL14soy_ogl_ 4665 | 124614 484 | SEQ ID NO: 7389 CATCGTCTCATGC TT | SEQ ID NO: 7390 GATCCTACAAGTGA GAGG |
| OGL15soy_ogl_ 6189 | 124636 506 | SEQ ID NO: 7391 TTTTCTTTCTCTT TA | SEQ ID NO: 7392 GGAGTAGTTAGG |
| OGL16soy_ogl_ 4222 | 124648 518 | SEQ ID NO: 7393 AACATCTTTAACT CATTGT | SEQ ID NO: 7394 ATAGTGGTTTTGCAT AGTG |
| OGL17soy_ogl_ 2543 | 121225 233 | SEQ ID NO: 7395 CACGAAAAACTA AATTTGCT | SEQ ID NO: 7396 AGGTATTTCTAAGAT AGG |
| OGL18soy_ogl_ 310 | 121227 235 | SEQ ID NO: 7397 TTTGCTGAGTGAA GG | SEQ ID NO: 7398 CAAATGTGATAACTG ATGAC |
| OGL19soy_ogl_ 2353 | 121233 241 | SEQ ID NO: 7399 AAGATGAAGCGA GAT | SEQ ID NO: 7400 ATCGTTCAAGAAGTT GAA |
| OGL20soy_ogl_ 1894 | 121235 243 | SEQ ID NO: 7401 CAGGCTGGCAAA ATGGAA | SEQ ID NO: 7402 GGGTGGTAAGTACTT GAA |
| OGL22soy_ogl_ 3218 | 121238 250 | SEQ ID NO: 7403 AATGCGTGGCCA CGAT | SEQ ID NO: 7404 AACTAGCGTAGAGT AGAT |
| OGL24soy_ogl_ 3333 | 121246 259 | SEQ ID NO: 7405 GAGAAAGCCATG GTC | SEQ ID NO: 7406 TGTGTGGAAGAC |
| OGL25soy_ogl_ 2546 | 121249 262 | SEQ ID NO: 7407 TGGATGTCAAGT ATTCAAG | SEQ ID NO: 7408 TAGGGGAGAATACA G |
| OGL28soy_ogl_ 5957 | 125324 670 | SEQ ID NO: 7409 GGGAGGGAGACC CAA | SEQ ID NO: 7410 GGGAGAAACAAAAA G |
| OGL30soy_ogl_ 3818 | 121265 282 | SEQ ID NO: 7411 GTTTGGTTAGGCG CAGATC | SEQ ID NO: 7412 GGAGAAACAACTG |
| OGL31soy_ogl_ 5551 | 121271 288 | SEQ ID NO: 7413 AAAGTGTCATGC C | SEQ ID NO: 7414 GCAATTGCGGTTGCA |
| OGL33optimal_ loci_ 1098 | 124666 538 | SEQ ID NO: 7415 GGTATCGTATTGC ATTAG | SEQ ID NO: 7416 CGCACGTAATAA |
| OGL34optimal_ loci_ 97772 | 124814 598 | SEQ ID NO: 7417 GAAGAAATTATT GCA | SEQ ID NO: 7418 AATCAGAGGGAAGT GAGA |
| OGL35optimal_ loci_ 236662 | 124690 560 | SEQ ID NO: 7419 AACTAACTTGTA ACAACTG | SEQ ID NO: 7420 TTGGCGGGAATTAGT AGA |
| OGL36optimal_ loci_ 139485 | 124815 599 | SEQ ID NO: 7421 GATCTTGCGGGG TAGCAG | SEQ ID NO: 7422 GACCTGGTGGTCATG |

TABLE 8-continued

Zinc finger target site of soybean selected genomic loci

| Locus ID Name | pDAB Number | ZFP Number and Binding Sites (5'→3') | |
|---|---|---|---|
| OGL37optimal_ loci_ 301175 | 125338 | 627 SEQ ID NO: 7584 ATACGTCAGGGTt antgGTTGTTTAA TGAAAAGCC | OGL37 |
| OGL38optimal_ loci_ 152337 | 124816 | 600 SEQ ID NO: 7423 TCTATGTCGGACTA TT | SEQ ID NO: 7424 GATCATTTAAGGATA |
| OGL39optimal_ loci_ 202616 | 124842 | 631 SEQ ID NO: 7425 ATGAATTCCCTTT TCTTA | SEQ ID NO: 7426 TTTGCTGCTTTATAG |

The soybean representative genomic loci zinc finger designs were incorporated into zinc finger expression vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid ZC linker and an opaque-2 nuclear localization signal optimized for soybean to form zinc-finger nucleases (ZFNs). See, U.S. Pat. No. 7,888,121. Zinc fingers for the various functional domains were selected for in vivo use. Of the numerous ZFNs that were designed, produced and tested to bind to the putative genomic target site, the ZFNs described in Table 8 above were identified as having in vivo activity and were characterized as being capable of efficiently binding and cleaving the unique soybean genomic polynucleotide target sites in planta.

ZFN Construct Assembly

Plasmid vectors containing ZFN gene expression constructs were designed and completed using skills and techniques commonly known in the art (see, for example, Ausubel or Maniatis). Each ZFN-encoding sequence was fused to a sequence encoding an opaque-2 nuclear localization signal (Maddaloni et al., (1989) Nuc. Acids Res. 17:7532), that was positioned upstream of the zinc finger nuclease. The non-canonical zinc finger-encoding sequences were fused to the nuclease domain of the type IIS restriction enzyme FokI (amino acids 384-579 of the sequence of Wah et al. (1998) Proc. Natl. Acad. Sci. USA 95:10564-10569). Expression of the fusion proteins was driven by a strong constitutive promoter from the Cassava vein mosaic virus. The expression cassette also includes a 3' UTR from the Agrobacterium tumefaciens ORF23. The self-hydrolyzing 2A encoding the nucleotide sequence from Thosea asigna virus (Szymczak et al., (2004) Nat Biotechnol. 22:760-760) was added between the two Zinc Finger Nuclease fusion proteins that were cloned into the construct.

The plasmid vectors were assembled using the IN-FUSION™ Advantage Technology (Clontech, Mountain View, Calif.). Restriction endonucleases were obtained from New England BioLabs (Ipswich, Mass.) and T4 DNA Ligase (Invitrogen, Carlsbad, Calif.) was used for DNA ligation. Plasmid preparations were performed using NUCLEO-SPIN® Plasmid Kit (Macherey-Nagel Inc., Bethlehem, Pa.) or the Plasmid Midi Kit (Qiagen) following the instructions of the suppliers. DNA fragments were isolated using QIA-QUICK GEL EXTRACTION KIT™ (Qiagen) after agarose tris-acetate gel electrophoresis. Colonies of all ligation reactions were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.). Plasmids were constructed and confirmed via restriction enzyme digestion and via DNA sequencing.

Zinc Finger Cloning Via Automated Workflow

A subset of Zinc Finger Nuclease vectors were cloned via an automated DNA construction pipeline. Overall, the automated pipeline resulted in vector constructions with identical ZFN architecture as described previously. Each Zinc Finger monomer, which confers the DNA binding specificity of the ZFN, were divided into 2-3 unique sequences at a KPF amino acid motif. Both the 5' and 3' ends of the ZFN fragments were modified with inclusion of a BsaI recognition site (GGTCTCN) and derived overhangs. Overhangs were distributed such that a 6-8 part assembly would only result in the desired full length expression clone. Modified DNA fragments were synthesized de novo (Synthetic Genomics Incorporated, La Jolla, Calif.). A single dicot backbone, pDAB118796 was used in all of the soybean ZFN builds. It contained the Cassava Mosaic Virus promoter and the Opaque2 NLS as well as the FokI domain and the Orf23 3'UTR from Agrobacterium tumefaciens. Cloned in between the Opaque 2 NLS and the FokI domain was a BsaI flanked SacB gene from Bacillus subtilis. When putative ligation events were plated on Sucrose containing media, the SacB cassette acts as a negative selection agent reducing or eliminating vector backbone contamination. A second part repeatedly utilized in all builds was pDAB117443. This vector contains the first monomer FokI domain, the T2A stutter sequence, and the $2^{nd}$ monomer Opaque2 NLS all flanked by BsaI sites.

Using these materials as the ZFN DNA parts library, a Freedom Evo 150® (TECAN, Mannedorf, Switzerland) manipulated the addition of 75-100 ng of each DNA plasmid or synthesized fragment from 2D bar coded tubes into a PCR plate (ThermoFisher, Waltham, Mass.). BsaI (NEB, Ipswich, Mass.) and T4 DNA ligase (NEB, Ipswich, Mass.) supplemented with Bovine Serum Albumin protein (NEB, Ipswich, Mass.) and T4 DNA Ligase Buffer (NEB, Ipswich, Mass.) were added to the reaction. Reactions were cylcled (25×) with incubations for 3 minutes at 37° C. and 4 minutes at 16° C. C1000 Touch Thermo Cycler® (BioRad, Hercules Calif.). Ligated material was transformed and screened in Top10 Cells® (Life Technologies Carlsbad, Calif.) by hand or using a Qpix460 colony picker and LabChip GX® (Perkin Elmer, Waltham, Mass.). Correctly digesting colonies were sequence confirmed provided to plant transformation.

Universal Donor Construct Assembly

To support rapid testing of a large number of target loci, a novel, flexible universal donor system sequence was designed and constructed. The universal donor polynucleotide sequence was compatible with high throughput vector construction methodologies and analysis. The universal donor system was composed of at least three modular domains: a variable ZFN binding domain, a non-variable analytical and user defined features domain, and a simple plasmid backbone for vector scale up. The non-variable universal donor polynucleotide sequence was common to all donors and permits design of a finite set of assays that can be used across all of the soybean target sites thus providing uniformity in targeting assessment and reducing analytical cycle times. The modular nature of these domains allowed for high throughput donor assembly. Additionally, the universal donor polynucleotide sequence has other unique features aimed at simplifying downstream analysis and enhancing the interpretation of results. It contained an asymmetric restriction site sequence that allows the digestion of PCR products into diagnostically predicted sizes. Sequences comprising secondary structures that were expected to be problematic in PCR amplification were removed. The universal donor polynucleotide sequence was small in size (less than 3.0 Kb). Finally, the universal donor polynucleotide sequence was built upon the high copy pUC19 backbone that allows a large amount of test DNA to be bulked in a timely fashion.

Figure 7:
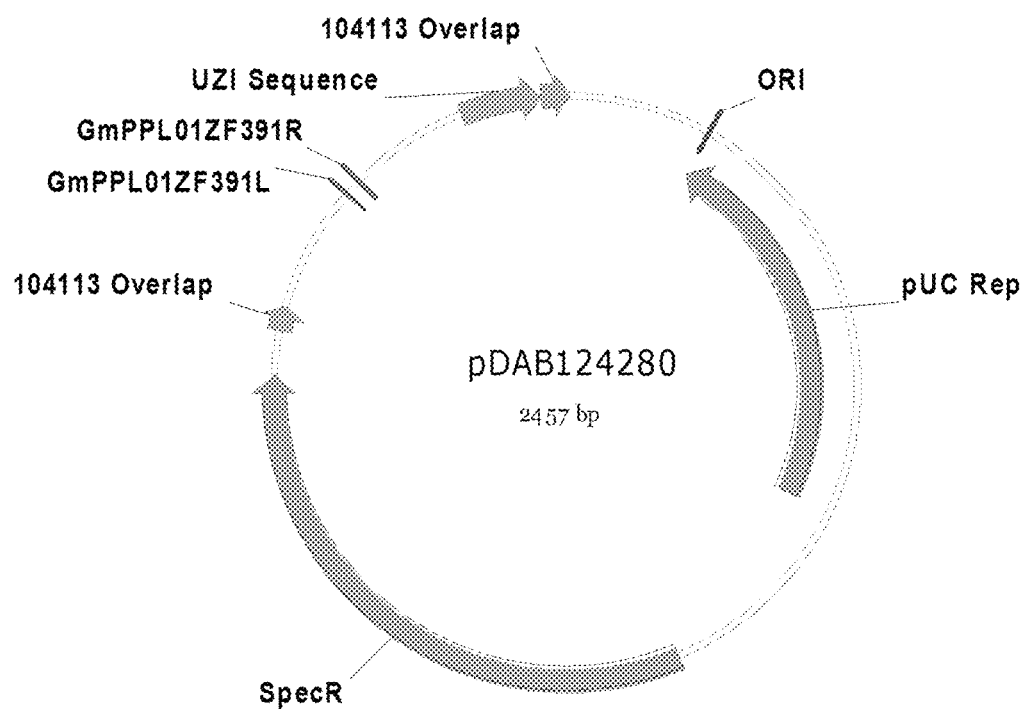
FIG. 7. Plasmid map of pDAB124280 (SEQ ID NO:7561). The numbered elements (i.e., GmPPL01ZF391R and GMPPL01ZF391L) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 8:
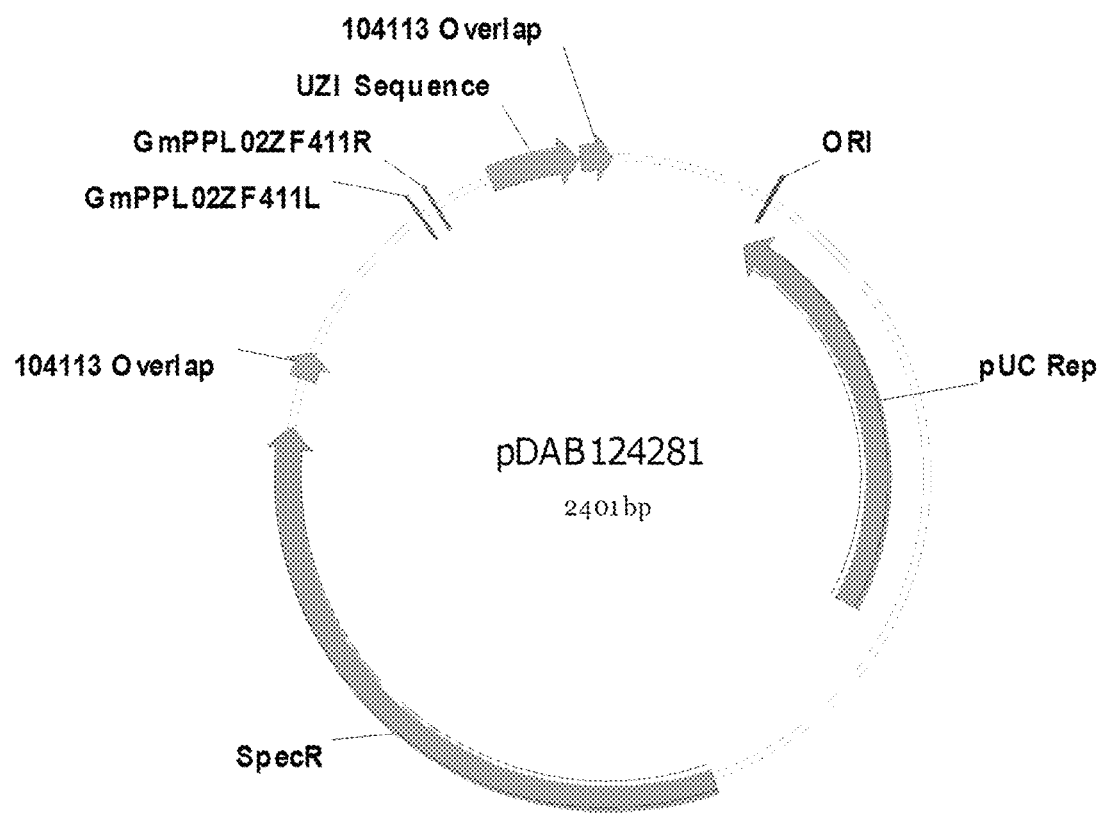
FIG. 8. Plasmid map of pDAB124281 (SEQ ID NO:7562). The numbered elements (i.e., GmPPL02ZF411R and GMPPL02ZF411L) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 9:
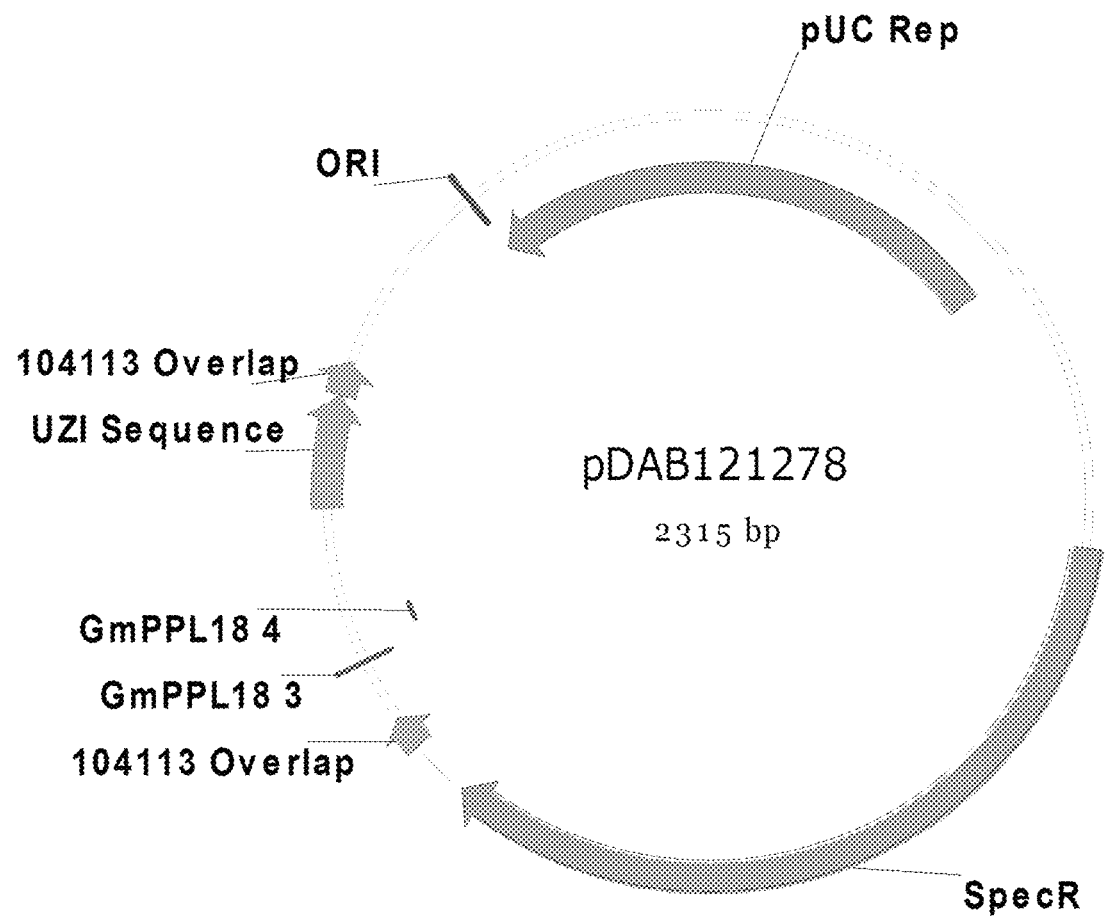
FIG. 9. Plasmid map of pDAB121278 (SEQ ID NO:7563). The numbered elements (i.e., GmPPL18_4 and GMPPL18_3) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 10:
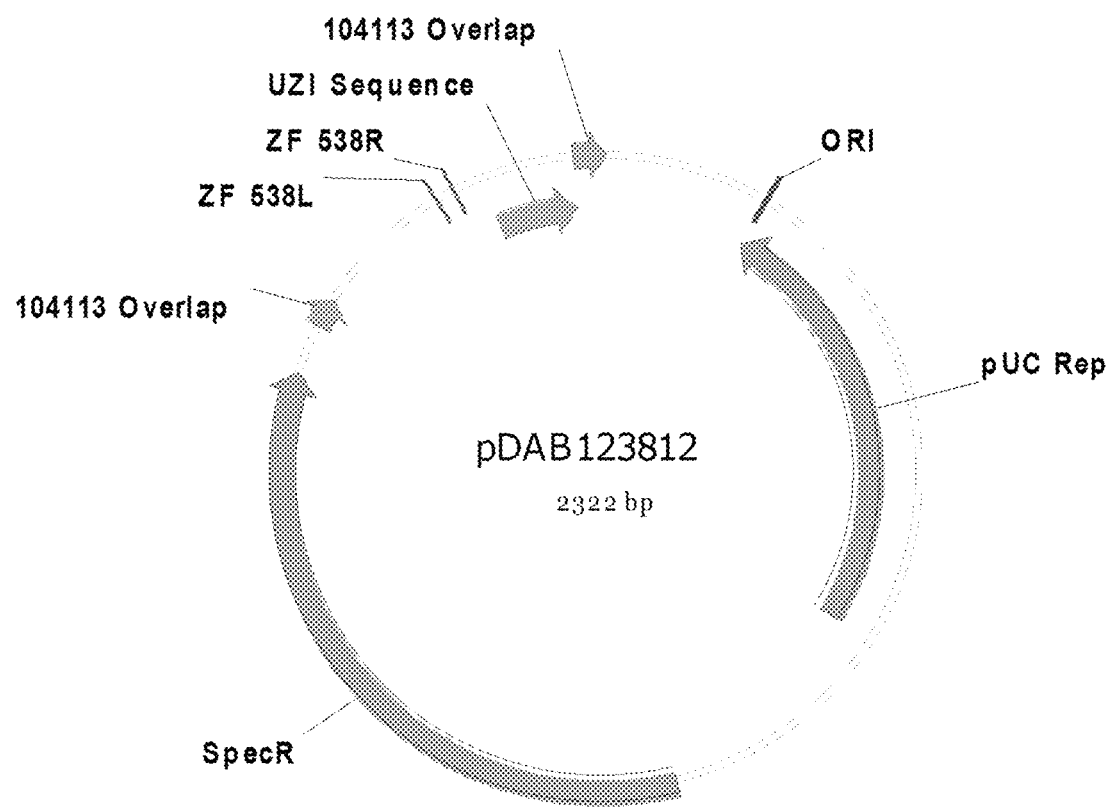
FIG. 10. Plasmid map of pDAB123812 (SEQ ID NO:7564). The numbered elements (i.e., ZF538R and ZF538L) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 11:
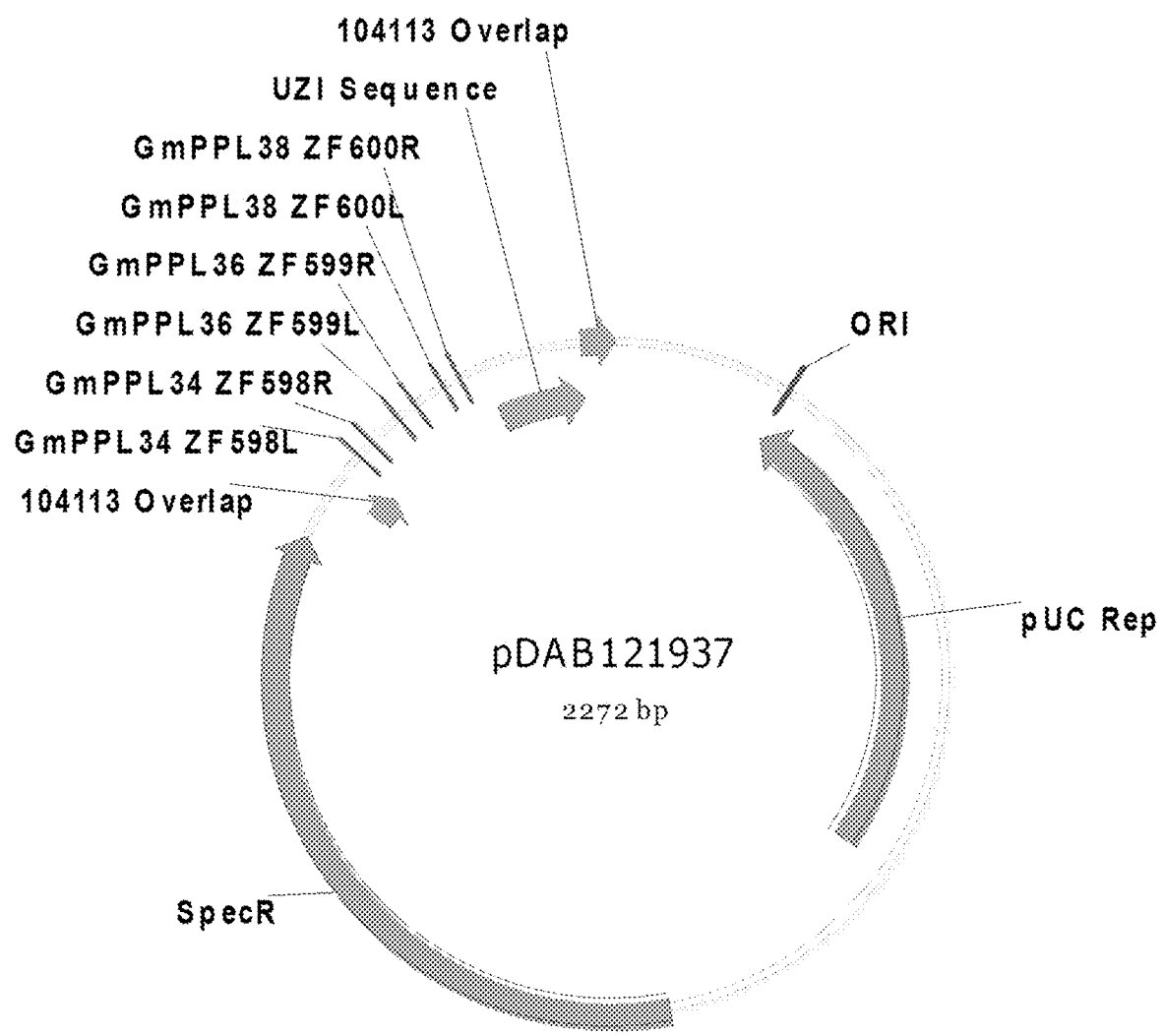
FIG. 11. Plasmid map of pDAB121937 (SEQ ID NO:7565). The numbered elements (i.e., GmPPL34ZF598L, GmPPL34ZF598R, GmPPL36ZF599L, GmPPL36ZF599R, GmPPL36ZF600L, and GmPPL36ZF600R) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 12:
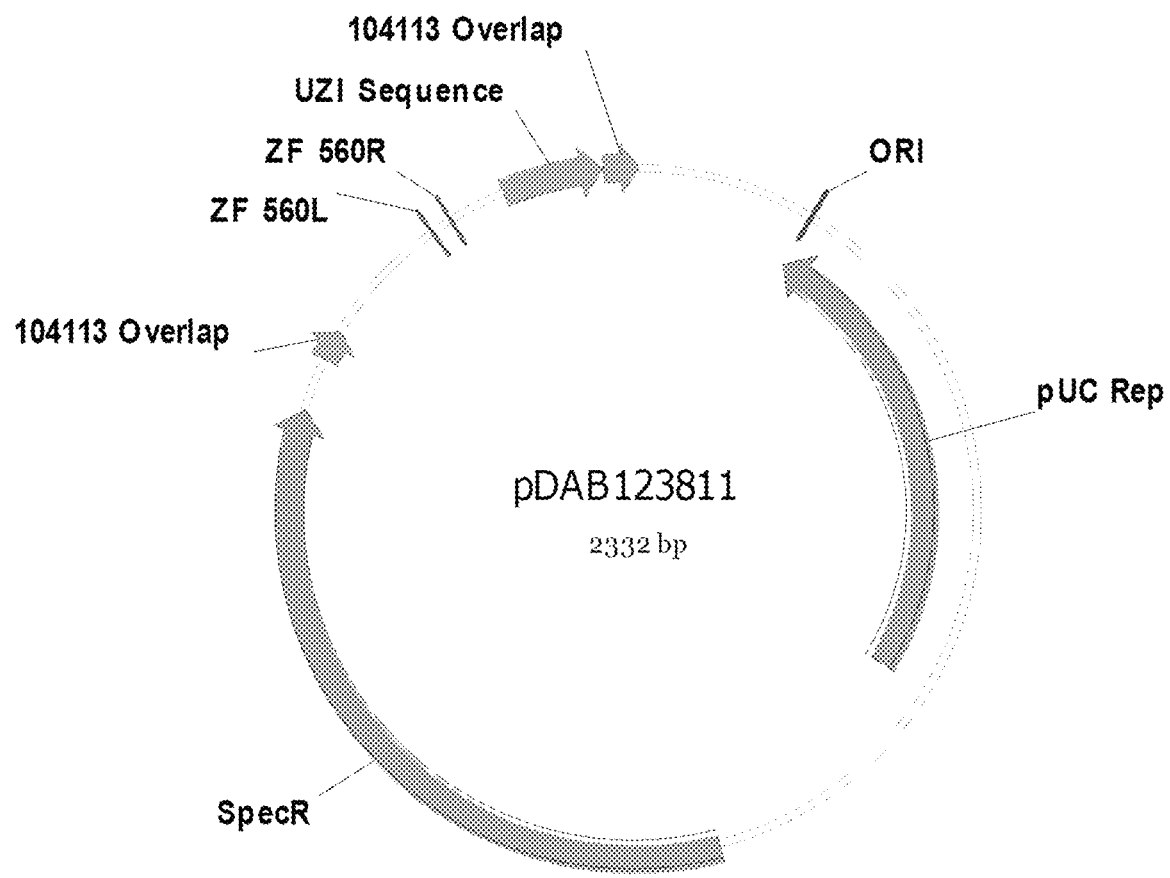
FIG. 12. Plasmid map of pDAB123811 (SEQ ID NO:7566). The numbered elements (i.e., ZF 560L and ZF 560R) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 13:
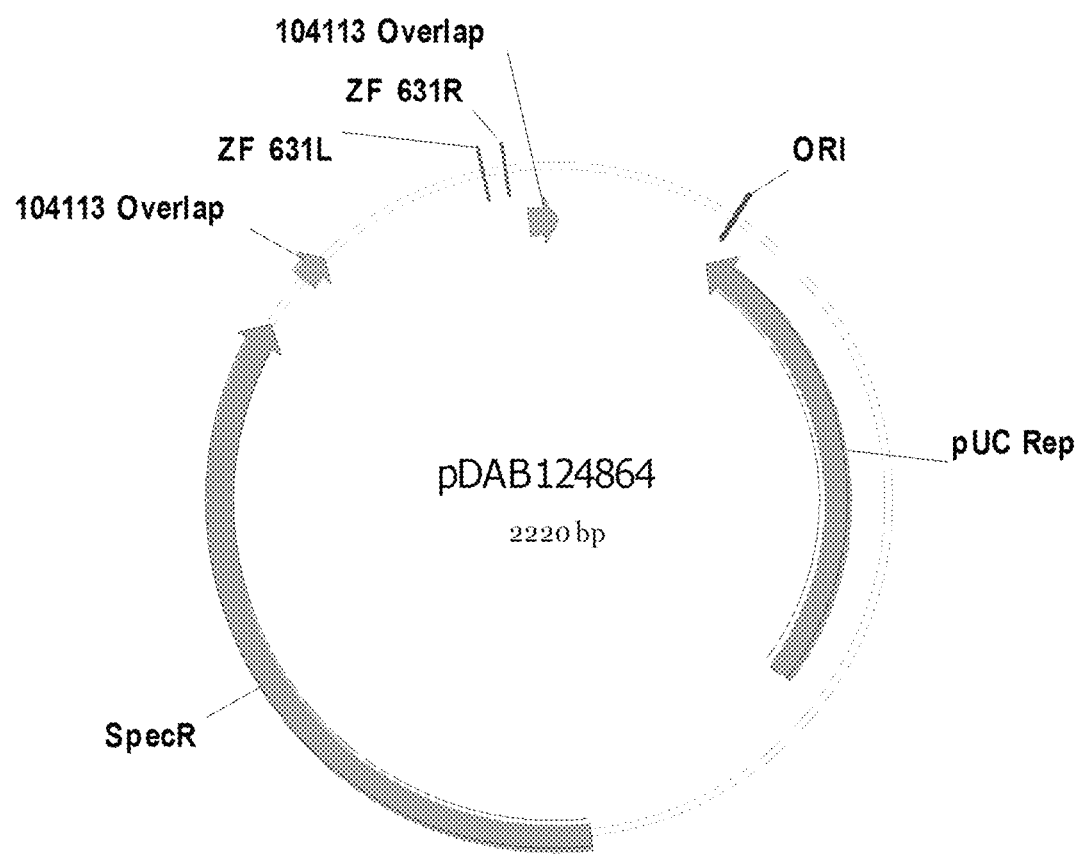
FIG. 13. Plasmid map of pDAB124864 (SEQ ID NO:7567). The numbered elements (i.e., ZF631L and ZF631R) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).

As an embodiment, an example plasmid comprising a universal donor polynucleotide sequence is provided as pDAB124280 (SEQ ID NO:7561 and FIG. 7). In an additional embodiment, a universal donor polynucleotide sequence is provided as: pDAB124281, SEQ ID NO:7562, FIG. 8; pDAB121278, SEQ ID NO:7563, FIG. 9; pDAB123812, SEQ ID NO:7564 FIG. 10; pDAB121937, SEQ ID NO:7565, FIG. 11; pDAB123811, SEQ ID NO:7566, FIG. 12; and, pDAB124864 SEQ ID NO:7567, FIG. 13. In another embodiment, additional sequences comprising the universal donor polynucleotide sequence with functionally expressing coding sequence or nonfunctional (promoterless) expressing coding sequences can be constructed (Table 11).

TABLE 11

The various universal domain sequences that were transformed into the plant cell protoplasts for donor mediated integration within the genome of soybean are provided. The various elements of the universal domain plasmid system are described and identified by base pair position in the accompanying SEQ ID NO:. "N/A" meas not applicable.

| Vector Name | ZFN binding domain | Analytical domain | Plasmid backbone | SEQ ID NO: |
|---|---|---|---|---|
| pDAB124280 | 1955-2312 bp | 2313-2422 bp | 2423-1954 bp | A1 |
| pDAB124281 | 1955-2256 bp | 2257-2366 bp | 2367-1954 bp | A2 |
| pDAB121278 | 1509-1724 bp | 1725-1834 bp | 1835-1508 bp | A3 |
| pDAB123812 | 1955-2177 bp | 2178-2287 bp | 2288-1954 bp | A4 |
| pDAB121937 | 1955-2127 bp | 2128-2237 bp | 2238-1954 bp | A5 |
| pDAB123811 | 1955-2187 bp | 2288-2297 bp | 2298-1954 bp | A6 |
| pDAB124864 | 1952-2185 | N/A | 2186-1951 bp | A7 |

Figure 4:
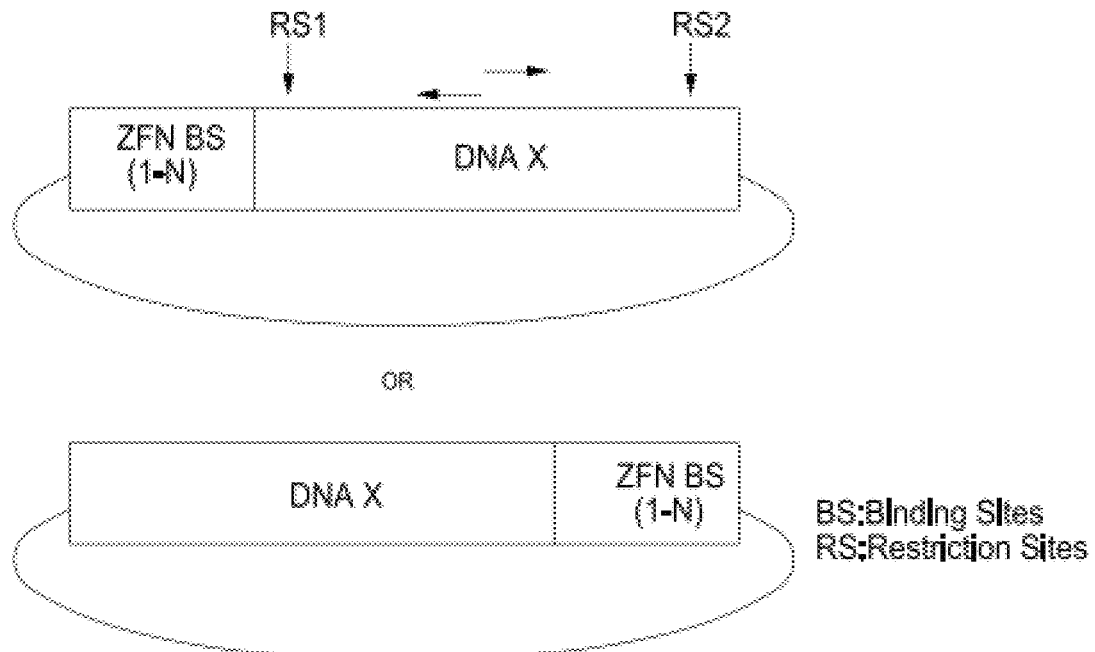
FIG. 4. Representation of the universal donor polynucleotide sequence for integration via non-homologous end joining (NHEJ). Two proposed vectors are provide wherein a DNA of interest (DNA X) comprises one or more (i.e., "1-N") zinc finger binding sites (ZFN BS) at either end of the DNA of interest. Vertical arrows show unique restriction sites and horizontal arrows represent potential PCR primer sites.
Figure 5:
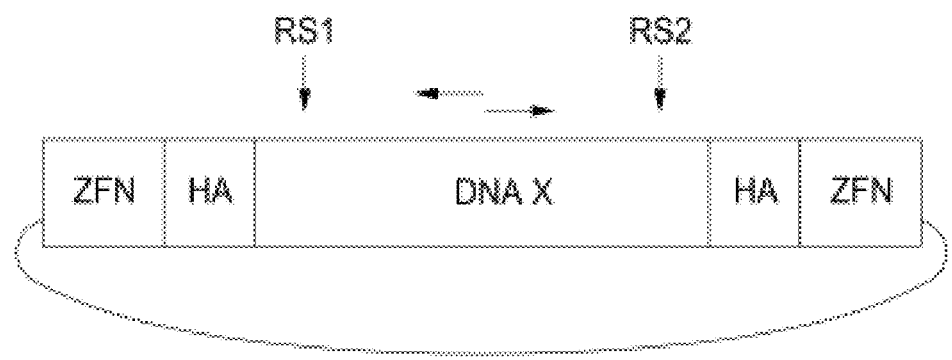
FIG. 5. Representation of the universal donor polynucleotide sequence for integration via homologous-directed repair (HDR). A DNA of interest (DNA X) comprising two regions of homologous sequences (HA) flanking the DNA of interest with zinc finger nuclease binding sites (ZFN) bracketing the DNAX and HA sequences. Vertical arrows show unique restriction sites and horizontal arrows represent potential PCR primer sites.

The universal donor polynucleotide sequence was a small 2-3 Kb modular donor system delivered as a plasmid. This was a minimal donor, comprising 1, 2, 3, 4, 5, 6, 7, 8, 9, or more ZFN binding sites, a short 100-150 bp template region referred to as "DNA X" or "UZI Sequence" (SEQ ID NO:7568) that carries restriction sites and DNA sequences for primer design or coding sequences, and a simple plasmid backbone (FIG. 4). The entire plasmid was inserted through NHEJ following DNA double strand breaks at the appropriate ZFN binding site; the ZFN binding sites can be incorporated tandemly. This embodiment of a universal donor polynucleotide sequence was most suitable for rapid screening of target sites and ZFNs, and sequences that were difficult to amplify were minimized in the donor. Universal donors without the "UZI" sequence but carrying one or more ZFN sites have also been generated In a further embodiment the universal donor polynucleotide sequence was made up of at least 4 modules and carries ZFN binding sites, homology arms, DNA X with either just the approximately 100 bp analytical piece or coding sequences. This embodiment of the universal donor polynucleotide sequence was suitable for interrogating HDR mediated gene insertion at a variety of target sites, with several ZFNs (FIG. 5).

The universal donor polynucleotide sequence can be used with all targeting molecules with defined DNA binding domains, with two modes of targeted donor insertion (NHEJ/HDR). As such, when the universal donor polynucleotide sequence was co-delivered with the appropriate ZFN expression construct, the donor vector and the soybean genome was cut in one specific location dictated by the binding of the particular ZFN. Once linearized, the donor can be incorporated into the genome by NHEJ or HDR. The different analytical considerations in the vector design can then be exploited to determine the Zinc Finger which maximizes the efficient delivery of targeted integration.

Example 4: Soybean Transformation Procedures

Before delivery to *Glycine max* c.v. Maverick protoplasts, plasmid DNA for each ZFN construct was prepared from cultures of *E. coli* using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Protoplast Isolation

Protoplasts were isolated from a Maverick suspension culture derived from callus produced from leaf explants. Suspensions were subcultured every 7 days in fresh LS medium (Linsmaier and Skoog 1965) containing 3% (w/v) sucrose, 0.5 mg/L 2,4-D, and 7 g of bactoagar, pH 5.7 For isolation, thirty milliliters of a Maverick suspension culture 7 days post subculturing was transferred to a 50 ml conical tube and centrifuged at 200 g for 3 minutes, yielding about 10 ml of settled cell volume (SCV) per tube. The supernatant was removed and twenty milliliters of the enzyme solution (0.3% pectolyase (320952; MP Biomedicals), 3% cellulase ("Onozuka" R10™; Yakult Pharmaceuticals, Japan) in MMG solution (4 mM MES, 0.6 M mannitol, 15 mM $MgCl_2$, pH 6.0) was added for every 4 SCV of suspension cells and the tubes were wrapped with Parafilm™. The tubes were placed on a platform rocker overnight (about 16-18 hr) and an aliquot of the digested cells was viewed microscopically to ensure the digestion of the cell wall was sufficient.

Protoplast Purification

Thirty milliliters of a soybean c.v. Maverick suspension culture 7 days post subculturing was transferred to a 50 ml conical centrifuge tube and centrifuged at 200 g for 3 minutes, yielding about 10 ml of settled cell volume (SCV) per tube. The supernatant was removed without disturbing the cell pellet. Twenty milliliters of the enzyme solution (0.3% pectolyase (320952; MP Biomedicals), 3% cellulase ("Onozuka" R10™; Yakult Pharmaceuticals, Japan) in MMG solution (4 mM MES, 0.6 M mannitol, 15 mM MgCl$_2$, pH 6.0) was added for every 4 SCV of suspension cells and the tubes were wrapped with Parafilm™. The tubes were placed on a platform rocker overnight (about 16-18 hr). The next morning, an aliquot of the digested cells was viewed microscopically to ensure the digestion of the cell walls was sufficient.

Protoplast Purification

The cells/enzyme solutions were filtered slowly through a 100 μM cell strainer. The cell strainer was rinsed with 10 ml of W5+ media (1.82 mM MES, 192 mM NaCl, 154 mM CaCl$_2$, 4.7 mM KCl, pH 6.0). The filtering step was repeated using a 70 μM screen. The final volume was brought to 40 ml by adding 10 ml of W5+ media. The cells were mixed by inverting the tube. The protoplasts were slowly layered onto 8 ml of a sucrose cushion solution (500 mM sucrose, 1 mM CaCl$_2$, 5 mM MES-KOH, pH 6.0) by adding the cushion solution to the bottom of a 50 ml conical centrifuge tube containing the cells. The tubes were centrifuged at 350×g for 15 minutes in a swinging bucket rotor. A 5 ml pipette tip was used to slowly remove the protoplast band (about 7-8 ml). The protoplasts were then transferred to a 50 ml conical tube and 25 ml of W5+wash was added. The tubes were inverted slowly and the centrifuged for 10 minutes at 200 g. The supernatant was removed, 10 ml of MMG solution was added and the tube was inverted slowly to resuspend the protoplasts. The protoplast density was determined using a haemocytometer or a flow cytometer. Typically, 4 PCV of cells suspension yields about 2 million protoplasts.

Transformation of Protoplasts Using PEG

The protoplast concentration was adjusted to 1.6 million/ml with MMG. Protoplast aliquots of 300 μl (about 500,000 protoplasts) were transferred into 2 ml sterile tubes. The protoplast suspension was mixed regularly during the transfer of protoplasts into the tubes. Plasmid DNA was added to the protoplast aliquots according to the experimental design. The rack containing the tubes of protoplasts was slowly inverted 3 times for 1 minute each to mix the DNA and protoplasts. The protoplasts were incubated for 5 minutes at room temperature. Three hundred microliters of a polyethylene glycol (PEG 4000) solution (40% ethylene glycol (81240-Sigma Aldrich), 0.3 M mannitol, 0.4 M CaCl$_2$) was added to the protoplasts and the rack of tubes was mixed for 1 min and incubated for 5 min, with gentle inversion twice during the incubation. One milliliter of W5+ was slowly added to the tubes and the rack of tubes inverted 15-20 times. The tubes were then centrifuged at 350 g for 5 min and the supernatant removed without disturbing the pellet. One milliliter of WI media (4 mM MES 0.6 M mannitol, 20 mM KCl, pH 6.0) was added to each tube and the rack was gently inverted to resuspend the pellets. The rack was covered with aluminum foil and laid on its side to incubate overnight at 23° C.

Measuring Transformation Frequency and Harvesting the Protoplasts

Quantification of protoplasts and transformation efficiencies were measured using a Quanta Flow Cytometer™ (Beckman-Coulter Inc). Approximately 16-18 hours post transformation, 100 μl from each replicate was sampled, placed in a 96 well plate and diluted 1:1 with WI solution. The replicates were resuspended 3 times and 100 μl was quantified using flow cytometry. Prior to submitting the samples for analysis, the samples were centrifuged at 200 g for 5 mM, supernatants were removed and the samples were flash frozen in liquid nitrogen. The samples were then placed in a −80° C. freezer until processing for molecular analysis.

Transformation of ZFN and Donor

Figure 14:
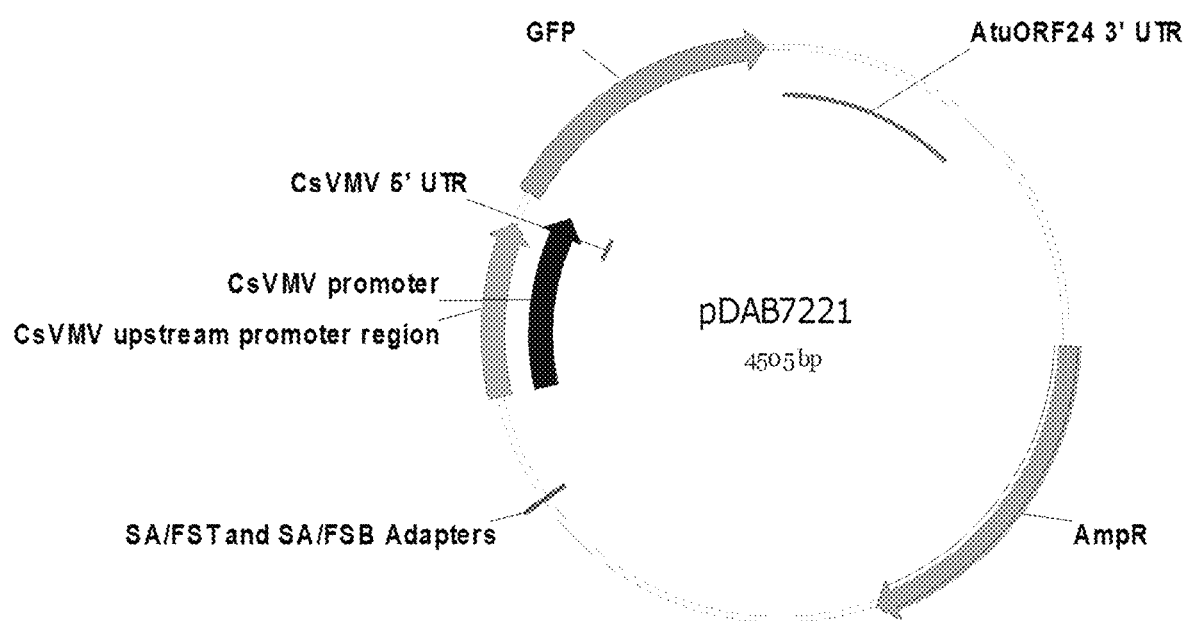
FIG. 14. Plasmid map of pDAB7221 (SEQ ID NO:7569). This plasmid contains the Cassava Vein Mosaic Virus Promoter (CsVMV) driving the GFP protein and flanked by the *Agrobacterium tumefaciens* (AtuORF 24 3'UTR).
Figure 15A:
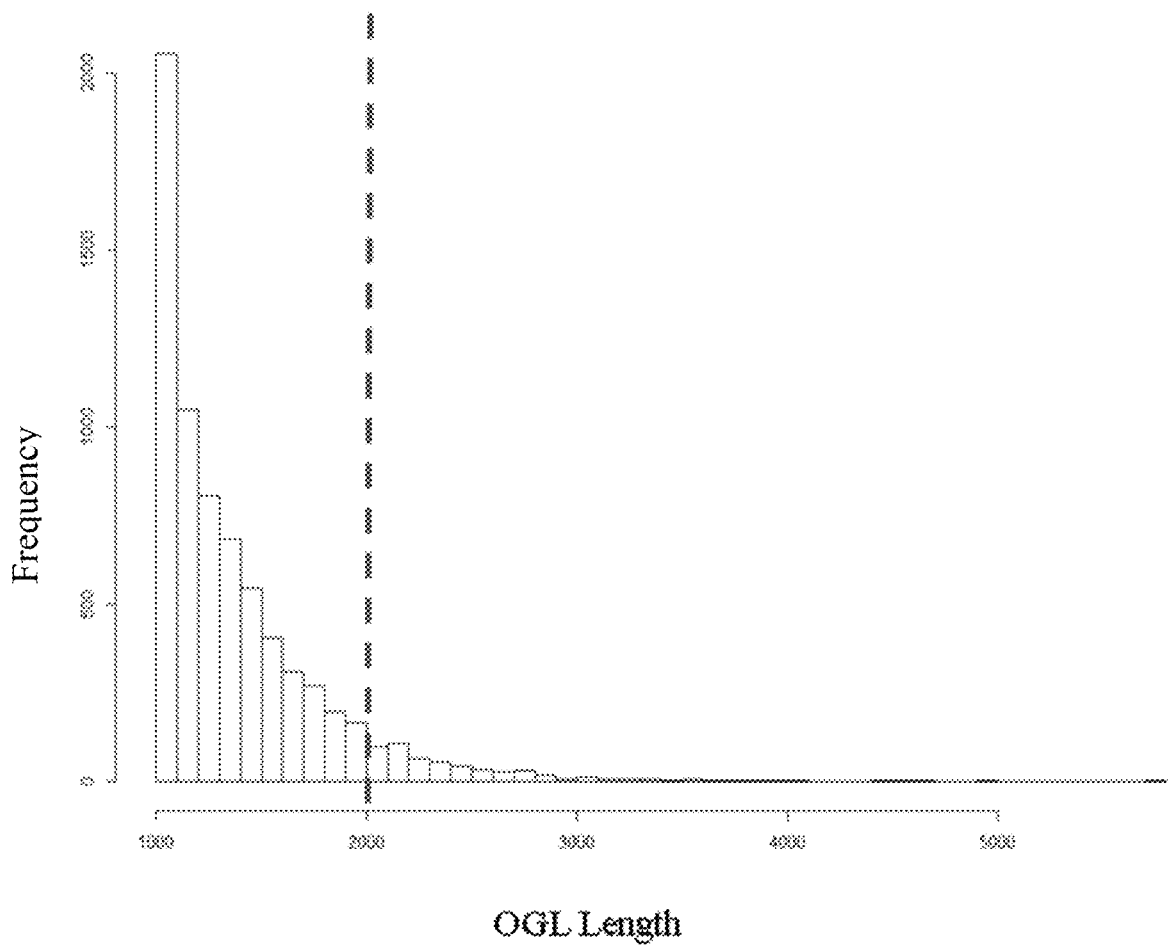
FIGS. 15A-15C. Histrogram of characteristics (length, expression of coding region within 40 Kb of loci, and recombination frequency) for the identified optimal nongenic soybean loci.
Figure 15B:
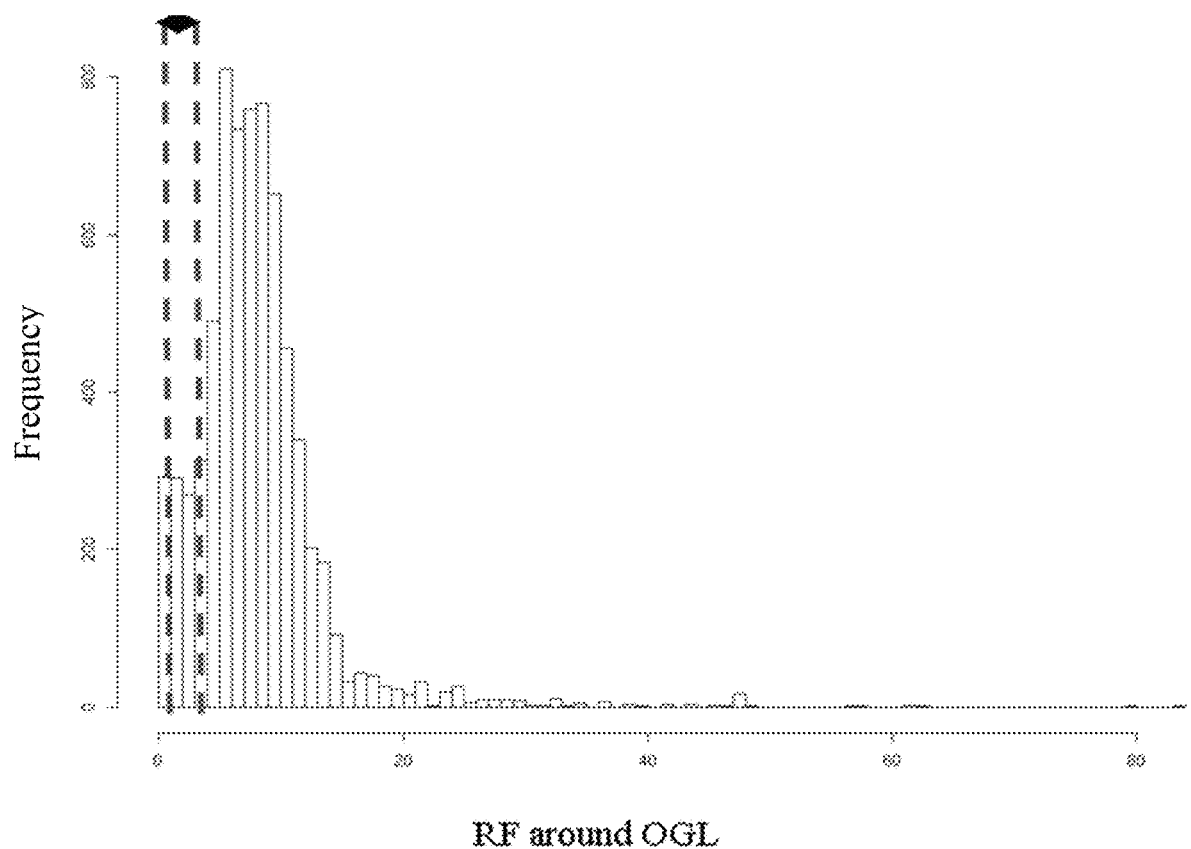
Figure 15C:
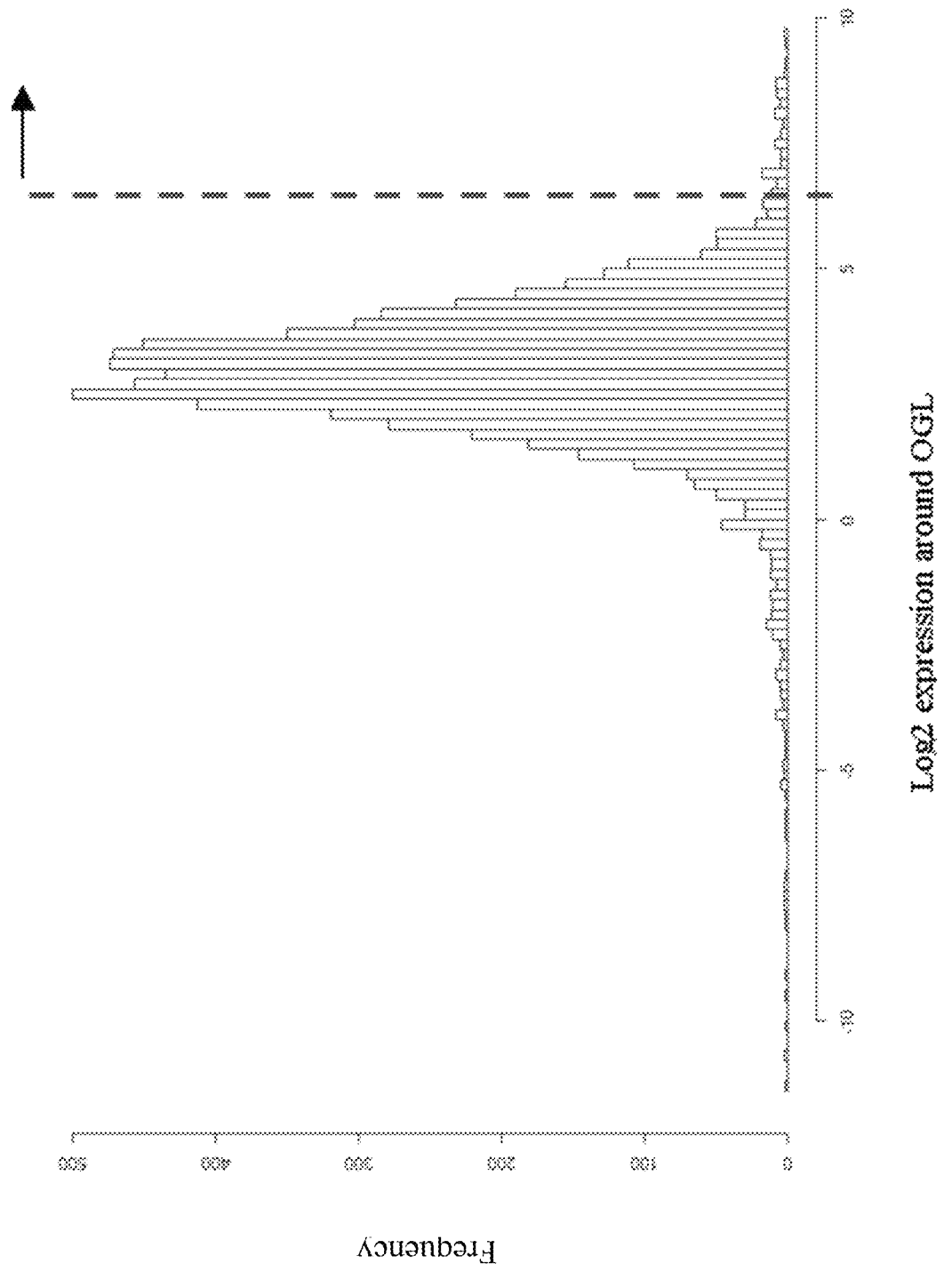

For each of the selected genomic loci of Table 5, the soybean protoplasts were transfected with constructs comprising a green fluorescent protein (gfp) gene expressing control, ZFN alone, donor alone and a mixture of ZFN and donor DNA at a ratio of 1:10 (by weight). The total amount of DNA for transfection of 0.5 million protoplasts was 80 μg. All treatments were conducted in replicates of three. The gfp gene expressing control used was pDAB7221 (FIG. 14, SEQ ID NO:7569) containing the Cassava Vein Mosaic Virs promoter—green fluorescent protein coding sequence—*Agrobacterium tumefaciens* ORF24 3'UTR gene expression cassettes. To provide a consistent amount of total DNA per transfection, either salmon sperm or a plasmid containing a gfp gene was used as filler where necessary. In a typical targeting experiment, 4 μg of ZFN alone or with 36 μg of donor plasmids were transfected and an appropriate amount of salmon sperm or pUC19 plasmid DNA was added to bring the overall amount of DNA to the final amount of 80 μg. Inclusion of gfp gene expressing plasmid as filler allows assessment of transfection quality across multiple loci and replicate treatments.

Example 5: Cleavage of Genomic Loci in Soybean Via Zinc Finger Nuclease

Targeting at select genomic loci was demonstrated by ZFN induced DNA cleavage and donor insertion using the protoplast based Rapid Targeting System (RTA). For each soybean select locus, up to six ZFN designs were generated and transformed into protoplasts either alone or with a universal donor polynucleotide and ZFN mediated cleavage and insertion was measured using Next Generation Sequencing (NGS) or junctional (in-out) PCR respectively.

ZFN transfected soybean protoplasts were harvested 24 hours post-transfection, by centrifugation at 1600 rpm in 2 ml EPPENDORF™ tubes and the supernatant was completely removed. Genomic DNA was extracted from protoplast pellets using the QIAGEN PLANT DNA EXTRACTION KIT™ (Qiagen, Valencia, Calif.). The isolated DNA was resuspended in 50 μL of water and concentration was determined by NANODROP® (Invitrogen, Grand Island, N.Y.). The integrity of the DNA was estimated by running samples on 0.8% agarose gel electrophoresis. All samples were normalized (20-25 ng/μL) for PCR amplification to generate amplicons for sequencing (Illumina, Inc., SanDiego, Calif.). Bar-coded PCR primers for amplifying regions encompassing each test ZFN recognition sequence from treated and control samples were designed and purchased from IDT (Coralville, Iowa, HPLC purified). Optimum amplification conditions were identified by gradient PCR using 0.2 μM appropriate bar-coded primers, ACCUPRIME PFX SUPERMIX™ (Invitrogen, Carlsbad, Calif.) and 100 ng of template genomic DNA in a 23.5 μL reaction. Cycling parameters were initial denaturation at 95° C. (5 min) followed by 35 cycles of denaturation (95° C., 15 sec), annealing (55-72° C., 30 sec), extension (68° C., 1 min) and a final extension (68° C., 7 min). Amplification products were analyzed on 3.5% TAE agarose gels and appropriate annealing temperature for each primer combination was determined and used to amplify amplicons from control and ZFN treated samples as described above. All amplicons were purified on 3.5% agarose gels, eluted in water and concentrations were determined by NANODROP™. For Next Generation Sequencing, 100 ng of PCR amplicon from the ZFN treated and corresponding untreated soybean protoplast controls were pooled together and sequenced using Ilumina Next Generation Sequencing (NGS).

The cleavage activity of appropriate ZFNs at each soybean optimal genomic loci were assayed. Short amplicons encompassing the ZFN cleavage sites were amplified from the genomic DNA and subjected to Illumina NGS from ZFN treated and control protoplasts. The ZFN induced cleavage or DNA double strand break was resolved by the cellular NHEJ repair pathway by insertion or deletion of nucleotides (indels) at the cleavage site and presence of indels at the cleavage site was thus a measure of ZFN activity and was determined by NGS. Cleavage activity of the target specific ZFNs was estimated as the number of sequences with indels per 1 million high quality sequences using NGS analysis software (Patent publication 2012-0173,153, data Analysis of DNA sequences). Activities were observed for sobyean selected genomic loci targets and were further confirmed by sequence alignments that show a diverse footprint of indels at each ZFN cleavage site. This data suggests that the soybean selected genomic loci were amenable to cleavage by ZFNs. Differential activity at each target was reflective of its chromatin state and amenability to cleavage as well as the efficiency of expression of each ZFN.

Figure 6:
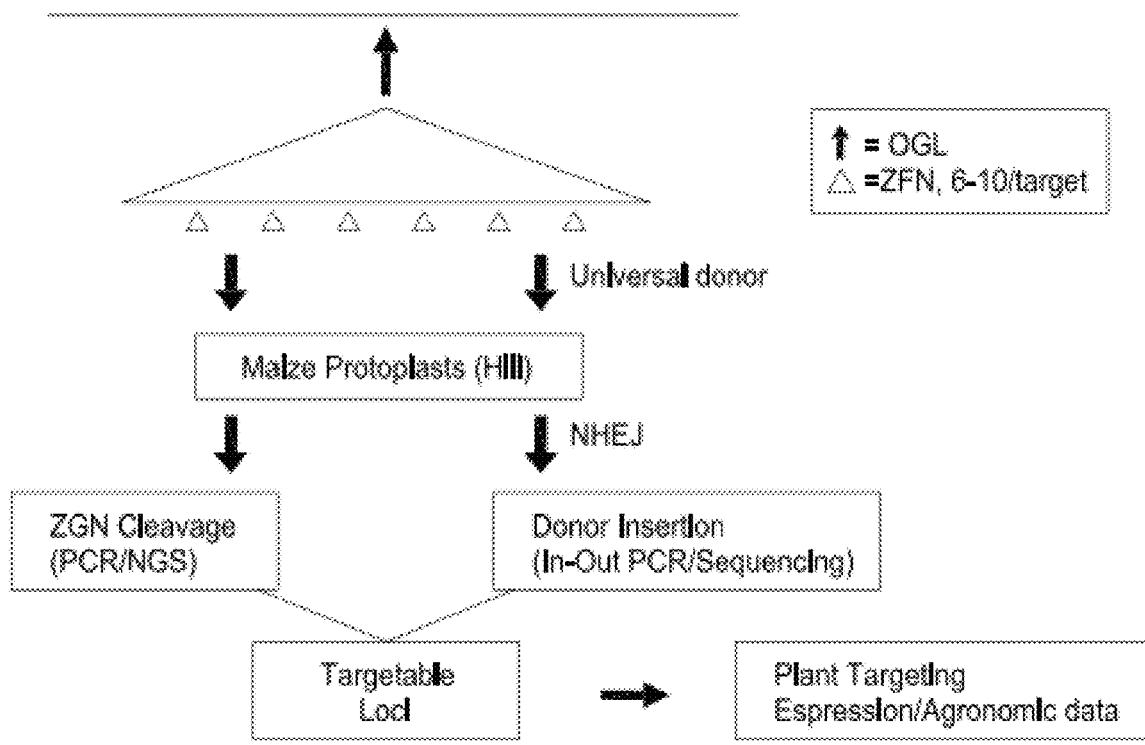
FIG. 6. Validation of soybean selected genomic loci targets using NHEJ based Rapid Targeting Analysis (RTA) method.

Example 6: Rapid Targeting Analysis of the Integration of a Polynucleotide Donor Validation of the targeting of the universal donor polynucleotide sequence within the soybean selected genomic loci targets via non-homologous end joining (NHEJ) meditated donor insertion, was performed using a semi-throughput protoplast based Rapid Testing Analysis method. For each soybean selected genomic loci target, around 3-6 ZFN designs were tested and targeting was assessed by measuring ZFN mediated cleavage by Next Generation Sequencing methods and donor insertion by junctional in-out PCR (FIG. 6). Soybean selected genomic loci that were positive in both assays were identified as a targetable locus.

ZFN Donor Insertion Rapid Testing Analysis

To determine if a soybean selected genomic loci target can be targeted for donor insertion, a ZFN construct and universal donor polynucleotide construct were co-delivered to soybean protoplasts which were incubated for 24 hours before the genomic DNA was extracted for analysis. If the expressed ZFN was able to cut the target binding site both at the soybean selected genomic loci target and in the donor, the linearized donor would then be inserted into the cleaved target site in the soybean genome via the non-homologous end joining (NHEJ) pathway. Confirmation of targeted integration at the soybean selected genomic loci target was completed based on an "In-Out" PCR strategy, where an "In" primer recognizes sequence at the native optimal genomic loci and an "Out" primer binds to sequence within the donor DNA. The primers were designed in a way that only when the donor DNA was inserted at the soybean selected genomic loci target, would the PCR assay produce an amplification product with the expected size. The In-Out PCR assay was performed at both the 5'- and 3'-ends of the insertion junction. The primers used for the analysis of integrated polynucleotide donor sequences are provided in Table 9.

ZFN Donor Insertion at Target Loci Using Nested "In-Out" PCR

All PCR amplifications were conducted using a TAKARA EX TAQ HS™ kit (Clonetech, Mountain View, Calif.). The first In-Out PCR was carried out in 25 μL final reaction volume that contains 1× TAKARA EX TAQ HS™ buffer, 0.2 mM dNTPs, 0.2 μM "Out" primer, 0.05 μM "In" primer (designed from the universal donor cassette described above), 0.75 unit of TAKARA EX TAQ HS™ polymerase, and 6 ng extracted soybean protoplast DNA. The reaction was then completed using a PCR program that consists of 94° C. for 3 min, 14 cycles of 98° C. for 12 sec, 60 30 sec and 72° C. for 1 min, followed by 72° C. for 10 min and held at 4° C. Final PCR products were run on an agarose gel along with 1 KB PLUS DNA LADDER™ (Life Technologies, Grand Island, N.Y.) for visualization.

The nested In-Out PCR was conducted in 25 μL final reaction volume that contained 1× TAKARA EX TAQ HS™ buffer, 0.2 mM dNTPs, 0.2 μM "Out" primer (Table 9), 0.1 μM "In" primer (designed from the universal donor cassette described above, Table 10), 0.75 units of TAKARA EX TAQ HS™ polymerase, and 1 μL of the first PCR product. The reaction was then completed using a PCR program that consisted of 94° C. for 3 min, 30 cycles of 98° C. for 12 sec, 60° C. for 30 sec and 72° C. for 45 sec, followed by 72° C. for 10 min and held at 4° C. Final PCR products were run on an agarose gel along with 1 KB PLUS DNA LADDER™ (Life Technologies, Grand Island, N.Y.) for visualization.

TABLE 9

List of all "Out" primers for nested In-Out PCR analysis of optimal genomic loci.

| Locus | PCR | End | Label | Primer | SEQ ID | Sequence |
|---|---|---|---|---|---|---|
| OGL01 | First PCR | 5'-end | | MAS1057 | SEQ ID NO: 7427 | CAAACAAGGAGAGAGCGAG |
| | | | GM Spec | | SEQ ID NO: 7428 | GATCGACATTGATCTGGCTA |
| | | 3'-end | | MAS1059 | SEQ ID NO: 7429 | GGCAAGGACACAAACGG |
| | | | GM Uzi | | SEQ ID NO: 7430 | ATATGTGTCCTACCGTATCAGG |
| | Nest PCR | 5'-end | | MAS1058 | SEQ ID NO: 7431 | TACCCAAGAAGAAACATTAGACC |
| | | | GM Spec Nst | | SEQ ID NO: 7432 | GTTGCCTTGGTAGGTCC |
| | | 3'-end | | MAS1060 | SEQ ID NO: 7433 | ATGTAGTTGTTTCTCTGCTGTG |
| | | | GM Uzi Nst | | SEQ ID NO: 7434 | GAGCCATCAGTCCAACAC |
| OGL02 | First PCR | 5'-end | | MAS1061 | SEQ ID NO: 7435 | CACGAGGTTTACGCCAT |
| | | 3'-end | | MAS1063 | SEQ ID NO: 7436 | TCTGATAACTTGCTAGTGTGTG |
| | Nest PCR | 5'-end | | MAS1062 | SEQ ID NO: 7437 | GCTGCTCAGTGGATGTC |
| | | 3'-end | | MAS1064 | SEQ ID NO: 7438 | TCGTTTATCGGGATTGTCTC |
| OGL03 | First PCR | 5'-end | | MAS1133 | SEQ ID NO: 7439 | TTGTTGCTTCTATGCTCCTC |
| | | 3'-end | | MAS1135 | SEQ ID NO: 7440 | CGTCGTTGTGGATGAGG |

TABLE 9-continued

List of all "Out" primers for nested In-Out PCR analysis of optimal genomic loci.

| | | | | |
|---|---|---|---|---|
| | Nest PCR | 5'-end | MAS1134 CCATTGCTGTTCTGCTTG | SEQ ID NO: 7441 |
| | | 3'-end | MAS1136 TGTAGGTGACGGGTGTG | SEQ ID NO: 7442 |
| OGL04 | First PCR | 5'-end | MAS1155 GTGTGTTATTGTCTGTGTTCTC | SEQ ID NO: 7443 |
| | | 3'-end | MAS1139 GACTCCTATGTGCCTGATTC | SEQ ID NO: 7444 |
| | Nest PCR | 5'-end | MAS1156 GAGAACGATGGATAGAAAAGCA | SEQ ID NO: 7445 |
| | | 3'-end | MAS1140 TTTGTTTCAGTCTTGCTCCT | SEQ ID NO: 7446 |
| OGL05 | First PCR | 5'-end | MAS1121 CTACCTATAAACTGGACGGAC | SEQ ID NO: 7447 |
| | | 3'-end | MAS1123 CGTCAAATGCCCATTATTCAT | SEQ ID NO: 7448 |
| | Nest PCR | 5'-end | MAS1122 GATTTGGGCTTGGGCATA | SEQ ID NO: 7449 |
| | | 3'-end | MAS1124 TGAATCCCACTAGCACCAT | SEQ ID NO: 7450 |
| OGL06 | First PCR | 5'-end | MAS1065 GGAGATAGAGTTAGAAGGTTTTGA | SEQ ID NO: 7451 |
| | | 3'-end | MAS1067 GAGGTTGTTTTGACGCCA | SEQ ID NO: 7452 |
| | Nest PCR | 5'-end | MAS1066 AAGGAAGAAATGTGAAAAGAAGAC | SEQ ID NO: 7453 |
| | | 3'-end | MAS1068 AGAGAAGCGAAACCCAAAG | SEQ ID NO: 7454 |
| OGL07 | First PCR | 5'-end | MAS1069 GACCCATTTATCTATCCCGTAT | SEQ ID NO: 7455 |
| | | 3'-end | MAS1071 GGCTCGTATCAGTTCCATTTAG | SEQ ID NO: 7456 |
| | Nest PCR | 5'-end | MAS1070 AAGTACGAACAAGATTGGTGAG | SEQ ID NO: 7457 |
| | | 3'-end | MAS1072 TCTATTACATTCCATCCAAAGGC | SEQ ID NO: 7458 |
| OGL08 | First PCR | 5'-end | MAS1141 GAAACGAGAGAGATGACCAATA | SEQ ID NO: 7459 |
| | | 3'-end | MAS1143 GGTTCACGGGTTCAGC | SEQ ID NO: 7460 |
| | Nest PCR | 5'-end | MAS1142 CCTGACGCAAAAGAAGAAATG | SEQ ID NO: 7461 |
| | | 3'-end | MAS1144 GTTATACTTACTGTCACCACGAG | SEQ ID NO: 7462 |
| OGL09 | First PCR | 5'-end | MAS1073 TTATTCCTGCGTCTCTCAC | SEQ ID NO: 7463 |
| | | 3'-end | MAS1075 TTGTGCGTGATAAATAGGGC | SEQ ID NO: 7464 |
| | Nest PCR | 5'-end | MAS1074 GATAGTTGATTGTGTTGTTAGCATA | SEQ ID NO: 7465 |
| | | 3'-end | MAS1076 CTCACCTGTTGCCCGTA | SEQ ID NO: 7466 |
| OGL10 | First PCR | 5'-end | MAS1077 GTTTGAGTTGGCAGGTGT | SEQ ID NO: 7467 |
| | | 3'-end | MAS1079 CCGTGACTTGTGCTAGAG | SEQ ID NO: 7468 |
| | Nest PCR | 5'-end | MAS1078 CTGAAGTTGACGCCGC | SEQ ID NO: 7469 |
| | | 3'-end | MAS1080 AAGCACAGGACGGTTAGA | SEQ ID NO: 7470 |
| OGL11 | First PCR | 5'-end | MAS1125 CACGGGTCACAAATCTAGTT | SEQ ID NO: 7471 |
| | | 3'-end | MAS1127 CCATTAAGTCTGTCTCAACTTTC | SEQ ID NO: 7472 |
| | Nest PCR | 5'-end | MAS1126 CTGCTTGAGTAGGAAGAAGTG | SEQ ID NO: 7473 |
| | | 3'-end | MAS1128 ATCACCAAAGCCGAGAAC | SEQ ID NO: 7474 |
| OGL12 | First PCR | 5'-end | MAS1129 GTAGGCGTGAAGGCTG | SEQ ID NO: 7475 |
| | | 3'-end | MAS1131 TGAAACCGCACAATCTCG | SEQ ID NO: 7476 |
| | Nest PCR | 5'-end | MAS1130 CCCTCCGAAACAATCCG | SEQ ID NO: 7477 |
| | | 3'-end | MAS1132 ACCCGTTGAATGCGAG | SEQ ID NO: 7478 |
| OGL13 | First PCR | 5'-end | MAS1081 AAGGTGGATGGGAGGAA | SEQ ID NO: 7479 |
| | | 3'-end | MAS1083 TGGCACTAATACATTACATAAGACT | SEQ ID NO: 7480 |
| | Nest PCR | 5'-end | MAS1082 ATGTTACTTCAATCCCTCGTC | SEQ ID NO: 7481 |
| | | 3'-end | MAS1084 TGAATAGGGCAAAAACACAC | SEQ ID NO: 7482 |
| OGL14 | First PCR | 5'-end | MAS1085 CAAGTGAGCAGGGCG | SEQ ID NO: 7483 |
| | | 3'-end | MAS1087 CTATCATTCGTAAAGTTTGAGGAC | SEQ ID NO: 7484 |
| | Nest PCR | 5'-end | MAS1086 AGCCTCACTCACAACAAAG | SEQ ID NO: 7485 |
| | | 3'-end | MAS1088 TGAAACTGTCTTGTGACTTACC | SEQ ID NO: 7486 |
| OGL15 | First PCR | 5'-end | MAS1089 GCACTGACATACCAACAATC | SEQ ID NO: 7487 |
| | | 3'-end | MAS1091 GTTGTCGGGATTTCACTTCAT | SEQ ID NO: 7488 |
| | Nest PCR | 5'-end | MAS1090 GATAGGAGAAAGAGCAAGGAC | SEQ ID NO: 7489 |
| | | 3'-end | MAS1092 TTCTCAACATCAACTCATACACTC | SEQ ID NO: 7490 |
| OGL16 | First PCR | 5'-end | MAS1093 CTCAAAGCAACATCAACCAT | SEQ ID NO: 7491 |

TABLE 9-continued

List of all "Out" primers for nested In-Out PCR analysis of optimal genomic loci.

| | | | | |
|---|---|---|---|---|
| | | 3'-MAS1095 end | SEQ ID NO: 7492 | AATCCCAAAGCAGCCAAC |
| | Nest PCR | 5'-MAS1094 end | SEQ ID NO: 7493 | AAACACAAATCACATCATAGTAAAC |
| | | 3'-MAS1096 end | SEQ ID NO: 7494 | GCTAGTATGCTTCTGTCAGTTTA |
| OGL17 | First PCR | 5'-MAS916 end | SEQ ID NO: 7495 | ACTAGTTCTTTCCCGAACATT |
| | | 3'-MAS918 end | SEQ ID NO: 7496 | CATTTGGTGATTTAACTCATCAGC |
| | Nest PCR | 5'-MAS917 end | SEQ ID NO: 7497 | AAATTTACCACGGTTGGTCC |
| | | 3'-MAS919 end | SEQ ID NO: 7498 | TCTGCATTAACTATATCAGGAGG |
| OGL18 | First PCR | 5'-MAS920 end | SEQ ID NO: 7499 | ATTCAACATTTACCCTTCACAA |
| | | 3'-MAS922 end | SEQ ID NO: 7500 | AATTCTTTCTCATACTTGGTTGT |
| | Nest PCR | 5'-MAS921 end | SEQ ID NO: 7501 | CCTTGTTTTCCGTACTATCAATT |
| | | 3'-MAS923 end | SEQ ID NO: 7502 | TATTGGAGTAATGTGGACAAGC |
| OGL19 | First PCR | 5'-MAS924 end | SEQ ID NO: 7503 | AACAACTTTCCAACCCACAA |
| | | 3'-MAS1009 end | SEQ ID NO: 7504 | CGTTTTACCTTGACTTGACCT |
| | Nest PCR | 5'-MAS925 end | SEQ ID NO: 7505 | CCAGAGAGGAACCAGAAGT |
| | | 3'-MAS1010 end | SEQ ID NO: 7506 | CCTTAGACAAAACTCGCACTT |
| OGL20 | First PCR | 5'-MAS1011 end | SEQ ID NO: 7507 | GAAAGAGAAGACGCCACC |
| | | 3'-MAS930 end | SEQ ID NO: 7508 | TCATTAGAGGGTCAAAAGTGC |
| | Nest PCR | 5'-MAS1012 end | SEQ ID NO: 7509 | CCTGAAGAAAAGTGGGAGAA |
| | | 3'-MAS931 end | SEQ ID NO: 7510 | TTCAATCATAATTAAACTAATAAGACTGT |
| OGL22 | First PCR | 5'-MAS960 end | SEQ ID NO: 7511 | ACTGAATGTATTGTCCGACG |
| | | 3'-MAS962 end | SEQ ID NO: 7512 | GCCCTACATTTTCATTTCATTGG |
| | Nest PCR | 5'-MAS961 end | SEQ ID NO: 7513 | GTGAGACCGCCCCTT |
| | | 3'-MAS963 end | SEQ ID NO: 7514 | CCACTACTTTTTACTCACAGAAGA |
| OGL24 | First PCR | 5'-MAS968 end | SEQ ID NO: 7515 | GTCAATTCTCATCAGTTCCATCT |
| | | 3'-MAS970 end | SEQ ID NO: 7516 | CGATGAATAGTATGAGTGCTAG |
| | Nest PCR | 5'-MAS969 end | SEQ ID NO: 7517 | TGCGTCTCTTGCTTCCTA |
| | | 3'-MAS971 end | SEQ ID NO: 7518 | GCCACGAGAGGATAGAATAAT |
| OGL25 | First PCR | 5'-MAS972 end | SEQ ID NO: 7519 | TAGTGTACCCTCCTCATCATA |
| | | 3'-MAS974 end | SEQ ID NO: 7520 | GATAATCAAATGAGTGGACGAATA |
| | Nest PCR | 5'-MAS973 end | SEQ ID NO: 7521 | TGTATTTGGATAAGTGTGGGAC |
| | | 3'-MAS975 end | SEQ ID NO: 7522 | GATTTTAGCGTGATTGATGGAAG |
| OGL28 | First PCR | 5'-MAS1149 end | SEQ ID NO: 7523 | CTGAAGCAAGTGGTGATGTT |
| | | 3'-MAS1151 end | SEQ ID NO: 7524 | CTTACCACCACCTGCG |
| | Nest PCR | 5'-MAS1150 end | SEQ ID NO: 7525 | GCATAAAGGTCAGCAGAGG |
| | | 3'-MAS1152 end | SEQ ID NO: 7526 | TACTCTTTAGCCATAGCCAAT |
| OGL30 | First PCR | 5'-MAS988 end | SEQ ID NO: 7527 | GTTTATTGCCAGAGACGGT |
| | | 3'-MAS990 end | SEQ ID NO: 7528 | CGTCGTTGCTTGCTTGT |
| | Nest PCR | 5'-MAS989 end | SEQ ID NO: 7529 | GGAAAGACATAAAAGTAAATGGAAG |
| | | 3'-MAS991 end | SEQ ID NO: 7530 | TAACTACCTGATAACCTCCTTTT |
| OGL31 | First PCR | 5'-MAS992 end | SEQ ID NO: 7531 | GCAAACTTTAAGTAAACTAGAGGC |
| | | 3'-MAS994 end | SEQ ID NO: 7532 | AGTGTACTCTAGTCAGATTTTGC |
| | Nest PCR | 5'-MAS993 end | SEQ ID NO: 7533 | CAACCCAACAAGCAAACAC |
| | | 3'-MAS995 end | SEQ ID NO: 7534 | CTCGGTTTTGTAGTCATCTATGTA |
| OGL33 | First PCR | 5'-MAS1101 end | SEQ ID NO: 7535 | GATGAATAACAGTGCGAGGA |
| | | 3'-MAS942 end | SEQ ID NO: 7536 | CTGTAATCCTCATTTTGCACG |
| | Nest PCR | 5'-MAS941 end | SEQ ID NO: 7537 | GGGGTAGTTACACTTCTGC |
| | | 3'-MAS943 end | SEQ ID NO: 7538 | GGTGTGGTCGGCATATAGA |
| OGL34 | First PCR | 5'-MAS944 end | SEQ ID NO: 7539 | TTCGCACAAGCCATCC |
| | | 3'-MAS946 end | SEQ ID NO: 7540 | AACGACTTTTTGAATAGATGCT |
| | Nest PCR | 5'-MAS945 end | SEQ ID NO: 7541 | GCATTCCTTCTTGTCTCGT |

TABLE 9-continued

List of all "Out" primers for nested In-Out PCR analysis of optimal genomic loci.

| | | | | |
|---|---|---|---|---|
| | | 3'-end | MAS947 | SEQ ID NO: 7542 AACTTAGAGAAACTCATAACTCATC |
| OGL35 | First PCR | 5'-end | MAS948 | SEQ ID NO: 7543 TCATAGCTTCAAGGGATTCAC |
| | | 3'-end | MAS950 | SEQ ID NO: 7544 GTTCATCAAAACACGCAAGA |
| | Nest PCR | 5'-end | MAS949 | SEQ ID NO: 7545 CTCATGCCAACAAAAGCC |
| | | 3'-end | MAS951 | SEQ ID NO: 7546 GTAGTAACAAAAATGGATAACGCAG |
| OGL36 | First PCR | 5'-end | MAS936 | SEQ ID NO: 7547 TATCTGGCTTGAAGCTGAAT |
| | | 3'-end | MAD938 | SEQ ID NO: 7548 TTATTTCCTTCGTGGCTTCG |
| | Nest PCR | 5'-end | MAS937 | SEQ ID NO: 7549 CTCCACAATTTAGCATCCAAG |
| | | 3'-end | MAS939 | SEQ ID NO: 7550 CGTCCATGTTTACTTGGCTA |
| OGL37 | First PCR | 5'-end | MAS952 | SEQ ID NO: 7570 GTCATCATAATTGCTGTCCCA |
| | | 3'-end | MAS954 | SEQ ID NO: 7571 GGATGTGTGCCTGAGC |
| | Nest PCR | 5'-end | MAS953 | SEQ ID NO: 7572 CCTTCCTCGTGCCCTTA |
| | | 3'-end | MAS955 | SEQ ID NO: 7573 CCCCTAATCTCATCGCAAG |
| OGL38 | First PCR | 5'-end | MAS932 | SEQ ID NO: 7551 TCTGTTGATTCCTAATCGTAGC |
| | | 3'-end | MAS934 | SEQ ID NO: 7552 GTGATTGACATTTGTCTATAAGCA |
| | Nest PCR | 5'-end | MAS933 | SEQ ID NO: 7553 CCTCTTCACTGTGACTGAAC |
| | | 3'-end | MAS935 | SEQ ID NO: 7554 TTTCGGCTTGACATTTCTTTC |
| OGL39 | First PCR | 5'-end | MAS956 | SEQ ID NO: 7555 TGGCAAATCACACGGTC |
| | | 3'-end | MAS958 | SEQ ID NO: 7556 ACTACCTTGCCCCTAAGATC |
| | Nest PCR | 5'-end | MAS957 | SEQ ID NO: 7557 TGCCACGACAAGAATTTCAT |
| | | 3'-end | MAS959 | SEQ ID NO: 7558 TGGTGTGATTCCAACGC |

TABLE 10

List of all "In" primers for nested In-Out PCR analysis of optimal genomic loci.

| | | | |
|---|---|---|---|
| First PCR | 3'-end | GM_UnDo_3'F | SEQ ID NO: 7559 CAAATTCCCACTAAGCGCT |
| Nest PCR | 3'-end | GM_UnDo_3'_NST | SEQ ID NO: 7560 TAAAGGTGAGCAGAGGCA |

Deployment of the In-Out PCR assay in a protoplast targeting system was particularly challenging as large amounts of the plasmid DNA was used for transfection, and the large amount of DNA remains in the protoplast targeting system and was subsequently extracted along with cellular genomic DNA. The residual plasmid DNA may dilute the relative concentration of the genomic DNA and reduce the overall sensitivity of detection and can also be a significant cause of non-specific, aberrant PCR reactions. ZFN induced NHEJ-based donor insertion typically occurs in either a forward or a reverse orientation. In-Out PCR analysis of DNA for the forward orientation insertion often exhibited false positive bands, possibly due to shared regions of homology around the ZFN binding site in the target and donor that could result in priming and extension of unintegrated donor DNA during the amplification process. False positives were not seen in analyses that probed for reverse orientation insertion products and therefore all targeted donor integration analysis was carried out to interrogate reverse donor insertion in the RTA. In order to further increase specificity and reduce background, a nested PCR strategy was also employed. The nested PCR strategy used a second PCR amplification reaction that amplified a shorter region within the first amplification product of the first PCR reaction. Use of asymmetric amounts of "in" and "out" primers optimized the junctional PCR further for rapid targeting analysis at selected genomic loci.

The In-Out PCR analysis results were visualized on an agarose gel. For all soybean selected genomic loci of Table 12, "ZFN+donor treatments" produced a near expected sized band at the 5' and 3' ends. Control ZFN or donor alone treatments were negative in the PCR suggesting that the method was specifically scoring for donor integration at the target site of at least 32 of the optimal nongenic soybean genomic loci. All treatments were conducted in replicates of 3-6 and presence of the anticipated PCR product in multiple replicates (>1 at both ends) was used to confirm targeting. Donor insertion through NHEJ often produces lower intensity side products that were generated due to processing of linearized ends at the target and/or donor ZFN sites. In addition, it was observed that different ZFNs resulted in different levels of efficiency for targeted integration, with some of the ZFNs producing consistently high levels of donor integration, some ZFNs producing less consistent levels of donor integration, and other ZFNs resulting in no integration. Overall, for each of the soybean selected genomic loci targets that were tested, targeted integration was demonstrated within the soybean representative genomic loci targets by one or more ZFNs, which confirms that each of these loci were targetable. Furthermore, each of the soybean selected genomic loci targets was suitable for precision gene transformation. The validation of these soybean selected genomic loci targets were repeated multiple times with similar results, thus confirming the reproducibility of the validation process which includes plasmid design and construct, protoplast transformation, sample processing, sample analysis.

Conclusion

The donor plasmid and one ZFN designed to specifically cleave soybean selected genomic loci targets were transfected into soybean protoplasts and cells were harvested 24 hours later. Analysis of the genomic DNA isolated from control, ZFN treated and ZFN with donor treated protoplasts by in-out junctional PCR showed targeted insertion of the universal donor polynucleotide as a result of genomic DNA cleavage by the ZFNs (Table 12). These studies show that the universal donor polynucleotide system can be used to assess targeting at endogenous sites and for screening candidate ZFNs. Finally, the protoplast based Rapid Targeting Analysis and the novel universal donor polynucleotide sequence systems provide a rapid avenue for screening genomic targets and ZFNs for precision genome engineering efforts in plants. The methods can be extended to assess site specific cleavage and donor insertion at genomic targets in any system of interest using any nuclease that introduces DNA double or single strand breaks.

Over 7,018 selected genomic loci were identified by various criteria detailed above. The selected genomic loci were clustered using Principal Component Analysis based on the ten parameters used for defining the selected genomic loci. A representative of the clusters in addition to some other loci of interest were demonstrated to be targetable.

TABLE 12

Illustrates the results of the integration of a universal donor polynucleotide sequence within the soybean selected genomic loci targets.

| Name | ID | Location | Cluster Assignment | ZFN (pDAB#) | Donor (pDAB#) | Targetable Locus (Y/N) |
|---|---|---|---|---|---|---|
| OGL01 | soy_ogl_308 | Gm02: 1204801 . . . 1209237 | 1 | 124201 | 124280 | Y |
| OGL02 | soy_ogl_307 | Gm02: 1164701 . . . 1168400 | 2 | 124221 | 124281 | Y |
| OGL03 | soy_ogl_2063 | Gm06: 43091928 . . . 43094600 | 3 | 125305 | 125332 | Y |
| OGL04 | soy_ogl_1906 | Gm06: 11576991 . . . 11578665 | 4 | 125309 | 125330 | Y |
| OGL05 | soy_ogl_262 | Gm01: 51061272 . . . 51062909 | 5 | 124884 | 124290 | Y |
| OGL06 | soy_ogl_5227 | Gm16: 1298889 . . . 1300700 | 6 | 124234 | 123838 | Y |
| OGL07 | soy_ogl_4074 | Gm12: 33610401 . . . 33611483 | 7 | 124257 | 123839 | Y |
| OGL08 | soy_ogl_3481 | Gm10: 40763663 . . . 40764800 | 8 | 125316 | 125332 | Y |
| OGL09 | soy_ogl_1016 | Gm03: 41506001 . . . 41507735 | 9 | 124265 | 123836 | Y |
| OGL10 | soy_ogl_937 | Gm03: 37707001 . . . 37708600 | 10 | 124273 | 123837 | Y |
| OGL11 | soy_ogl_5109 | Gm15: 42391349 . . . 42393400 | 11 | 124888 | 124290 | Y |
| OGL12 | soy_ogl_6801 | Gm20: 36923690 . . . 36924900 | 12 | 124885 | 124291 | Y |
| OGL13 | soy_ogl_6636 | Gm19: 49977101 . . . 49978357 | 13 | 124610 | 124294 | Y |
| OGL14 | soy_ogl_4665 | Gm14: 5050547 . . . 5051556 | 14 | 124614 | 124845 | Y |
| OGL15 | soy_ogl_6189 | Gm18: 55694401 . . . 55695900 | 15 | 124636 | 124293 | Y |
| OGL16 | soy_ogl_4222 | Gm13: 23474923 . . . 23476100 | 16 | 124648 | 124292 | Y |
| OGL17 | soy_ogl_2543 | Gm08: 7532001 . . . 7534800 | 17 | 121225 | 121277 | Y |
| OGL18 | soy_ogl_310 | Gm02: 1220301 . . . 1222300 | 18 | 121227 | 121278 | Y |
| OGL19 | soy_ogl_2353 | Gm07: 17194522 . . . 17196553 | 19 | 121233 | 121279 | Y |
| OGL20 | soy_ogl_1894 | Gm06: 10540801 . . . 10542300 | 20 | 121235 | 121280 | Y |
| OGL22 | soy_ogl_3218 | Gm09: 40167479 . . . 40168800 | 22 | 121238 | 121281 | Y |
| OGL24 | soy_ogl_3333 | Gm10: 2950701 . . . 2951800 | 24 | 121234 | 121280 | Y |
| OGL25 | soy_ogl_2546 | Gm08: 7765875 . . . 7767500 | 25 | 121249 | 121284 | Y |
| OGL28 | soy_ogl_5957 | Gm18: 6057701 . . .6059100 | 28 | 125324 | 125334 | Y |
| OGL30 | soy_ogl_3818 | Gm11: 10146701 . . . 10148200 | 30 | 121265 | 121288 | Y |
| OGL31 | soy_ogl_5551 | Gm17: 6541901 . . . 6543200 | 31 | 121271 | 121289 | Y |
| OGL33 | soy_OGL_684* | Gm02: 45903201 . . . 45907300 | 1 | 124666 | 123812 | Y |
| OGL34 | soy_OGL_682 | Gm02: 45816543 . . . 45818777 | 9 | 124814 | 121937 | Y |
| OGL35 | soy_OGL_685 | Gm02: 45910501 . . . 45913200 | 1 | 124690 | 123811 | y |
| OGL36 | soy_OGL_1423 | Gm04: 45820631 . . . 45822916 | 2 | 124815 | 121937 | Y |
| OGL37* | soy_OGL_1434 | Gm04: 46095801 . . . 46097968 | 1 | 125338 | 124871 | Y |
| OGL38 | soy_OGL_4625 | Gm14: 3816738 . . . 3820070 | 1 | 124816 | 121937 | Y |
| OGL39 | soy_OGL_6362 | Gm19: 5311001 . . . 5315000 | 1 | 124842 | 124864 | Y |

Example 7: Optimal Nongenic Soybean Genomic Loci for Transgene Integration

A suite of optimal nongenic soybean genomic loci were identified from the 7,018 optimal nongenic soybean genomic loci to select multiple loci for site specific targeting and integration of gene expression cassettes and to generate stacks of gene expression cassettes within a single chromosome. The resulting set of three optimal nongenic soybean genomic loci are referred to herein as a "Mega Locus". The following criteria were used to filter the pool of optimal nongenic soybean genomic loci and select a suite of optimal nongenic soybean genomic loci:
1) Location of at least 3 optimal nongenic soybean genomic loci on the same chromosome in proximity to each other (within 500 Kb of the center optimal nongenic soybean genomic loci);
2) Optimal nongenic soybean genomic loci greater than 2 Kb in length, and within 50 Kb of each other; and,
3) The central/middle optimal nongenic soybean genomic loci is greater than 4 Kb in length.

Each of the above described criteria were applied to select a suite of optimal nongenic soybean genomic loci. The identified optimal nongenic soybean genomic loci are shown in Table 13.

TABLE 13

Optimal nongenic soybean genomic loci identified and selected for targeting with a gene expression cassette.

| OGL_ID | Location | Length | SEQ ID NO: | Grouping of Three Loci |
|---|---|---|---|---|
| soy_OGL_308* | Gm02: 1204801..1209237 | 4437 | 43 | Targetable |
| soy_OGL_307* | Gm02: 1164701..1168400 | 3700 | 566 | Mega |
| soy_OGL_310 | Gm02: 1220301..1222300 | 2000 | 4236 | Locus #1 |
| soy_OGL_684* | Gm02: 45903201..45907300 | 4100 | 47 | Targetable |
| soy_OGL_682 | Gm02: 45816543..45818777 | 2235 | 2101 | Mega |
| soy_OGL_685 | Gm02: 45910501..45913200 | 2700 | 48 | Locus #2 |

*indicates that the OGL is long enough to be targeted by two separate gene expression cassettes.

Two additional optimal nongenic soybean genomic loci that were greater than 2 Kb and within 500 Kb to a known transgenic genomic event that was produced via random integration of a T-strand insert (e.g., AAD-12 Event 416: located at soybean chromosomal position, Gm04: 46002956..46005750 as described in International Patent App. No. WO2011066384A1) were also selected for targeted gene stacking. The selected optimal nongenic soybean genomic loci are shown in Table 14.

TABLE 14

Optimal nongenic soybean genomic loci identified and selected for targeting with a gene expression cassette.

| OGL_ID | Location | Length | SEQ ID NO: | Grouping of Three Loci |
|---|---|---|---|---|
| soy_OGL_1423 | Gm04: 45820631..45822916 | 2286 | 639 | Targetable |
| soy_OGL_1434 | Gm04: 46095801..46097968 | 2168 | 137 | Megalocus 3 |

A third suite of optimal nongenic soybean genomic loci were identified from the 7,018 optimal nongenic soybean genomic loci to select a suite of loci for site specific targeting and integration of gene expression cassettes and to generate stacks of gene expression cassettes. The following criteria were used to filter the pool of optimal nongenic soybean genomic loci and select a suite of optimal nongenic soybean genomic loci:
1) Identify optimal nongenic soybean genomic loci greater than 3 Kb in length;
2) Average expression of neighboring genes within a 40 Kb region in root and shoot tissues is greater than 7.46, which is the 47.7% percentile of all optimal nongenic soybean genomic loci;
3) A recombination frequency of 0.5-4, which is below the mean/median for all of the optimal nongenic soybean genomic loci;
4) A GC content greater than 25%.

Each of the above described criteria were applied to select a suite of optimal nongenic soybean genomic loci. The identified optimal nongenic soybean genomic loci are shown in Table 15. All selected optimal nongenic soybean loci were screened for proximity to known soybean QTLs. Loci that are greater than 3 Kb can be targeted sequentially at the endogenous sequence.

TABLE 15

Optimal nongenic soybean genomic loci identified and selected for targeting with a gene expression cassette.

| OGL_ID | Location | Length | SEQ ID NO: |
|---|---|---|---|
| soy_OGL_4625 | Gm14: 3816738..3820070 | 3333 | 76 |
| soy_OGL_6362 | Gm19: 5311001..5315000 | 4000 | 440 |
| soy_OGL_308 | Gm02: 1204801..1209237 | 4437 | 43 |

The optimal nongenic soybean genomic loci that are selected using the above described criteria are validated by integrating a gene expression construct that contains selectable/reportable markers. This gene expression cassette is stably integrated into soybean plants via genomic targeting using a site specific nuclease. The targeted optimal nongenic soybean genomic loci that are produced and contain an expressable transgene are analyzed to identify single copy events that contain a full length integrated gene expression cassette. The expression profiles of the optimal nongenic soybean genomic loci are analyzed via qRT-PCR, Western blot, ELISA, LC-MS MS, and other known RNA or protein detection methods over multiple plant generations (e.g., $T_1$ and $T_2$ generations). In addition, the effect of the transgene expression cassette integration within the optimal nongenic soybean genomic loci on neighboring gene expression is assayed. Finally, the effect of the transgene expression cassette integration within the optimal nongenic soybean genomic loci on agronomic properties of soybean plants is assayed.

Lengthy table referenced here

US11098316-20210824-T00001

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US11098316B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11098316B2). An electronic copy of the "Sequence Listing" will also be available from the USPTO upon request and payment of the fee set forth in 37 CFR 1.19(b)(3).

The invention claimed is:

1. A soybean plant, soybean plant part, or soybean plant cell comprising a recombinant nucleic acid molecule, said recombinant nucleic acid molecule comprising:
a nongenic nucleic acid molecule of at least 1 Kb, wherein
   a. the level of methylation of said nongenic nucleic acid molecule is 1% or less;
   b. the nongenic nucleic acid molecule shares less than 40% sequence identity with any other nucleic acid molecules contained in the soybean genome;
   c. the nongenic nucleic acid molecule is located within a 40 Kb region of a known or predicted expressive soybean coding nucleic acid molecule; and
   d. the nongenic nucleic acid molecule exhibits a recombination frequency within the soybean genome of greater than 0.01574 cM/Mb, wherein said nongenic nucleic acid molecule has at least 95% sequence identity with a nongenic nucleic acid molecule selected from the group consisting of
SEQ ID NO:1, identified as soy_OGL_2474,
SEQ ID NO:506, identified as soy_OGL_768,
SEQ ID NO:748, identified as soy_OGL_2063,
SEQ ID NO:1029, identified as soy_OGL_1906,
SEQ ID NO:1166, identified as soy_OGL_1112,
SEQ ID NO:1452, identified as soy_OGL_3574,
SEQ ID NO:1662, identified as soy_OGL_2581, and
SEQ ID NO:3993, identified as soy_OGL_4222; and
a DNA of interest, wherein the DNA of interest is inserted into said nongenic nucleic acid molecule to produce said recombinant nucleic acid molecule.

2. The soybean plant, soybean plant part, or soybean plant cell of claim 1 wherein said DNA of interest is inserted within 2 Kb, 1.75 Kb, 1.5 Kb, 1.25 Kb, 1.0 Kb, 0.75 Kb, 0.5 Kb, or 0.25 Kb of a zinc finger target site.

3. The soybean plant, soybean plant part, or soybean plant cell of claim 1, wherein said DNA of interest comprises a gene expression cassette encoding an insect resistance gene, herbicide tolerance gene, nitrogen use efficiency gene, water use efficiency gene, nutritional quality gene, DNA binding gene, or a selectable marker gene.

4. The soybean plant, soybean plant part, or soybean plant cell of claim 1, wherein said DNA of interest comprises two or more gene expression cassettes.

5. The soybean plant, soybean plant part, or soybean plant cell of claim 1, wherein two or more of said nongenic nucleic acid molecules each comprise an inserted DNA of interest to produce two or more recombinant nucleic acid molecules wherein the two or more recombinant nucleic acid molecules are located on a same chromosome.

6. The soybean plant, soybean plant part, or soybean plant cell of claim 1 wherein said DNA of interest comprises an open reading frame and said DNA of interest is inserted into said nongenic nucleic acid molecule to produce said recombinant nucleic acid molecule.

7. A method of making a transgenic plant cell comprising a DNA of interest, the method comprising:
   a. selecting a target nongenic soybean genomic nucleic acid molecule of at least 1 Kb, wherein
      i. the level of methylation of said nongenic nucleic acid molecule is 1% or less;
      ii. the nongenic nucleic acid molecule shares less than 40% sequence identity with any other nucleic acid molecule contained in the soybean genome;
      iii. the nongenic nucleic acid molecule is located within a 40 Kb region of a known or predicted expressive soybean coding nucleic acid molecule; and
      iv. the nongenic nucleic acid molecule exhibits a recombination frequency within the soybean genome of greater than 0.01574 cM/Mb, wherein said nongenic nucleic acid molecule has at least 95% sequence identity to a nucleic acid molecule selected from the group consisting of SEQ ID NO:1, identified as soy_OGL_2474,
SEQ ID NO:506, identified as soy_OGL_768,
SEQ ID NO:748, identified as soy_OGL_2063,
SEQ ID NO:1029, identified as soy_OGL_1906,
SEQ ID NO:1166, identified as soy_OGL_1112,
SEQ ID NO:1452, identified as soy_OGL_3574,
SEQ ID NO:1662, identified as soy_OGL_2581, and
SEQ ID NO:3993, identified as soy_OGL_4222;
b. selecting a site specific nuclease that specifically binds and cleaves said target nongenic soybean genomic nucleic acid molecule;
c. introducing said site specific nuclease into a soybean plant cell;
d. introducing the DNA of interest into the plant cell;
e. inserting the DNA of interest into said target nongenic soybean genomic nucleic acid molecule; and,
f. selecting transgenic plant cells comprising the DNA of interest inserted into said nongenic nucleic acid molecule.

8. The method of making a transgenic plant cell of claim 7, wherein said site specific nuclease is selected from the group consisting of a zinc finger nuclease, a CRISPR nuclease, a TALEN, a homing endonuclease and a meganuclease.

9. The method of making a transgenic plant cell of claim 7, wherein said DNA of interest is integrated within said nongenic nucleic acid molecule via a homology directed repair integration method.

10. The method of making a transgenic plant cell of claim 7, wherein said DNA of interest is integrated within said nongenic nucleic acid molecule via a nonhomologous end joining integration method.

11. The method of making a transgenic plant cell of claim 7, wherein two or more of said DNA of interest are inserted into two or more of said target nongenic soybean genomic nucleic acid molecules, optionally on a same chromosome.

12. A recombinant soybean cell produced by the following steps:
a. providing a soybean cell wherein said cell comprises a target nongenic soybean genomic nucleic acid molecule having at least 95% sequence identity to a nucleic acid molecule selected from the group consisting of
SEQ ID NO:1, identified as soy_OGL_2474,
SEQ ID NO:506, identified as soy_OGL_768,
SEQ ID NO:748, identified as soy_OGL_2063,
SEQ ID NO:1029, identified as soy_OGL_1906,
SEQ ID NO:1166, identified as soy_OGL_1112,
SEQ ID NO:1452, identified as soy_OGL_3574,
SEQ ID NO:1662, identified as soy_OGL_2581, and
SEQ ID NO:3993, identified as soy_OGL_4222;
b. selecting a site specific nuclease that specifically binds and cleaves said target nongenic soybean genomic nucleic acid molecule;
c. introducing said site specific nuclease activity into said soybean cell;
d. introducing a DNA of interest into the soybean cell;
e. inserting the DNA of interest into said target nongenic soybean genomic nucleic acid molecule; and,
f. selecting transgenic soybean cells comprising the DNA of interest inserted into said nongenic nucleic acid molecule.

13. A soybean plant regenerated from the soybean cell of claim 12.

14. A seed or other soybean plant part of the plant of claim 13, wherein the soybean seed or plant part comprises said DNA of interest inserted into said nongenic nucleic acid molecule.

15. The soybean cell of claim 12 wherein the site specific nuclease is a Zinc Finger Nuclease and said DNA of interest is inserted within 2 Kb, 1.75 Kb, 1.5 Kb, 1.25 Kb, 1.0 Kb, 0.75 Kb, 0.5 Kb, or 0.25 Kb of a zinc finger target site.

16. The soybean cell of claim 12 wherein the DNA of interest comprises a gene expression cassette encoding an insect resistance gene, herbicide tolerance gene, nitrogen use efficiency gene, water use efficiency gene, nutritional quality gene, DNA binding gene, or selectable marker gene.

17. A soybean plant, soybean plant part, or soybean plant cell comprising a nucleic acid molecule encoding a site specific nuclease, wherein the site specific nuclease is selected from the group consisting of a zinc finger nuclease, a CRISPR nuclease, a TALEN, a homing endonuclease and a meganuclease, that specifically binds and cleaves a target nongenic soybean genomic nucleic acid molecule selected from the group consisting of
SEQ ID NO:1, identified as soy_OGL_2474,
SEQ ID NO:506, identified as soy_OGL_768,
SEQ ID NO:748, identified as soy_OGL_2063,
SEQ ID NO:1029, identified as soy_OGL_1906,
SEQ ID NO:1166, identified as soy_OGL_1112,
SEQ ID NO:1452, identified as soy_OGL_3574,
SEQ ID NO:1662, identified as soy_OGL_2581, and
SEQ ID NO:3993, identified as soy_OGL_4222.

18. The soybean plant, soybean plant part, or soybean plant cell of claim 17 wherein the nucleic acid molecule encoding the site specific nuclease is operably linked to an inducible promoter.

19. The soybean plant, soybean plant part, or soybean plant cell of claim 3 wherein said nongenic nucleic acid molecule has at least 95% sequence identity with a nongenic nucleic acid molecule selected from the group consisting of
SEQ ID NO:1, identified as soy_OGL_2474,
SEQ ID NO:506, identified as soy_OGL_768,
SEQ ID NO:748, identified as soy_OGL_2063,
SEQ ID NO:1029, identified as soy_OGL_1906, and
SEQ ID NO:1166, identified as soy_OGL_1112.

* * * * *